(12) United States Patent
Tanaka et al.

(10) Patent No.: US 11,101,433 B2
(45) Date of Patent: Aug. 24, 2021

(54) LIGHT-EMITTING MATERIAL, AND DELAYED FLUORESCENT EMITTER AND ORGANIC LIGHT-EMITTING DEVICE USING SAME

(71) Applicant: KYULUX, INC., Fukuoka (JP)

(72) Inventors: Hiroyuki Tanaka, Fukuoka (JP); Hiroki Noda, Fukuoka (JP); Katsuyuki Shizu, Fukuoka (JP); Masatsugu Taneda, Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 15/036,129

(22) PCT Filed: Nov. 12, 2014

(86) PCT No.: PCT/JP2014/079914
§ 371 (c)(1),
(2) Date: May 12, 2016

(87) PCT Pub. No.: WO2015/072470
PCT Pub. Date: May 21, 2015

(65) Prior Publication Data
US 2016/0308145 A1  Oct. 20, 2016

(30) Foreign Application Priority Data
Nov. 12, 2013  (JP) .............................. JP2013-234434

(51) Int. Cl.
*H01L 51/00* (2006.01)
*C07D 403/14* (2006.01)
*C09K 11/06* (2006.01)
*C07D 403/10* (2006.01)
*C09K 11/02* (2006.01)
*H01L 51/50* (2006.01)

(52) U.S. Cl.
CPC ........ *H01L 51/0072* (2013.01); *C07D 403/10* (2013.01); *C07D 403/14* (2013.01); *C09K 11/025* (2013.01); *C09K 11/06* (2013.01); *H01L 51/005* (2013.01); *H01L 51/0067* (2013.01); *C09K 2211/1007* (2013.01); *C09K 2211/1029* (2013.01); *C09K 2211/1044* (2013.01); *C09K 2211/1059* (2013.01); *H01L 51/5012* (2013.01)

(58) Field of Classification Search
CPC .... C07D 403/10; C07D 403/14; C09K 11/06; C09K 11/025; C09K 2211/1029; C09K 2211/1044; C09K 2211/1059; C09K 2211/1007; H01L 51/0072; H01L 51/0067; H01L 51/005; H01L 51/5012
See application file for complete search history.

(56) References Cited

U.S. PATENT DOCUMENTS

| 2011/0278555 | A1* | 11/2011 | Inoue | C07D 209/82 257/40 |
| 2011/0279020 | A1 | 11/2011 | Inoue et al. | |
| 2012/0205636 | A1* | 8/2012 | Kim | C09K 11/06 257/40 |
| 2012/0211736 | A1* | 8/2012 | Kim | C09K 11/06 257/40 |
| 2013/0234119 | A1* | 9/2013 | Mizuki | H01L 51/0072 257/40 |

(Continued)

FOREIGN PATENT DOCUMENTS

| CN | 102439004 | 2/2012 |
| CN | 102884156 | 1/2013 |

(Continued)

OTHER PUBLICATIONS

English language translation of WO 2011/162162, pp. 1-32, Jul. 18, 2017.*

(Continued)

*Primary Examiner* — Alexander C Kollias
(74) *Attorney, Agent, or Firm* — Browdy and Neimark, PLLC

(57) ABSTRACT

A light-emitting material containing a compound represented by the general formula (1) is capable of achieving an excellent external quantum efficiency on using in an organic light-emitting device. $R^1$ to $R^8$ represent a hydrogen atom or a substituent, provided that at least one of $R^1$ to $R^8$ represents a substituted or unsubstituted carbazolyl group; and $Ar^1$ to $Ar^3$ represent a substituted or unsubstituted aromatic ring or heteroaromatic ring.

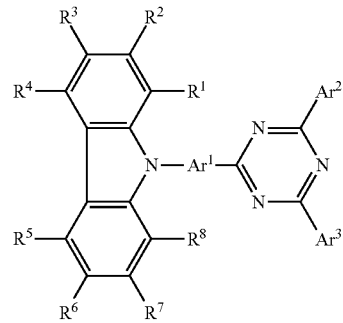

General Formula (1)

18 Claims, 5 Drawing Sheets

(56) References Cited

U.S. PATENT DOCUMENTS

| | | | | |
|---|---|---|---|---|
| 2013/0292659 | A1* | 11/2013 | Kim | C07D 409/14 257/40 |
| 2013/0292664 | A1 | 11/2013 | Nishimura et al. | |
| 2014/0145149 | A1 | 5/2014 | Lin et al. | |
| 2014/0159023 | A1 | 6/2014 | Matsumoto et al. | |
| 2014/0299865 | A1* | 10/2014 | Nishimura | H01L 51/0067 257/40 |
| 2014/0336379 | A1 | 11/2014 | Adachi et al. | |
| 2015/0340623 | A1* | 11/2015 | Kawamura | C07D 491/048 257/40 |
| 2015/0357582 | A1* | 12/2015 | Hirata | C07D 403/14 257/40 |
| 2016/0204361 | A1* | 7/2016 | Mizuki | C07D 209/86 257/40 |

FOREIGN PATENT DOCUMENTS

| | | |
|---|---|---|
| EP | 2980877 A1 | 2/2016 |
| JP | 2014105209 A | 6/2014 |
| JP | 2014-141571 A | 8/2014 |
| JP | 2014-141572 A | 8/2014 |
| WO | 2011/049325 A2 | 4/2011 |
| WO | 2011/132683 A1 † | 10/2011 |
| WO | 2011132683 A1 | 10/2011 |
| WO | 2011132684 A1 | 10/2011 |
| WO | 2011/162162 A1 † | 12/2011 |
| WO | 2012077902 A2 | 6/2012 |
| WO | 2012099241 A1 | 7/2012 |
| WO | 2012157211 A1 | 11/2012 |
| WO | 2013081088 A1 | 6/2013 |
| WO | 2014092083 A1 | 6/2014 |
| WO | 2014104315 A1 | 7/2014 |
| WO | 2014115743 A1 | 7/2014 |
| WO | 2014157619 A1 | 10/2014 |

OTHER PUBLICATIONS

Michael Fowlet, Black Body Radiation, pp. 1-16.*
S. Y. Lee et al "High-efficiency organic light-emitting diodes utilizing thermally activated delayed fluorescence from triazine-based donor-acceptor hybrid molecules" Applies Physics Letters, 101: 093306-1-4 (2012).
International Preliminary Report dated May 26, 2016, in corresponding application No. PCT/JP2014/079914.
International Search Report, written opinion and partial translation dated Dec. 22, 2014, in corresponding application No. PCT/JP2014/079914.
Office action and English machine translation from Chinese patent application 201480061957.5 dated May 4, 2017.
Office Action dated Jan. 24, 2018 issued in the corresponding Chinese patent application No. 201480061957.5 with English Machine Translation.
Office Action dated Aug. 28, 2018, issued in the corresponding Japanese patent application No. 2015-547765 with English Machine Translation.
Office Action dated Aug. 28, 2018 issued in the corresponding Chinese patent application No. 201480061957.5 with its English Translation.
Sae Youn Lee, et al., "High-efficiency organic light-emitting diodes utilizing thermally activated delayed fluorescence from triazine-based donor-acceptor hybrid molecules", pp. 093306-1 to 093306-4, Aug. 30, 2012, Applied Physics Letters 101, American Institute of Physics.†

* cited by examiner
† cited by third party

LIGHT-EMITTING MATERIAL, AND DELAYED FLUORESCENT EMITTER AND ORGANIC LIGHT-EMITTING DEVICE USING SAME

TECHNICAL FIELD

The present invention relates to a delayed fluorescent emitter and an organic light-emitting device, using a useful light-emitting material.

BACKGROUND ART

An organic light-emitting device, such as an organic electroluminescent device (organic EL device), has been actively studied for enhancing the light emission efficiency thereof. In particular, various studies for enhancing the light-emitting efficiency have been made by newly developing and combining an electron transporting material, a hole transporting material, a light-emitting material and the like constituting an organic electroluminescent device. There are studies relating to an organic electroluminescent device utilizing a compound containing a triazine ring and a carbazole ring.

For example, PTLs 1 and 2 describe the use of a compound containing a carbazole ring as a host material for a phosphorescent light-emitting material along with a phosphorescent material in a light-emitting layer present between a pair of electrodes constituting an organic electroluminescent device. The literatures exemplify a compound further containing a triazine ring as the compound containing a carbazole ring.

CITATION LIST

Patent Literatures

PTL 1: WO 2011/132683
PTL 2: WO 2012/077902

SUMMARY OF INVENTION

Technical Problem

PTLs 1 and 2 describe the use of a compound containing a triazine ring and a carbazole ring as a host material of a light-emitting layer of an organic electroluminescent device. However, there is no specific description as to whether or not the compound described in PTLs 1 and 2 is capable of functioning as a light-emitting material. A light-emitting material and a host material have functions different from each other, and therefore the usefulness of the compound described in PTLs 1 and 2 as a light-emitting material is unknown.

Under the circumstances, the present inventors have made extensive investigations for finding a compound excellent in light emission characteristics. The inventors have made earnest investigations intending to derive a general formula of a compound useful as a light-emitting material and to generalize a constitution of an organic light-emitting device having a high light emission efficiency.

An object of the invention is to provide a light-emitting material that is capable of achieving an excellent external quantum efficiency on using in an organic light-emitting device, and a delayed fluorescent emitter and an organic light-emitting device using the same.

Solution to Problem

As a result of earnest investigations, the inventors have found that a group of compounds having a particular structure have excellent properties as a light-emitting material. Furthermore, the inventors have found that the group of compounds include a compound that is useful as a delayed fluorescent emitter, and have clarified that an organic light-emitting device having a high light emission efficiency can be provided inexpensively. Thus, the inventors have provided the following invention as a measure for solving the problem based on the knowledge.

[1] A light-emitting material containing a compound represented by the following general formula (1):

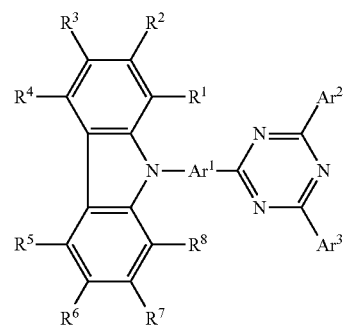

General Formula (1)

wherein in the formula, $R^1$ to $R^8$ each independently represent a hydrogen atom or a substituent, provided that at least one of $R^1$ to $R^8$ represents a substituted or unsubstituted carbazolyl group; and $Ar^1$ to $Ar^3$ each independently represent a substituted or unsubstituted aromatic ring or heteroaromatic ring.

[2] The light-emitting material according to the item [1], wherein in the general formula (1), at least one of $R^3$ and $R^6$ represents a substituted or unsubstituted carbazolyl group.

[3] The light-emitting material according to the item [1] or [2], wherein the carbazolyl group is a 1-carbazolyl group, a 2-carbazolyl group, a 3-carbazolyl group, or a 4-carbazolyl group.

[4] The light-emitting material according to any one of the items [1] to [3], wherein the carbazolyl group has a substituent on the nitrogen atom in the carbazole ring structure.

[5] The light-emitting material according to any one of the items [1] to [4], wherein in the general formula (1), at least one of $Ar^1$, $Ar^2$, and $Ar^3$ represents a benzene ring or a naphthalene ring.

[6] The light-emitting material according to any one of the items [1] to [5], wherein in the general formula (1), $Ar^1$, $Ar^2$, and $Ar^3$ represent the same aromatic rings or heteroaromatic rings.

[7] The light-emitting material according to any one of the items [1] to [6], wherein in the general formula (1), $Ar^1$, $Ar^2$, and $Ar^3$ represent benzene rings.

[8] A delayed fluorescent emitter containing the compound according to any one of the items [1] to [7].

[9] An organic light-emitting device containing a substrate having thereon a light-emitting layer containing the light-emitting material according to the item [8].

[10] The organic light-emitting device according to the item [9], wherein the organic light-emitting device emits delayed fluorescent light.

[11] The organic light-emitting device according to the item [9] or [10], wherein the organic light-emitting device is an organic electroluminescent device.

[12] A compound represented by the following general formula (1'):

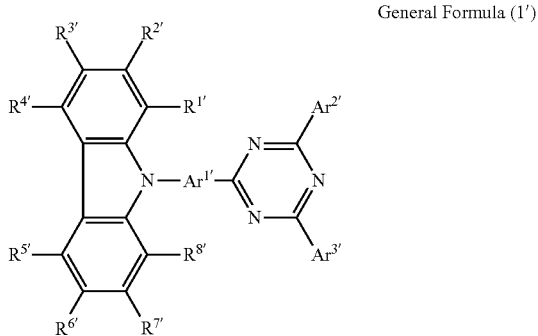

General Formula (1')

wherein in the formula, $R^{1'}$ to $R^{8'}$ each independently represent a hydrogen atom or a substituent, provided that at least one of $R^{1'}$ to $R^{8'}$ represents a substituted or unsubstituted 1-carbazolyl group, a substituted or unsubstituted 2-carbazolyl group, a substituted or unsubstituted 3-carbazolyl group, or a substituted or unsubstituted 4-carbazolyl group, provided that the 9-position of the carbazolyl groups is unsubstituted; and $Ar^{1'}$ to $Ar^{3'}$ each independently represent a substituted or unsubstituted aromatic ring or heteroaromatic ring.

[13] The compound according to the item [12], wherein in the general formula (1'), at least one of $R^{1'}$ to $R^{8'}$ represents a substituted or unsubstituted 3-carbazolyl group.

Advantageous Effects of Invention

The compound of the invention is useful as a light-emitting material. The compound of the invention includes one that emits delayed fluorescent light. The organic light-emitting device using the compound of the invention as a light-emitting material or a delayed fluorescent emitter is capable of achieving a high light emission efficiency.

DESCRIPTION OF EMBODIMENTS

Figure 1:
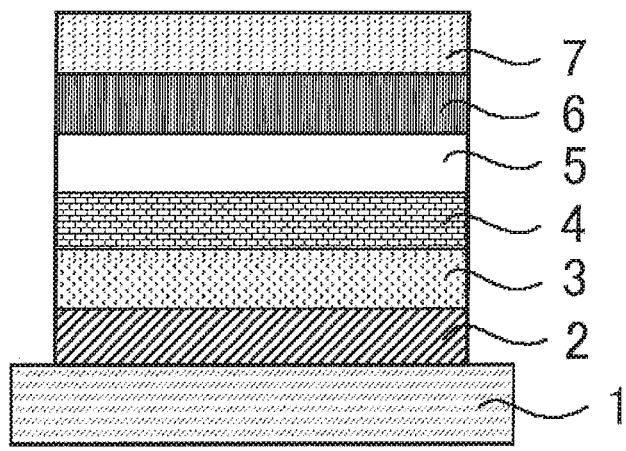
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit.

In the invention, the hydrogen atom that is present in the compound used in the invention is not particularly limited in isotope species, and for example, all the hydrogen atoms in the molecule may be $^1H$, and all or a part of them may be $^2H$ (deuterium (D)).

Compound represented by General Formula (1)

The compound of the invention has a structure represented by the following general formula (1).

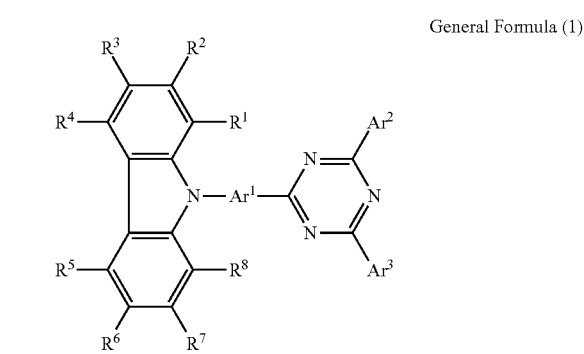

General Formula (1)

In the general formula (1), $R^1$ to $R^8$ each independently represent a hydrogen atom or a substituent, provided that at least one of $R^1$ to $R^8$ represents a substituted or unsubstituted carbazolyl group; and $Ar^1$ to $Ar^3$ each independently represent a substituted or unsubstituted aromatic ring or heteroaromatic ring.

The compound represented by the general formula (1) is constituted by a carbazole ring moiety containing $R^1$ to $R^8$ and a triazine ring moiety containing $Ar^1$ to $Ar^3$ bonded to the carbazole ring moiety through $Ar^1$.

In the carbazole ring moiety containing $R^1$ to $R^8$, examples of the substituent represented by $R^1$ to $R^8$ include a hydroxyl group, a halogen atom, an alkyl group having from 1 to 20 carbon atoms, an alkoxy group having from 1 to 20 carbon atoms, an alkylthio group having from 1 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, a haloalkyl group having from 1 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, and a trialkylsilylalkynyl group having from 5 to 20 carbon atoms. In these specific examples, the substituent that is capable of being further substituted with a substituent may be substituted. More preferred examples of the substituent include a substituted or unsubstituted alkyl group having from 1 to 20 carbon atoms, an alkoxy group having from 1 to 20 carbon atoms, a substituted or unsubstituted aryl group having from 6 to 40 carbon atoms, and a substituted or unsubstituted heteroaryl group having from 3 to 40 carbon atoms. Further preferred examples of the substituent include a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

$R^1$ and $R^2$, $R^2$ and $R^3$, $R^3$ and $R^4$, $R^4$ and $R^5$, $R^5$ and $R^6$, $R^6$ and $R^7$, and $R^7$ and $R^8$ each may be bonded to each other to form a cyclic structure. The cyclic structure may be an aromatic ring or an aliphatic ring, may contain a hetero atom, and may be a condensed ring containing two or more rings. The hetero atom referred herein is preferably selected from a group consisting of a nitrogen atom, an oxygen atom, and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, and a cycloheptaene ring.

In the general formula (1), at least one of $R^1$ to $R^8$ represents a substituted or unsubstituted carbazolyl group. In the compound represented by the general formula (1), two or more of $R^1$ to $R^8$ may be carbazolyl groups. The number of a carbazolyl group bonded as $R^1$ to $R^8$ to the compound represented by the general formula (1) is preferably from 1 to 6, more preferably from 1 to 4, and may be selected, for example, from 1 or 2. Any portion of $R^1$ to $R^8$ in the general formula (1) may be a carbazolyl group, and at least one of $R^3$ and $R^6$ is preferably a carbazolyl group. In the carbazolyl group, the portion that is bonded to the compound represented by the general formula (1) is not particularly limited, and the carbazolyl group is preferably a 1-carbazolyl group, a 2-carbazolyl group, a 3-carbazolyl group, or a 4-carbazolyl group bonded to the general formula (1) at the 1- to 4-positions of the carbazole ring, and more preferably a 3-carbazolyl group bonded to the general formula (1) at the 3-position of the carbazole ring. A 6-carbazolyl group bonded to the compound represented by the general formula (1) at the 6-position of the carbazole ring is regarded as the same as the 3-carbazolyl group.

The carbazolyl group bonded as $R^1$ to $R^8$ in the general formula (1) may be substituted by a substituent. The number of the substituent is not particularly limited, and the substituent may not be present. In the case where two or more substituents are present, the substituents may be the same as or different from each other. Examples of the substituent include the same ones as the substituent represented by $R^1$ to $R^8$, and the preferred examples thereof are also the same. The substituent may be, for example, a phenyl group, or a group having a triphenyltriazine ring, such as a group having a 2,4,6-triphenyl-1,3,5-triazine ring and a group having a hexahydro-1,3,5-triphenyl-1,3,5-triazine ring. The position where the substituent of the carbazolyl group is bonded is not particularly limited, and in the case where the carbazolyl group has a substituent, the carbazolyl group preferably has the substituent on the nitrogen atom of the carbazole ring structure.

In the triazine ring moiety containing $Ar^1$ to $Ar^3$ in the general formula (1), $Ar^1$, $Ar^2$, and $Ar^3$ each represent a substituted or unsubstituted aromatic ring or heteroaromatic ring. The aromatic ring or heteroaromatic ring may be a monocyclic ring or a condensed ring. The number of ring-forming carbon atoms of the aromatic ring or heteroaromatic ring is preferably from 6 to 20, more preferably from 6 to 12, and further preferably from 6 to 10. The aromatic ring or heteroaromatic ring represented by $Ar^1$, $Ar^2$, and $Ar^3$ may be the same aromatic ring or heteroaromatic ring, or may be aromatic rings or heteroaromatic rings different from each other. $Ar^1$, $Ar^2$, and $Ar^3$ may be substituted by a substituent. The number of the substituent is not particularly limited, and the substituent may not be present. In the case where two or more substituents are present, the substituents may be the same as or different from each other.

In the general formula (1), $Ar^1$, $Ar^2$, and $Ar^3$ each independently represent a substituted or unsubstituted aromatic ring, a substituted or unsubstituted heteroaromatic ring, or a linking group containing any two groups thereof bonded to each other. The linking group containing two groups bonded to each other includes a group containing the same two aromatic rings bonded to each other, a group containing different two aromatic rings bonded to each other, a group containing the same two heteroaromatic rings bonded to each other, a group containing different two heteroaromatic rings bonded to each other, and a group containing an aromatic ring and a heteroaromatic ring bonded to each other.

The aromatic ring that may be represented by $Ar^1$, $Ar^2$, and $Ar^3$ may be a monocyclic aromatic ring or a condensed aromatic ring as described above. The aromatic ring is preferably a benzene ring or a naphthalene ring, and more preferably a benzene ring. Specific examples thereof include a 1,2-phenylene group, a 1,3-phenylene group, a 1,4-phenylene group, a 1,2-naphthylene group, a 1,3-naphthylene group, a 1,4-naphthylene group, a 1,5-naphthylene group, and a 1,8-naphthylene group, and 1,4-phenylene group and a 1,4-naphthylene group are preferred. The heteroaromatic ring that may also be represented by $Ar^1$, $Ar^2$, and $Ar^3$ may be a monocyclic heteroaromatic ring or a condensed heteroaromatic ring. The heteroaromatic ring preferably contains a nitrogen atom as a ring skeleton-forming atom, and the number of the nitrogen atom is preferably from 1 to 4, and more preferably from 1 to 3. The condensed heteroaromatic ring includes a condensed ring of a benzene ring and a heterocyclic ring. Examples of the ring structure constituting the heteroaromatic ring include a pyridine ring, a pyridazine ring, a pyrimidine ring, a triazine ring, a triazole ring, and a benzotriazole ring, and a pyridine ring is preferred.

The bonding position of the aromatic ring and the heteroaromatic ring that may be represented by $Ar^1$, $Ar^2$, and $Ar^3$ is not particularly limited, and for $Ar^1$, for example, the bonding position thereof may be any of the ortho-, meta-, and para-positions.

Specific examples (Group 1) of $Ar^1$ are shown below. The hydrogen atom in the structures shown in Group 1 may be substituted by a substituent.

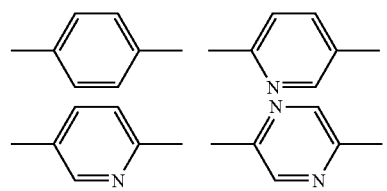

Group 1

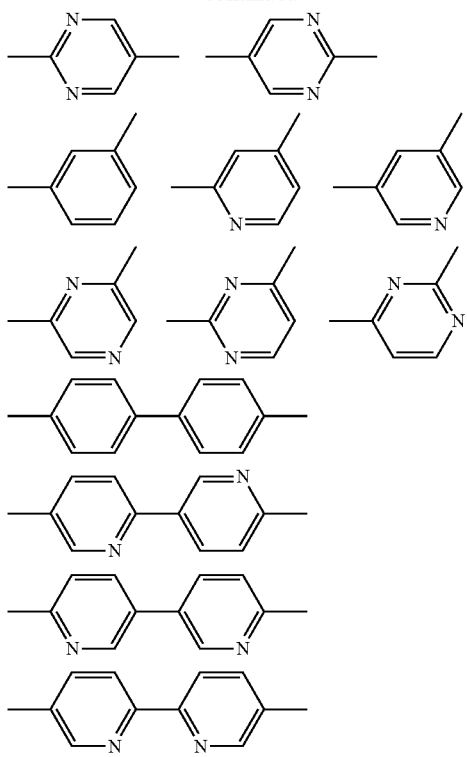

Preferred examples in Group 1 are the following groups.

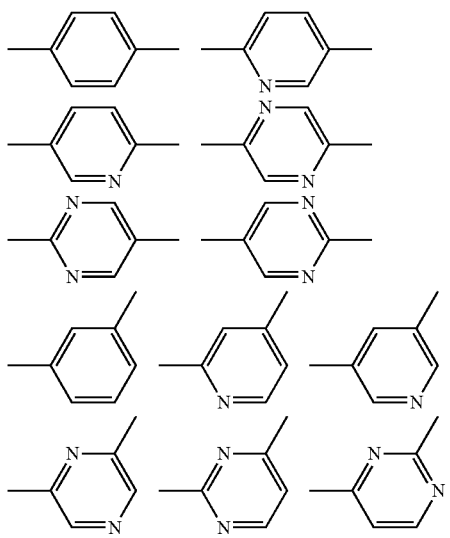

Specific examples (Group 2) of Ar² and Ar³ are shown below. The hydrogen atom in the structures shown in Group 2 may be substituted by a substituent.

Group 2

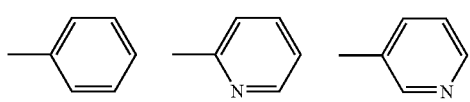

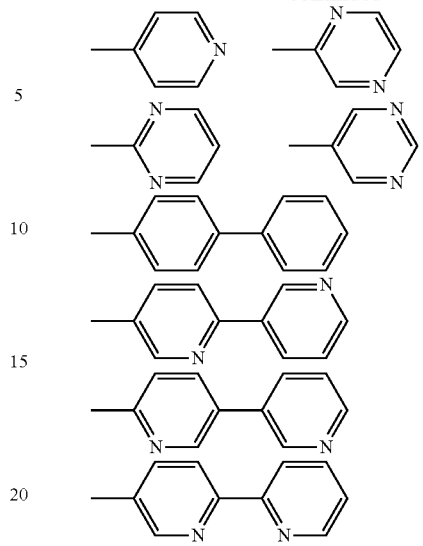

In the case where the aromatic ring or the heteroaromatic ring has a substituent, examples of the substituent include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, a substituted or unsubstituted diarylamino group having from 12 to 40 carbon atoms, and a substituted or unsubstituted carbazolyl group having from 12 to 40 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted dialkylamino group having from 1 to 10 carbon atoms, a substituted or unsubstituted aryl group having from 6 to 15 carbon atoms, and a substituted or unsubstituted heteroaryl group having from 3 to 12 carbon atoms.

The alkyl group referred in the description herein may be any of linear, branched, and cyclic, and preferably has from 1 to 6 carbon atoms, specific examples of which include a methyl group, an ethyl group, a propyl group, a butyl group, a tert-butyl group, a pentyl group, a hexyl group, and an isopropyl group. The alkoxy group may be any of linear, branched, and cyclic, and preferably has from 1 to 6 carbon atoms, specific examples of which include a methoxy group, an ethoxy group, a propoxy group, a butoxy group, a tert-butoxy group, a pentyloxy group, a hexyloxy group, and an isopropoxy group. The aryl group may be a monocyclic ring or a condensed ring, specific examples of which include a phenyl group and a naphthyl group. The heteroaryl group may be a monocyclic ring or a condensed ring, specific examples of which include a pyridyl group, a pyridazyl group, a pyrimidyl group, a triazyl group, a triazolyl group, and a benzotriazolyl group. In the case where plural alkyl groups or aryl groups are present, such as a trialkylsilyl group and a diarylamino group, the plural alkyl groups or aryl groups may be the same as or different from each other, and are preferably the same as each other. In the case where one group has plural alkyl groups, the plural alkyl groups each independently may be any of linear, branched, or cyclic, and more preferably have from 1 to 6 carbon atoms, specific examples of which include a methyl group, an ethyl group, a propyl group, a butyl group, a pentyl group, a hexyl group, and an isopropyl group.

Specific examples of the compound represented by the general formula (1) shown below. However, the compound represented by the general formula (1) capable of being used in the invention is not construed as being limited to the specific examples.

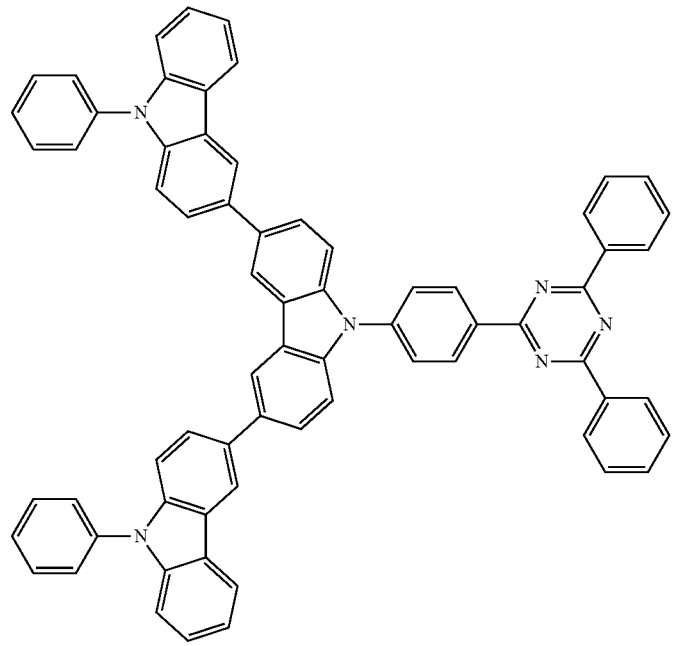

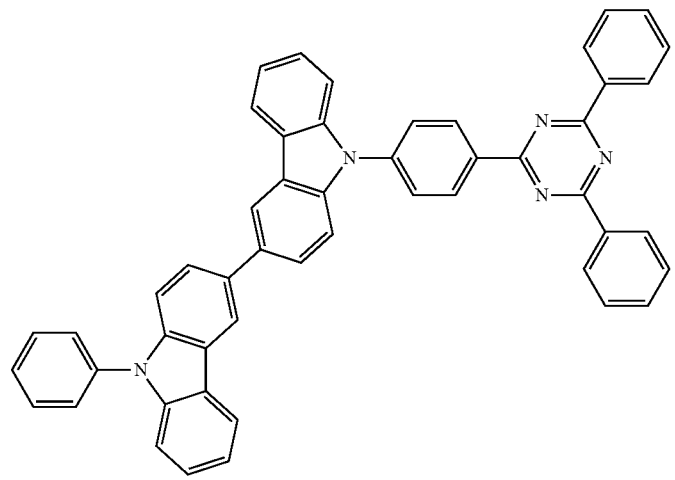

-continued
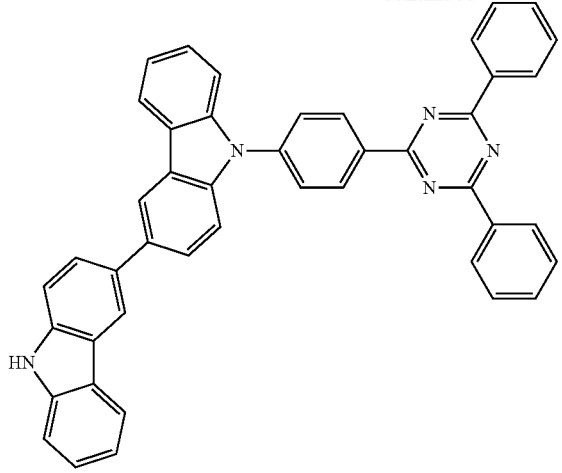
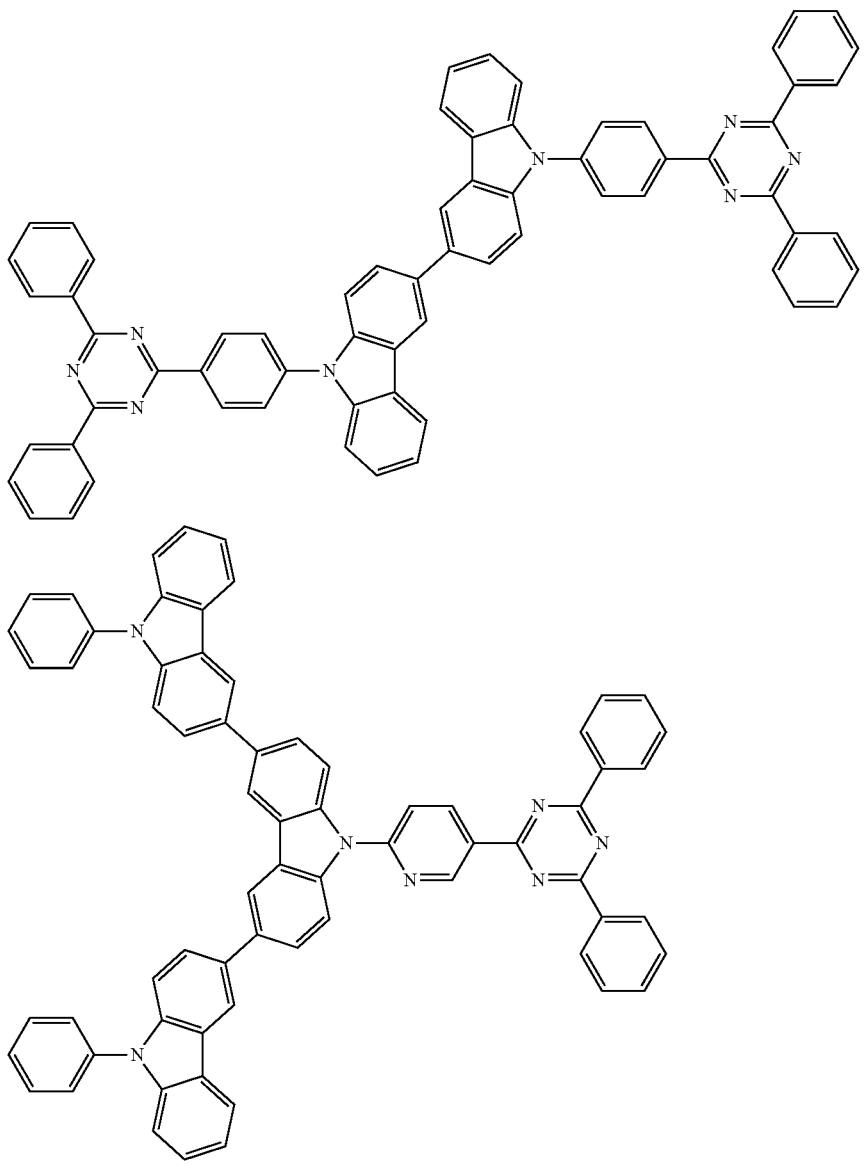

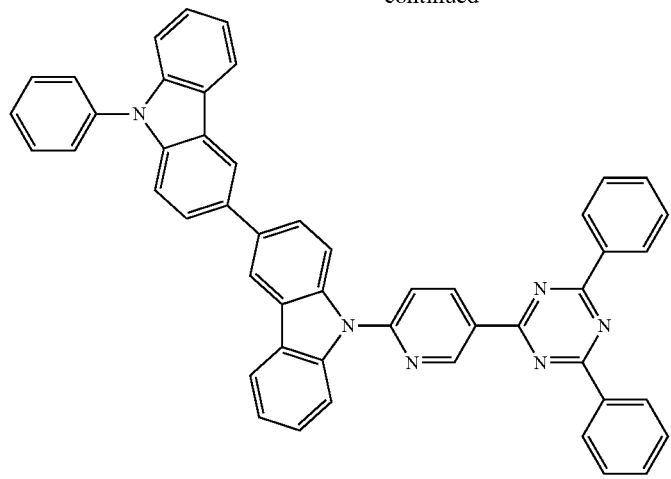
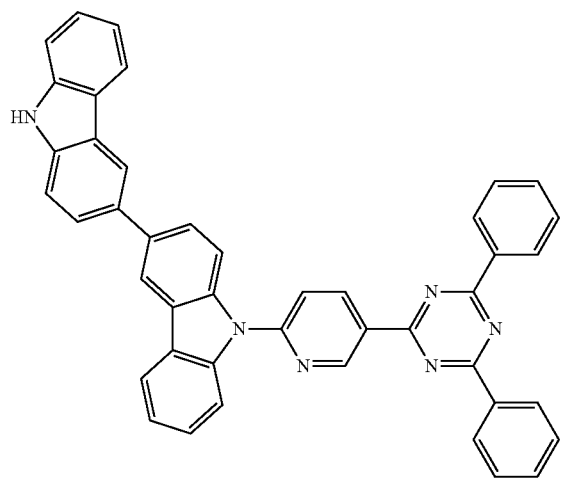
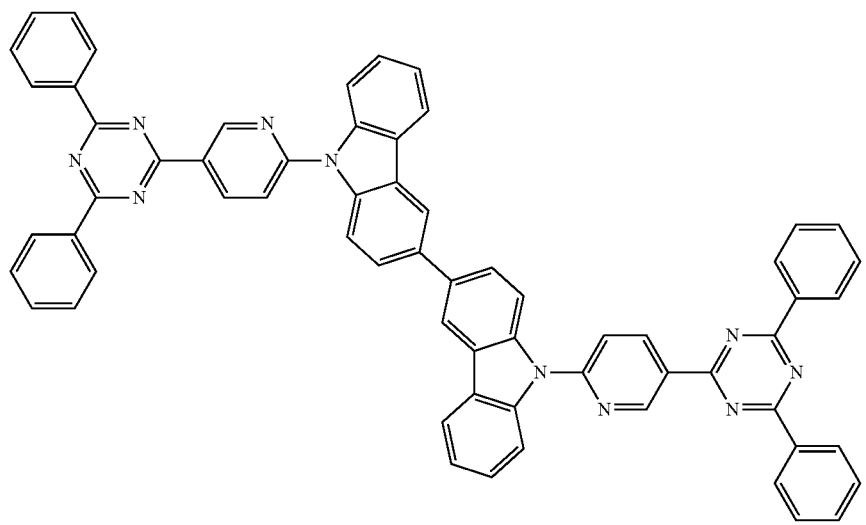

-continued
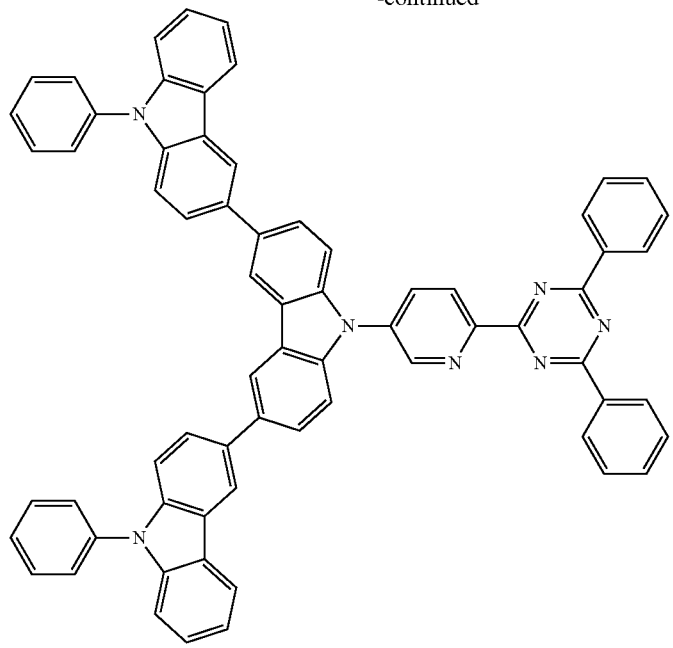
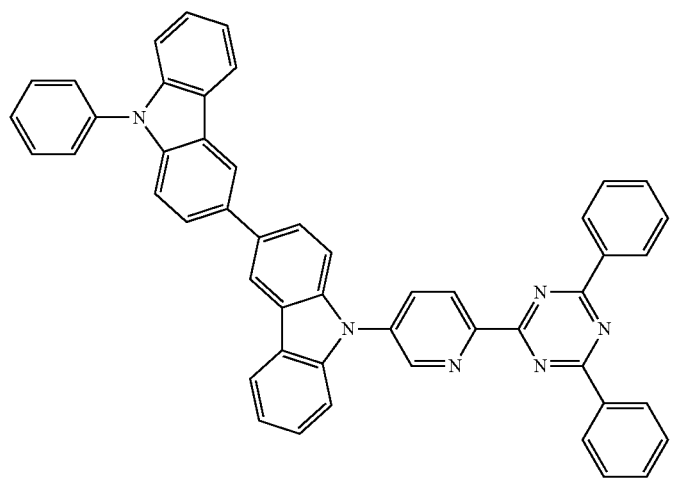
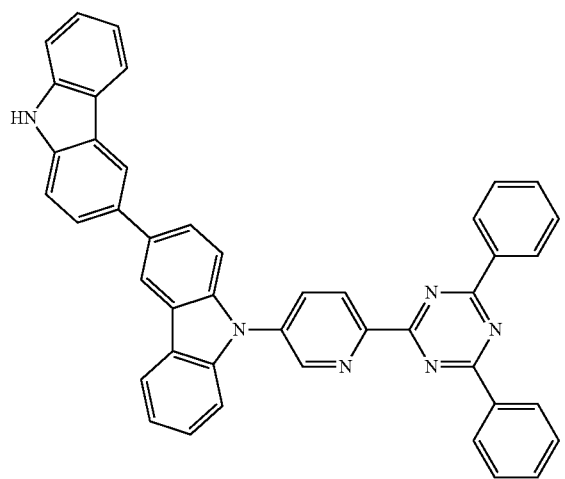

-continued
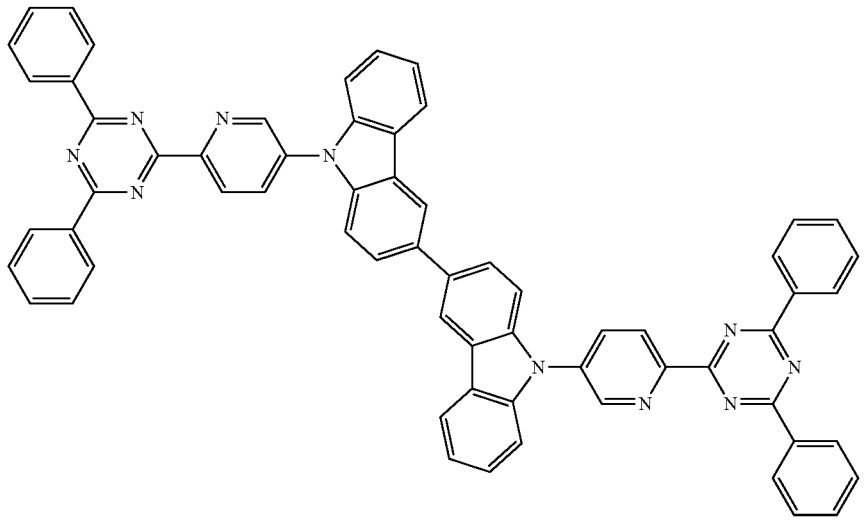
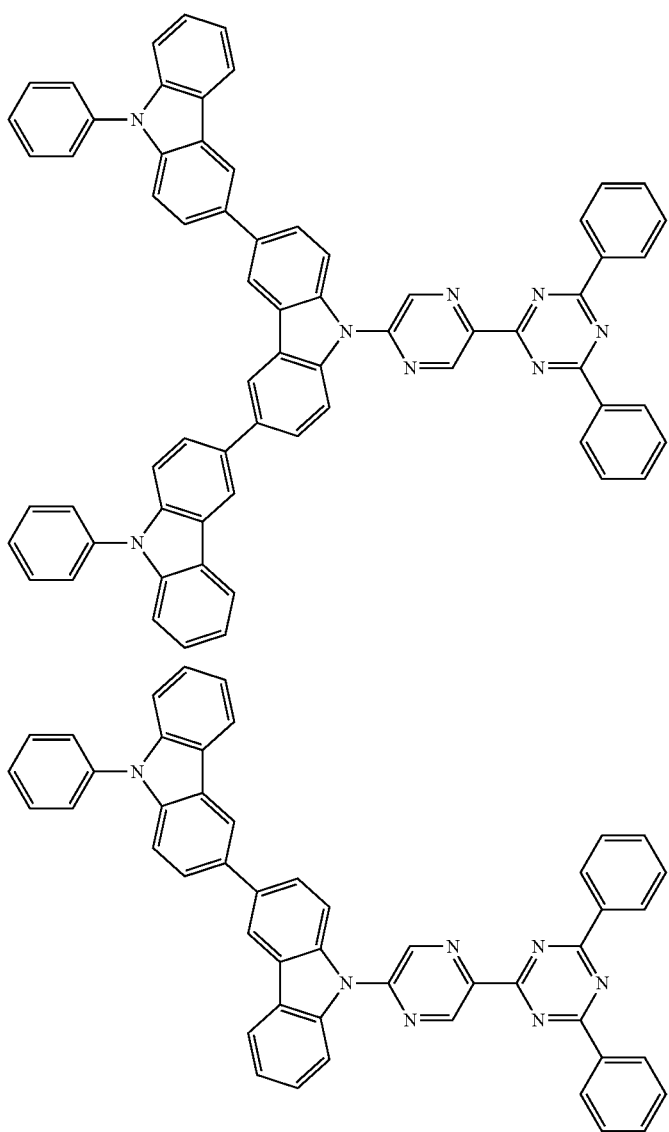

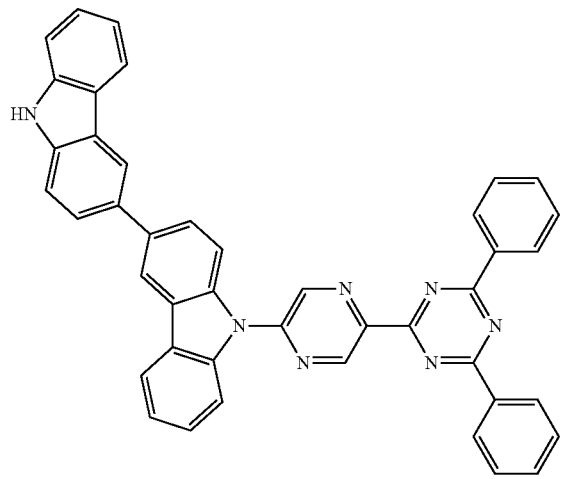
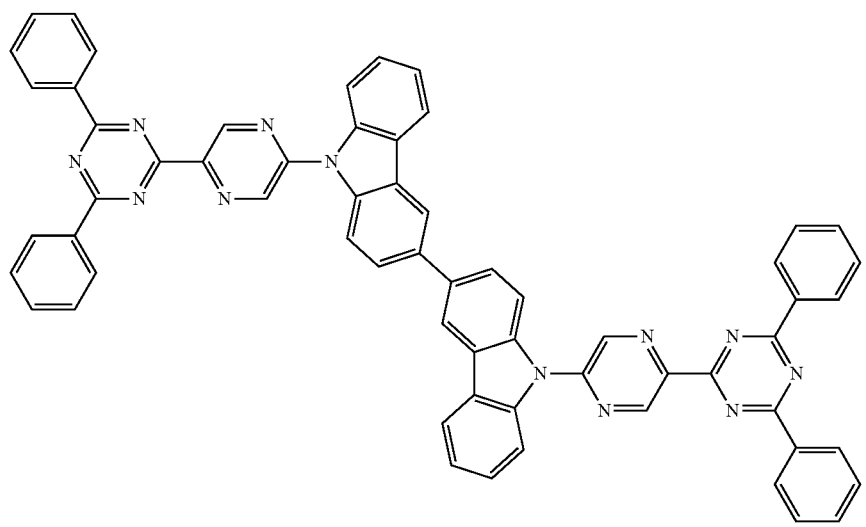
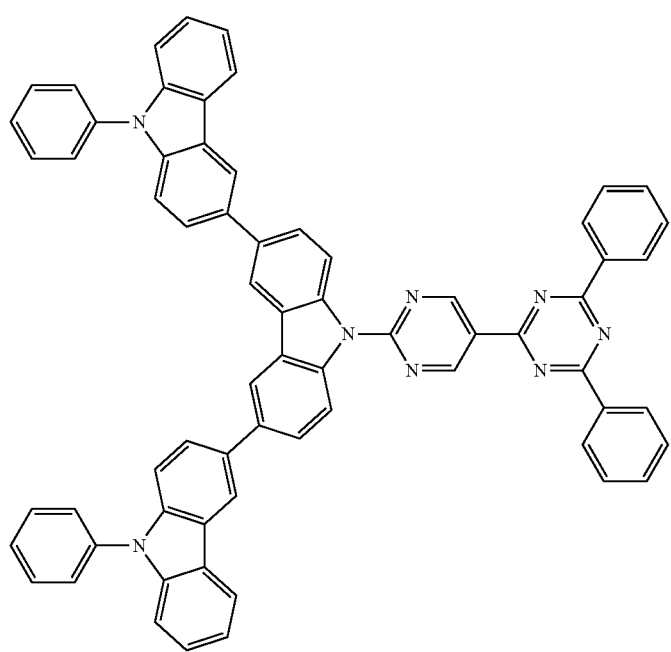

-continued
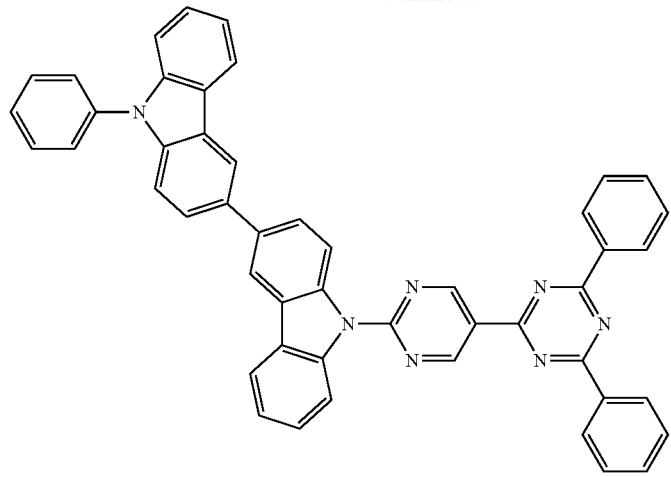
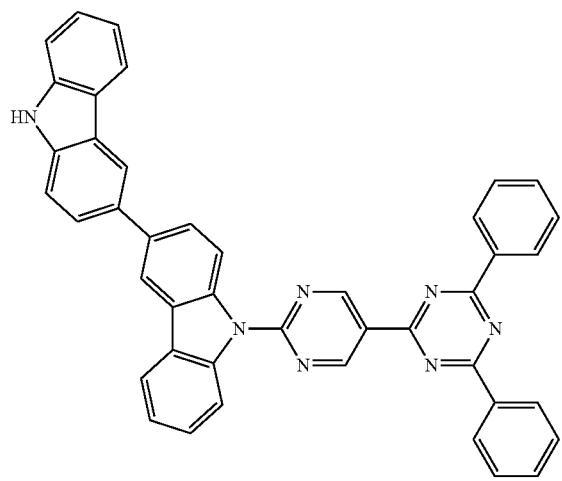
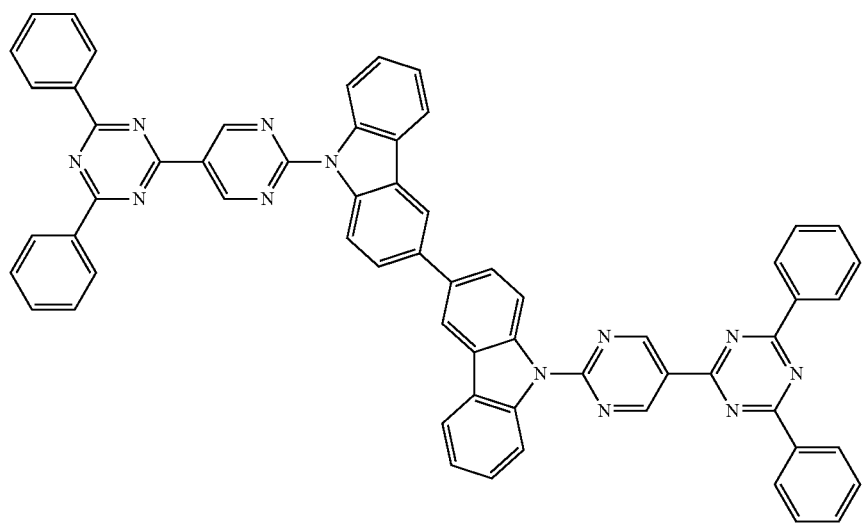

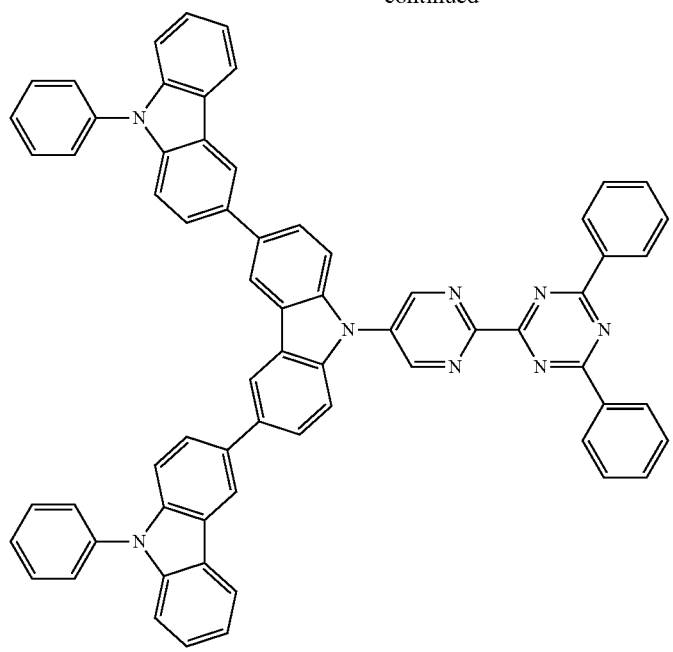
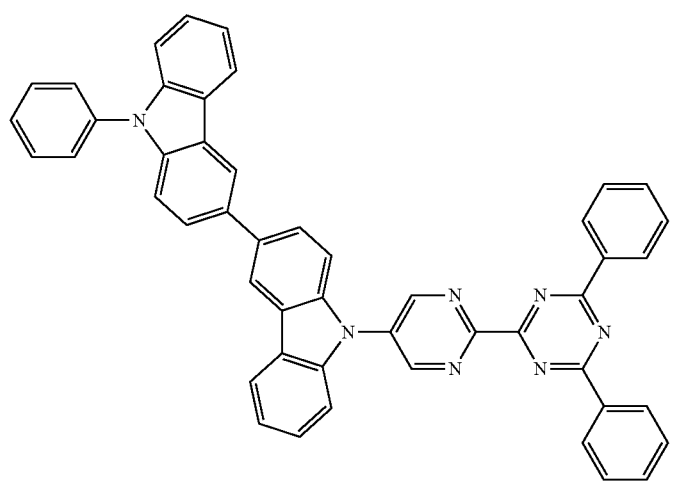
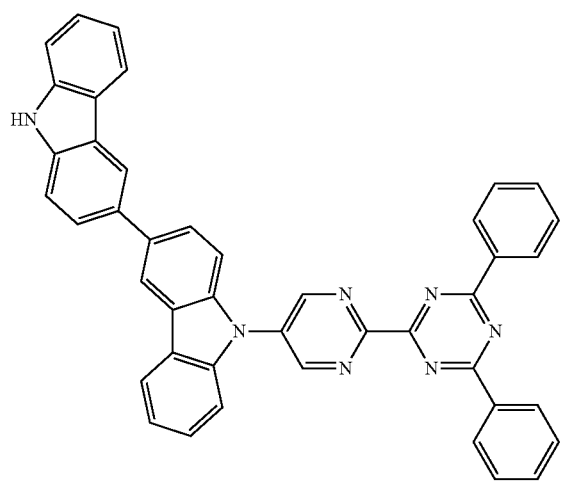

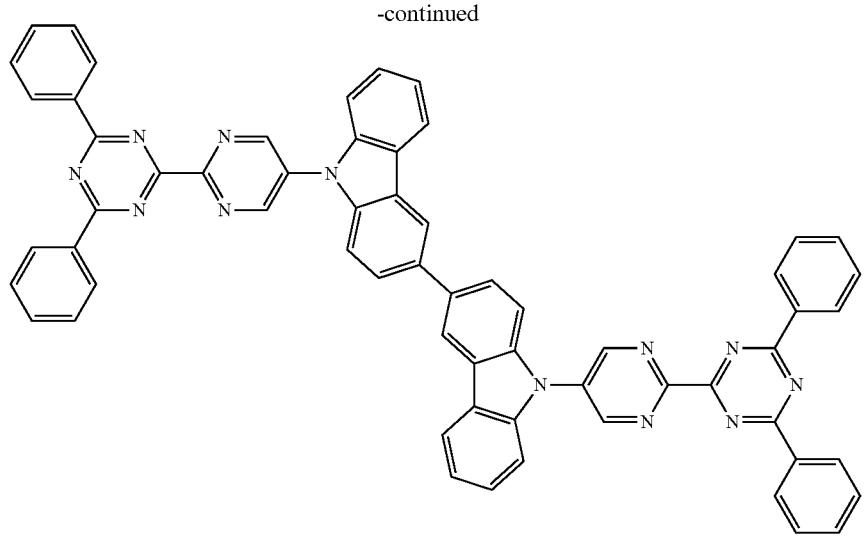
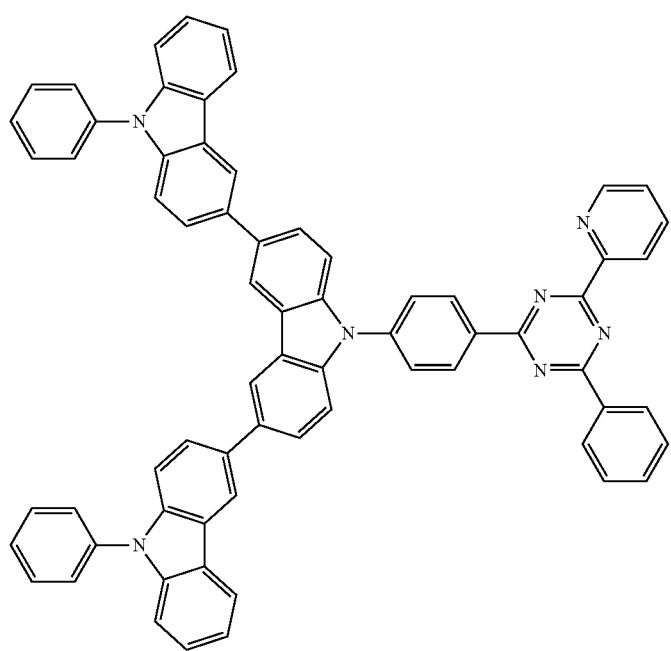
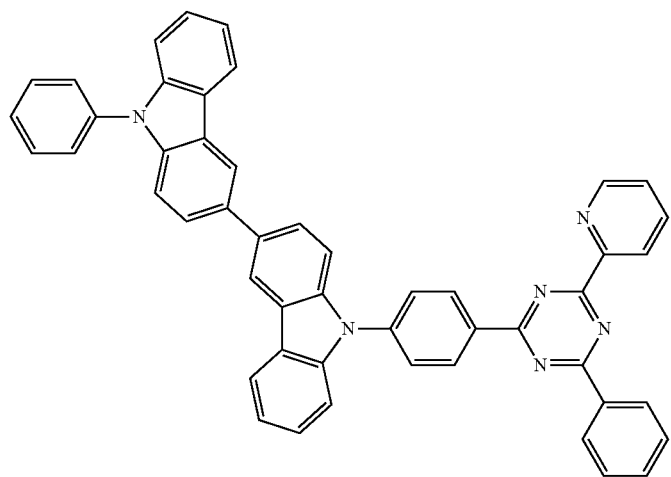

-continued
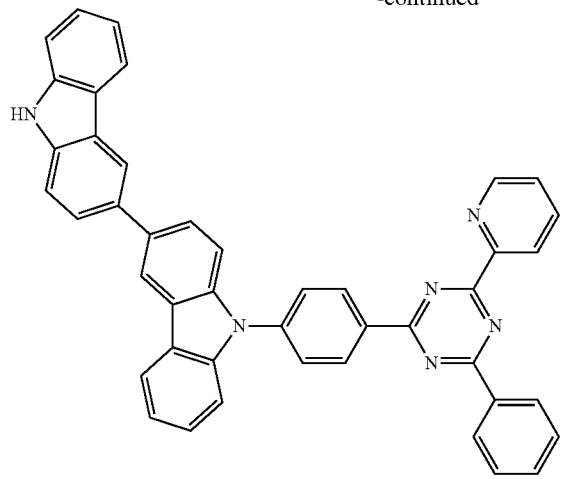
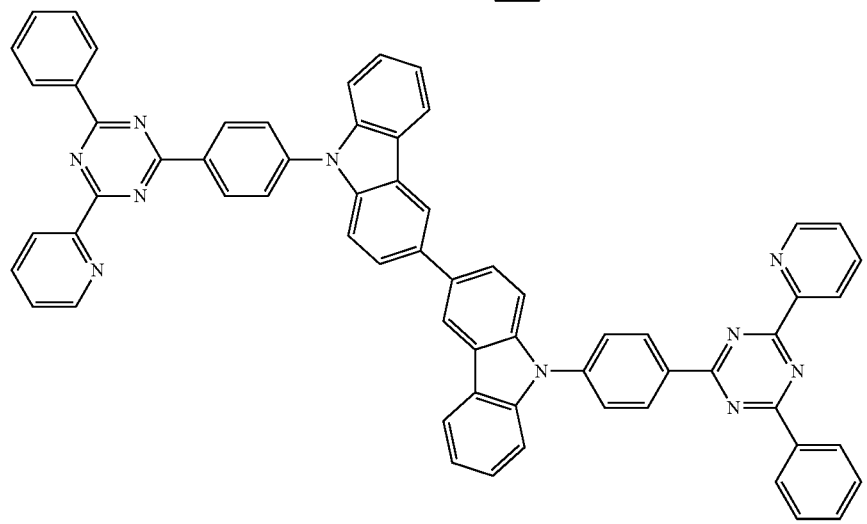
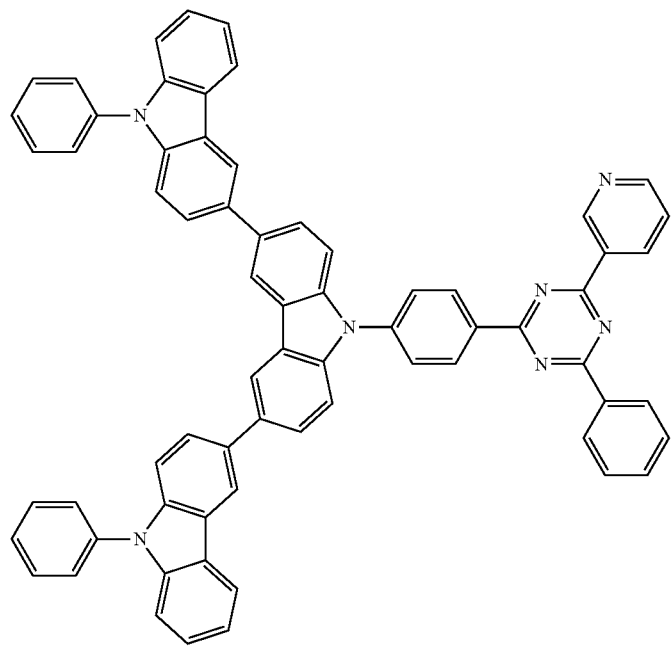

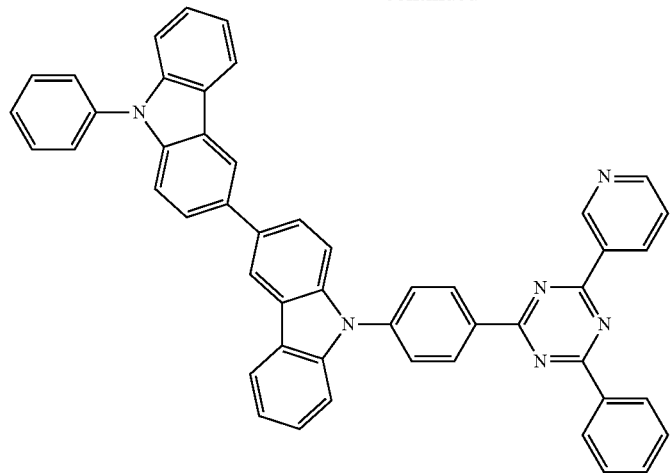
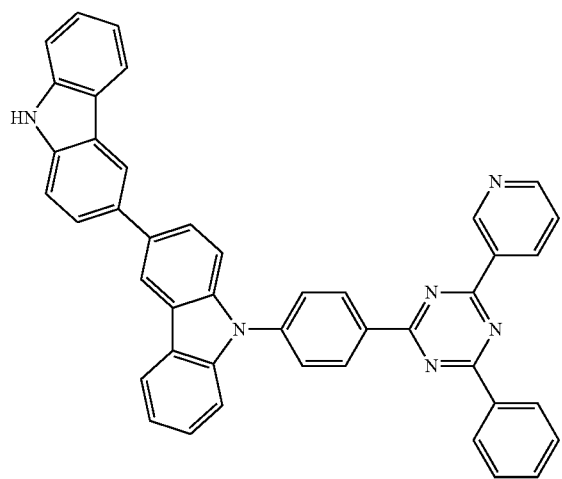
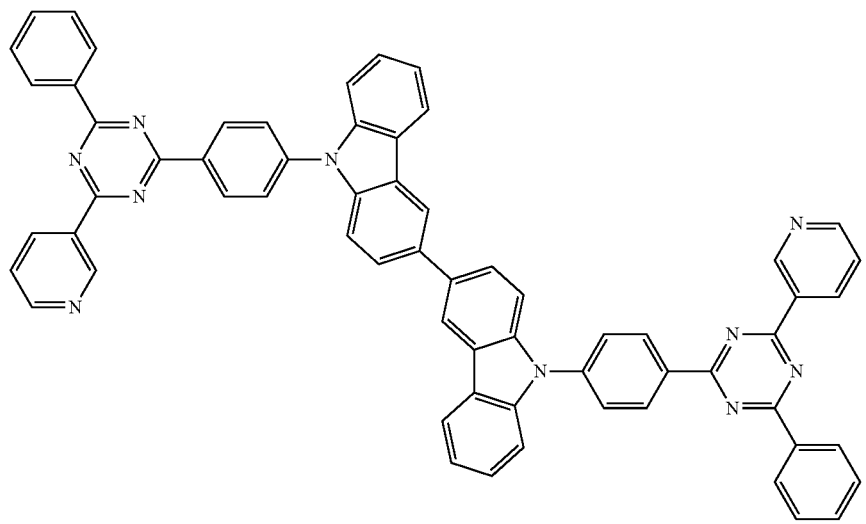

-continued
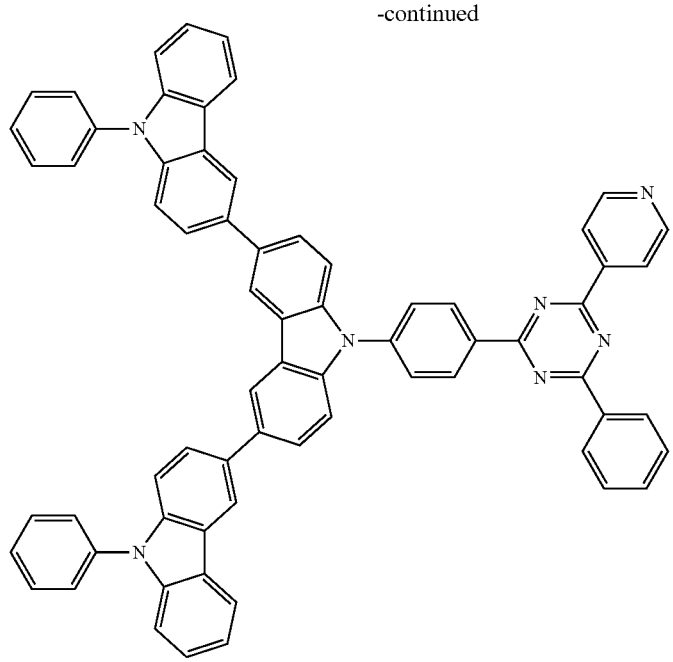
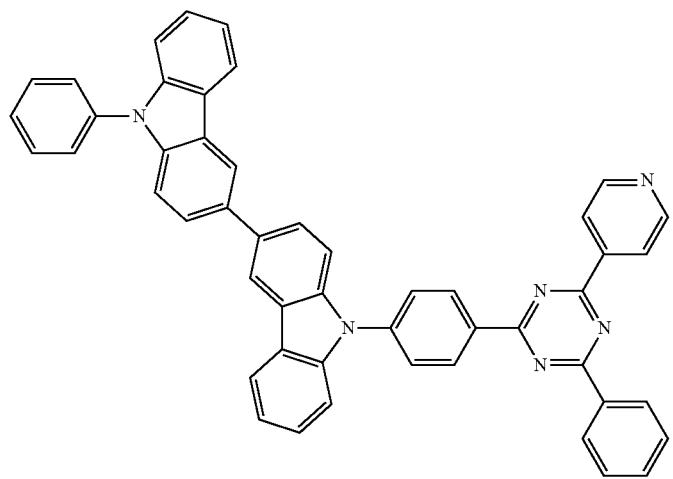
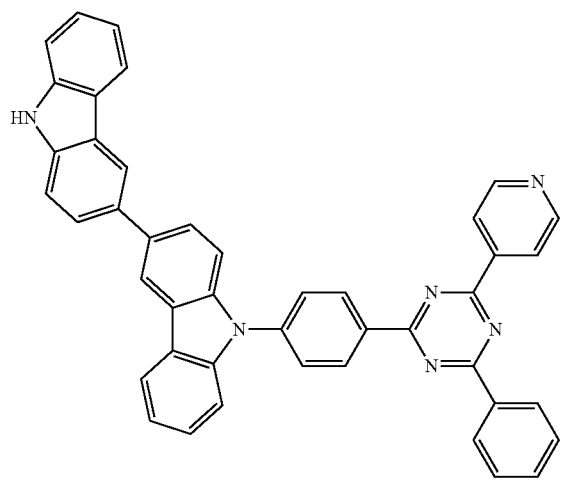

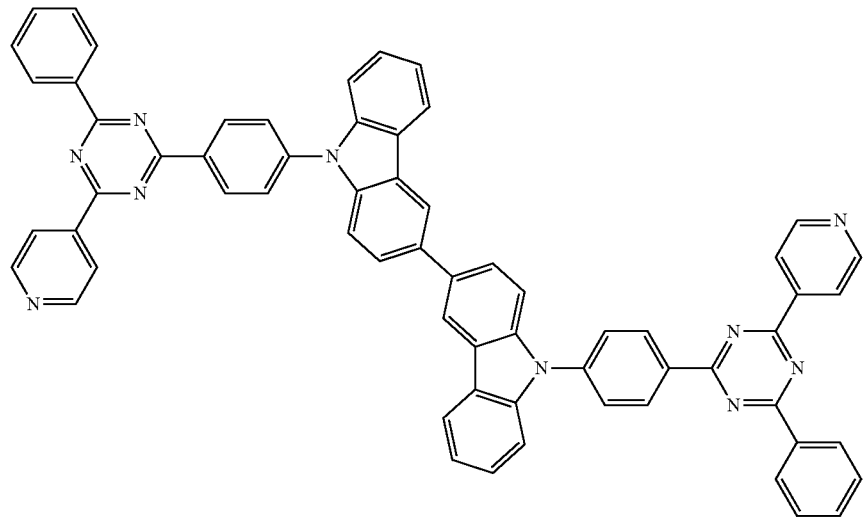
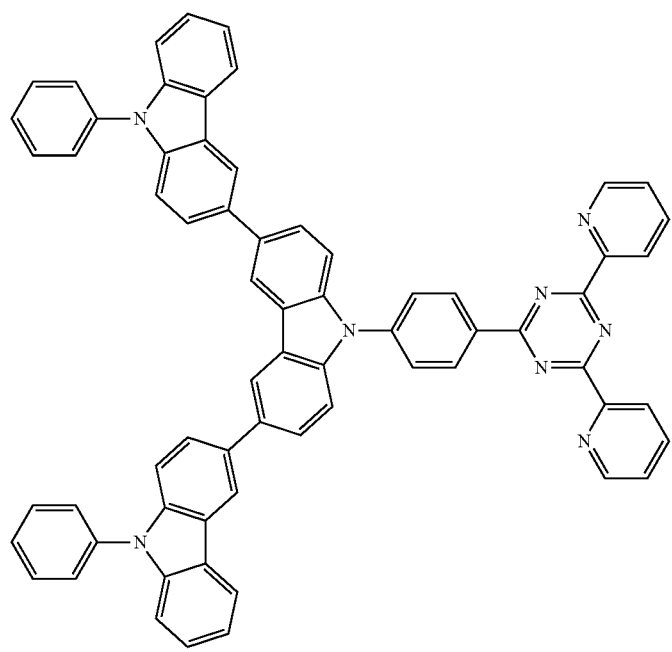
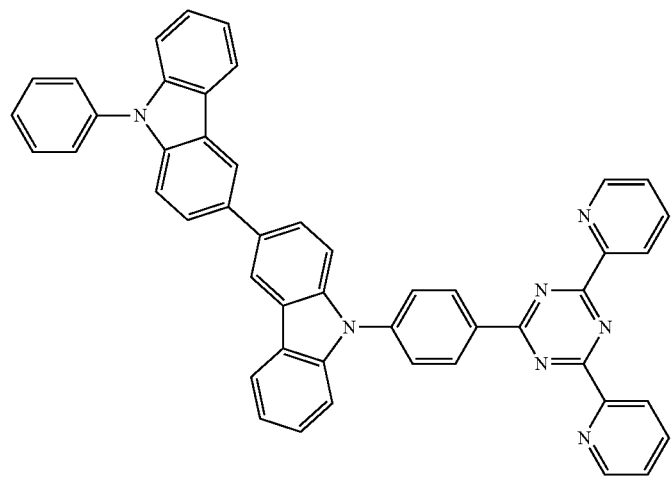

-continued
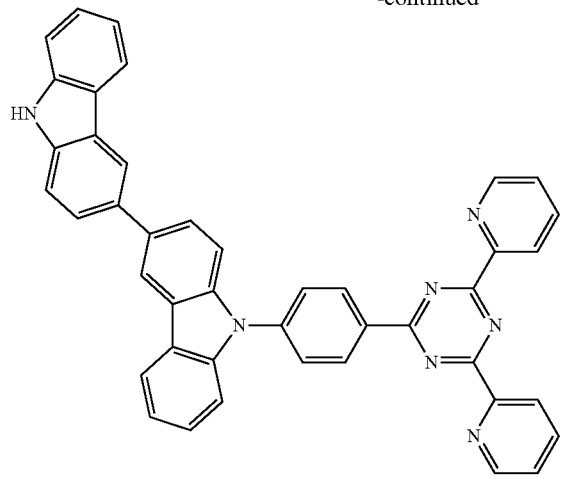
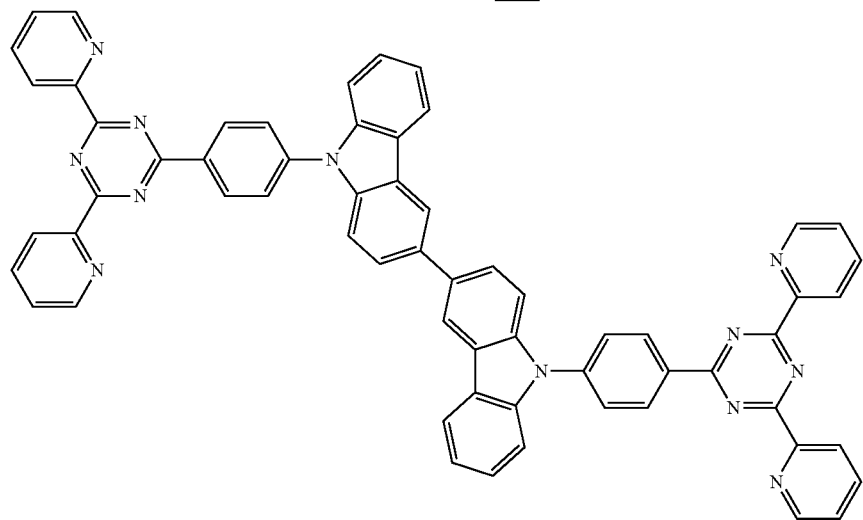
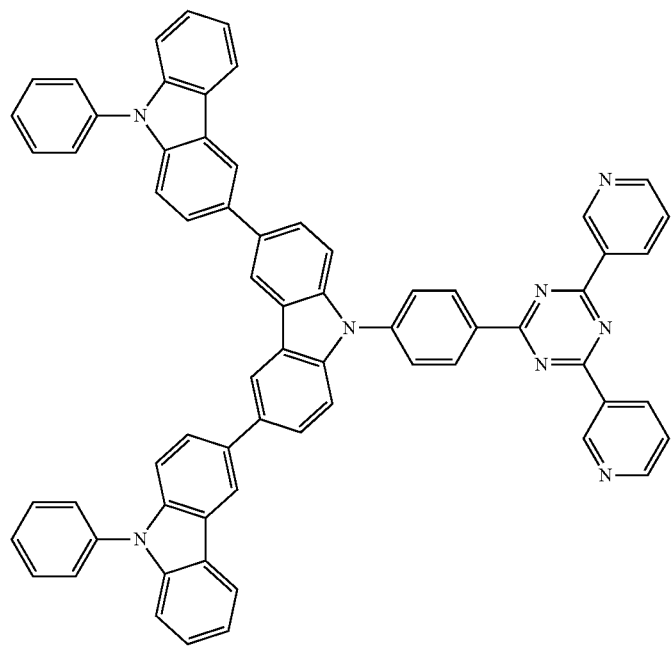

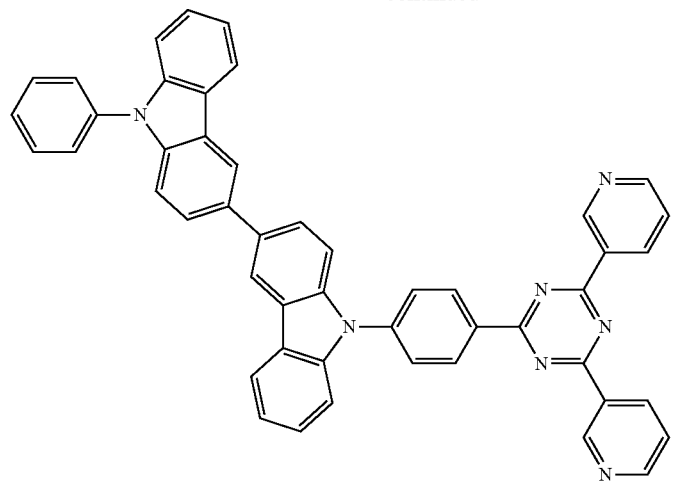
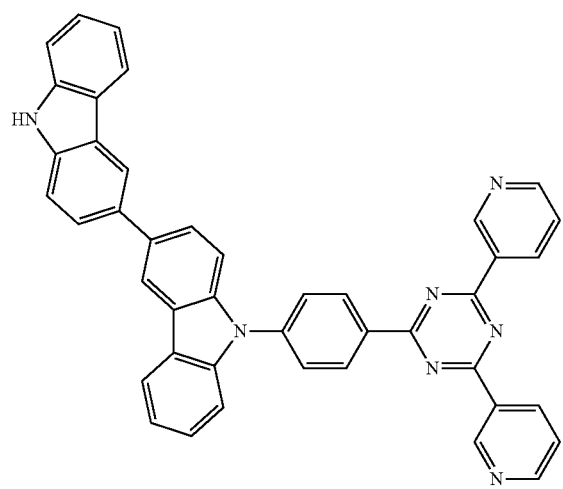
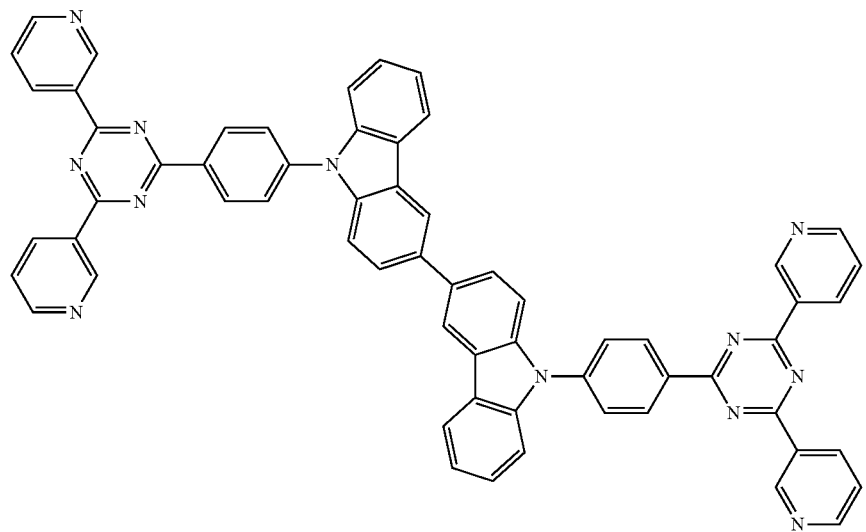

-continued
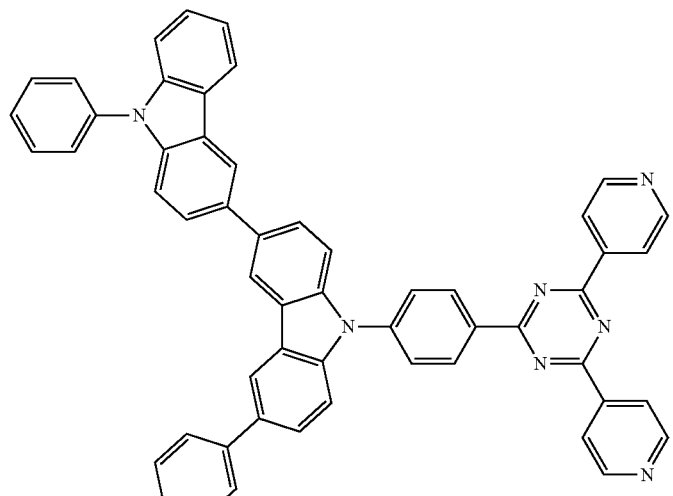
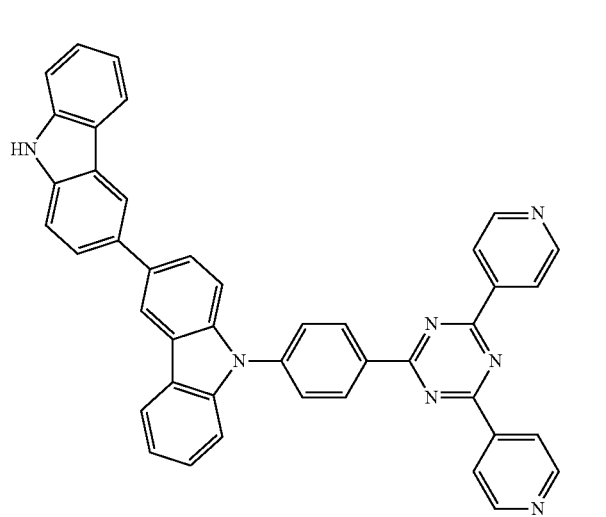

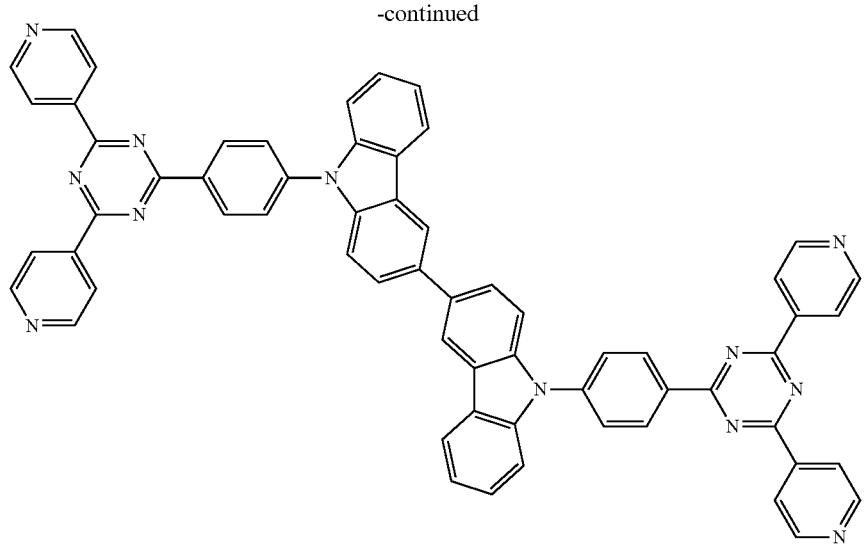
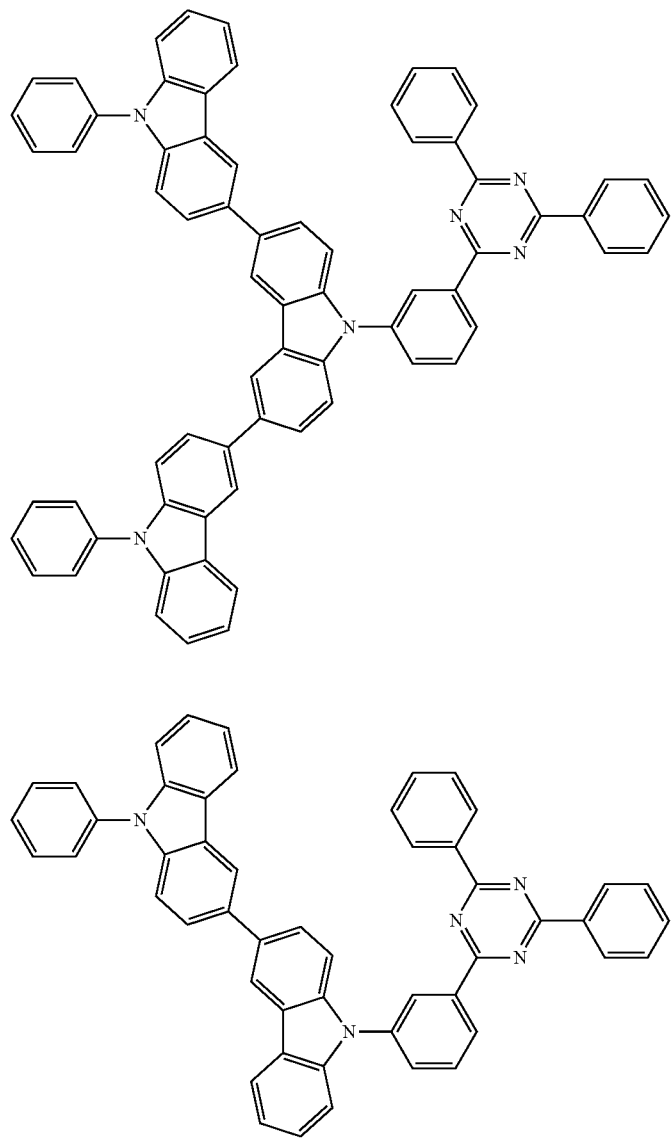

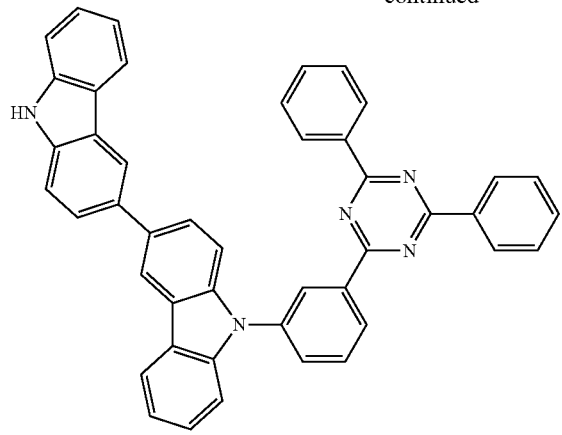
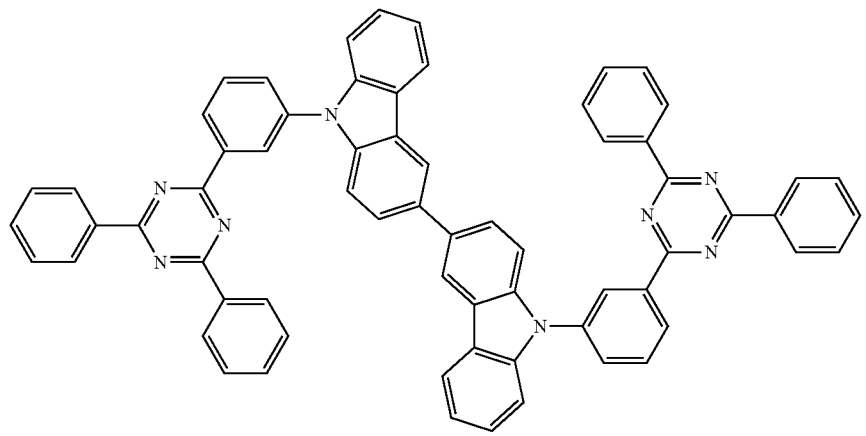
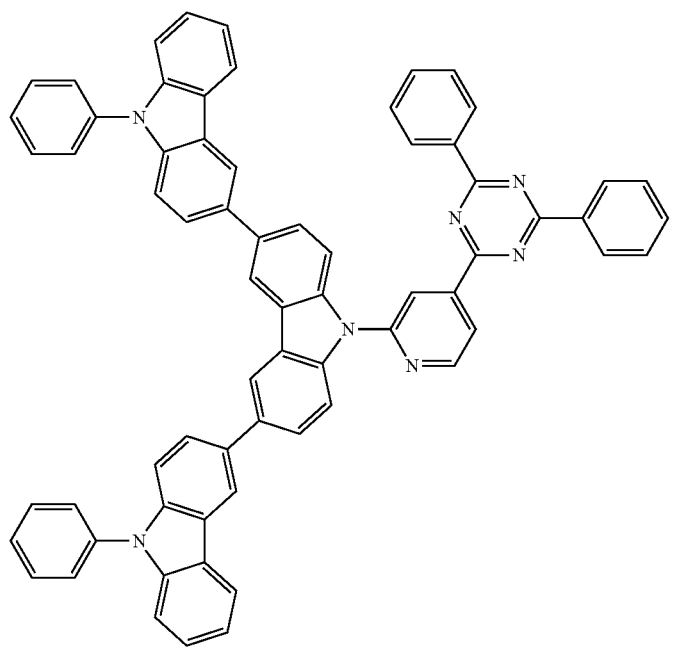

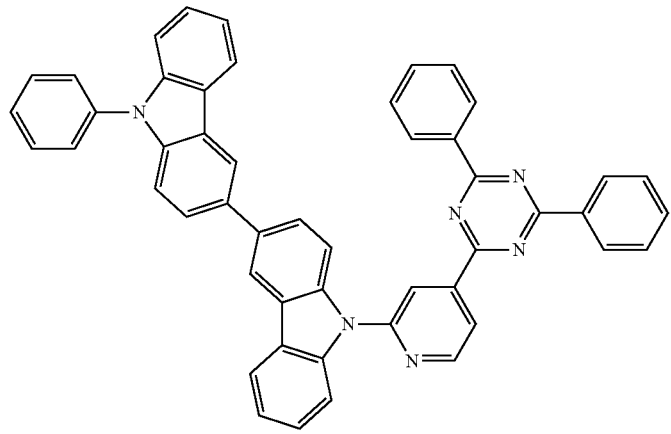
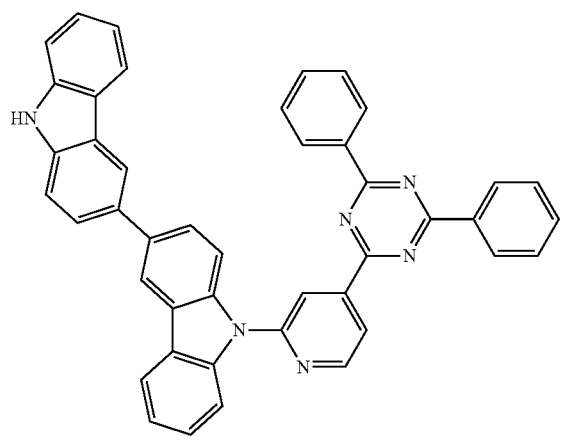
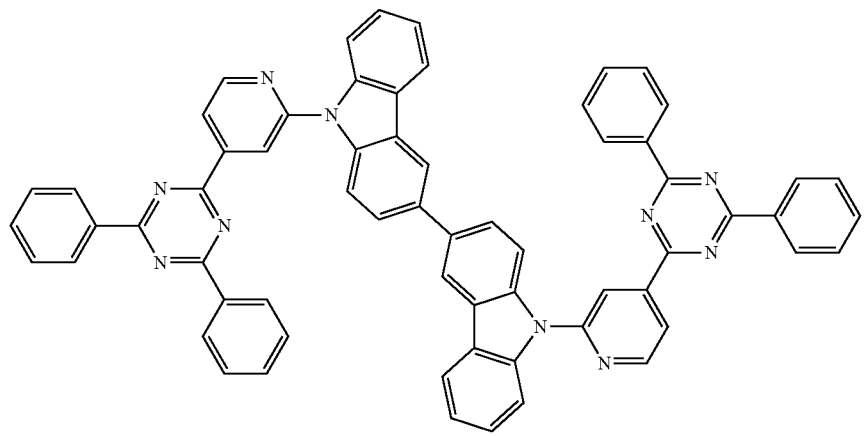

-continued
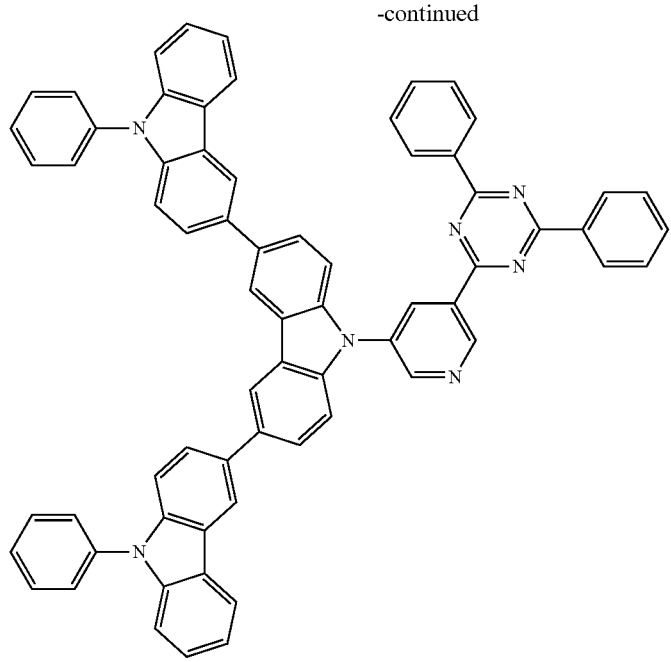
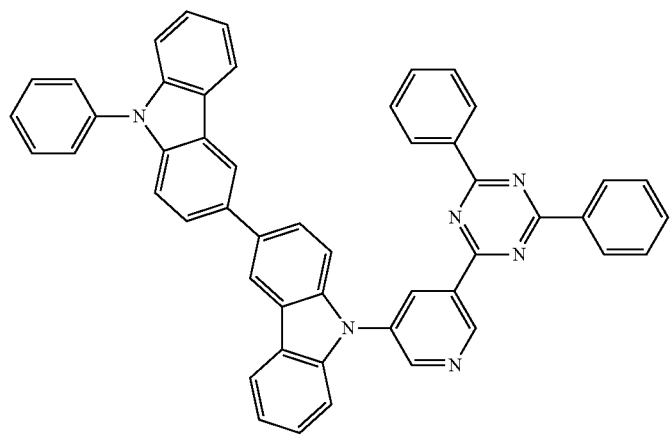
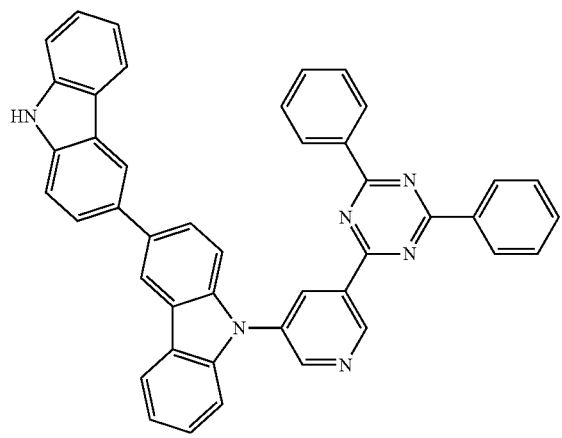

-continued
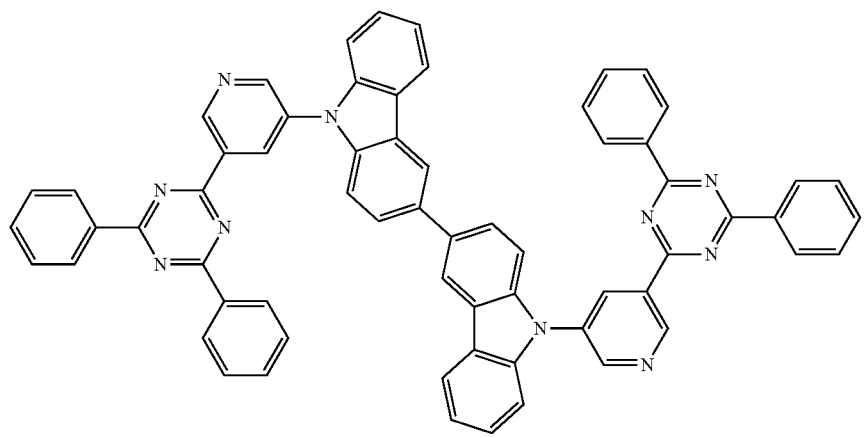
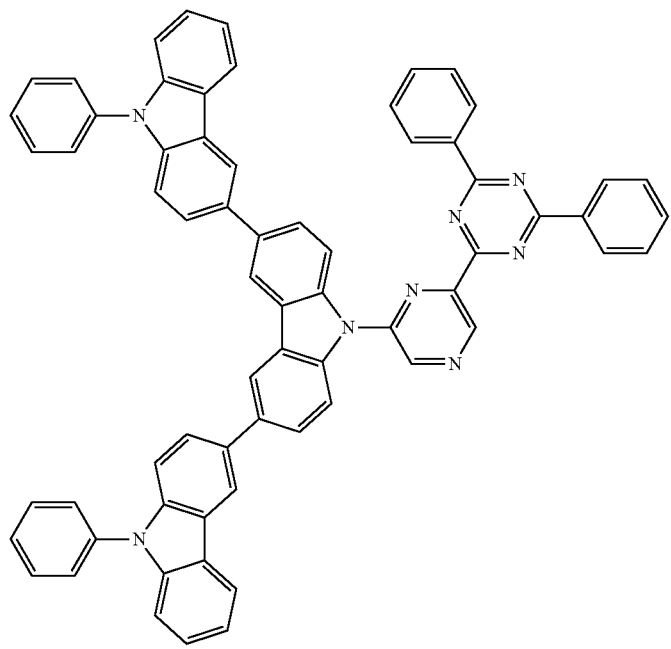
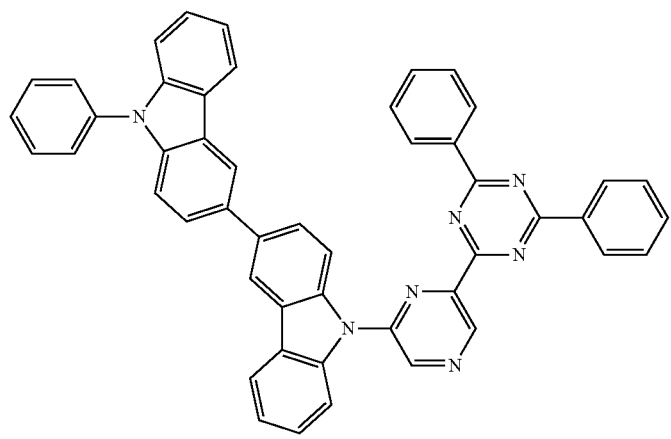

-continued
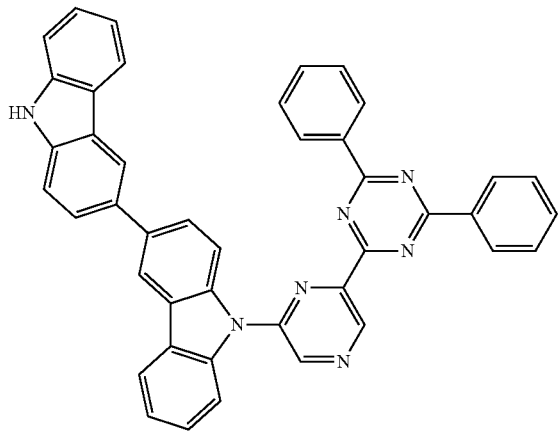
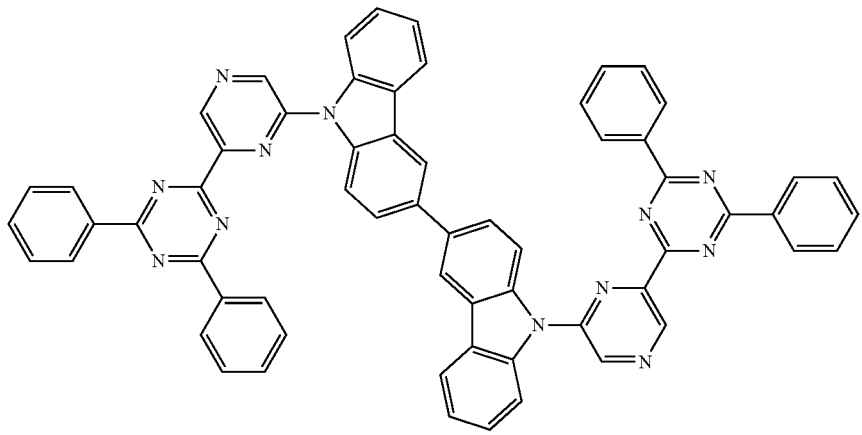
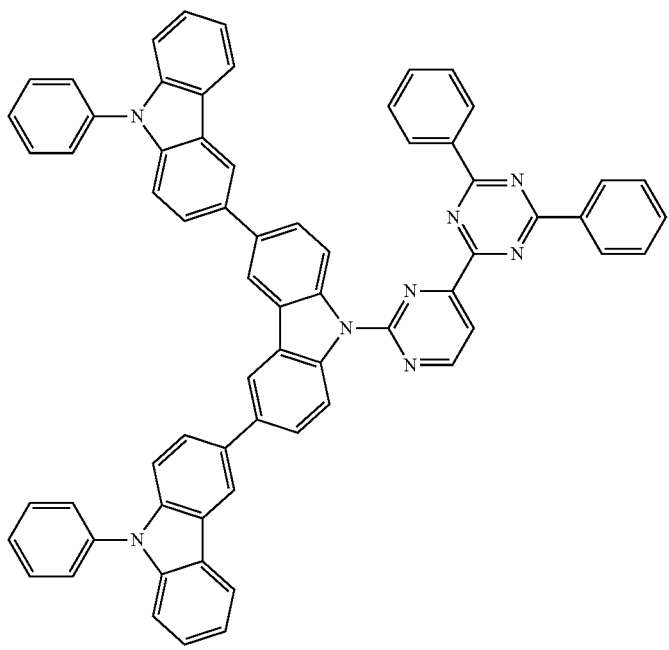

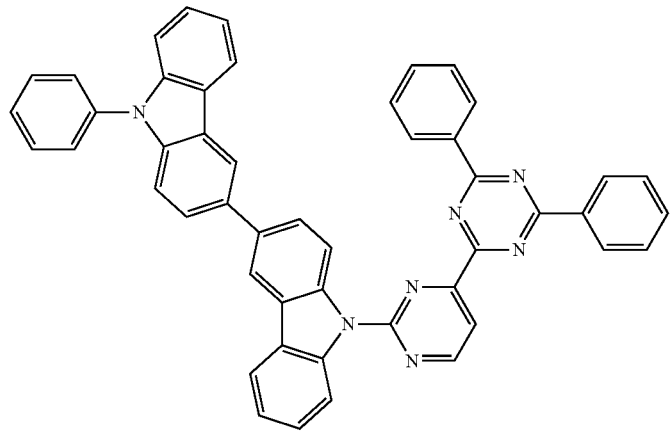
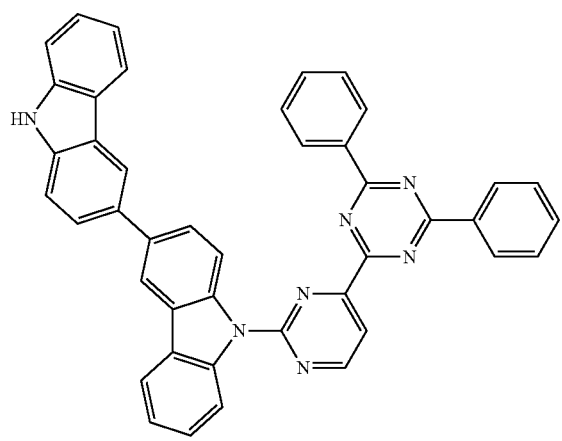
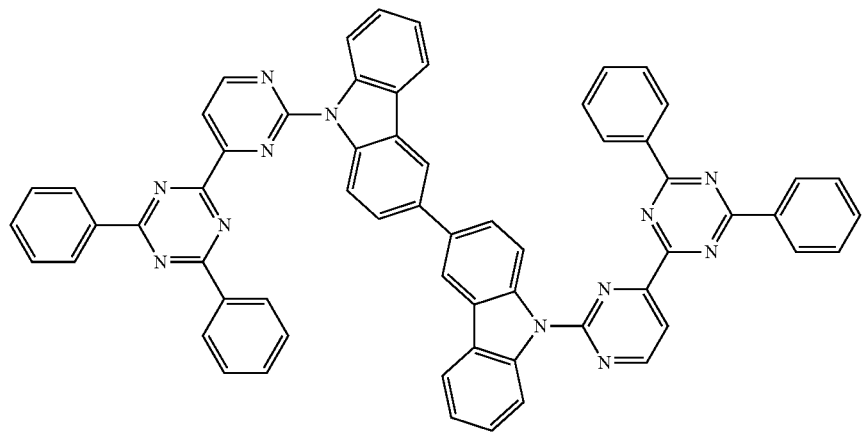

-continued
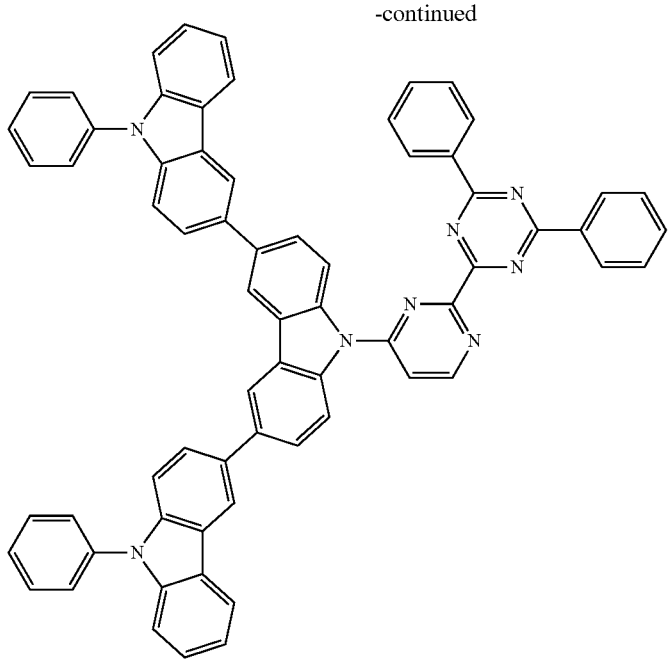
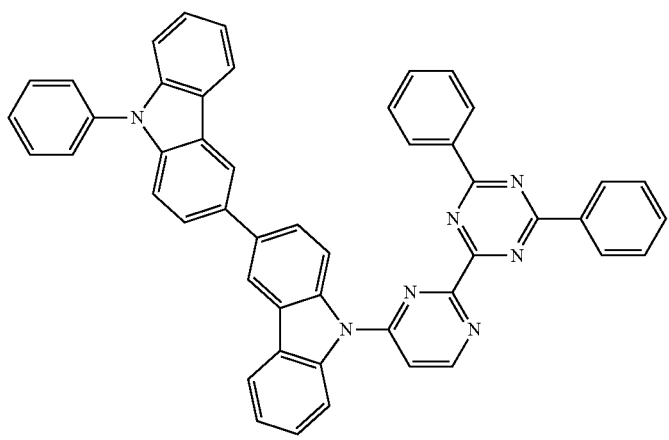
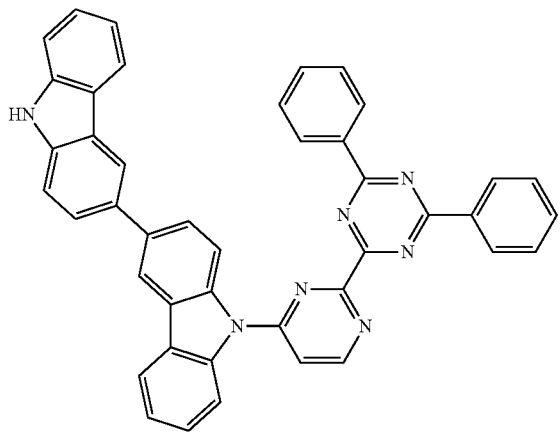

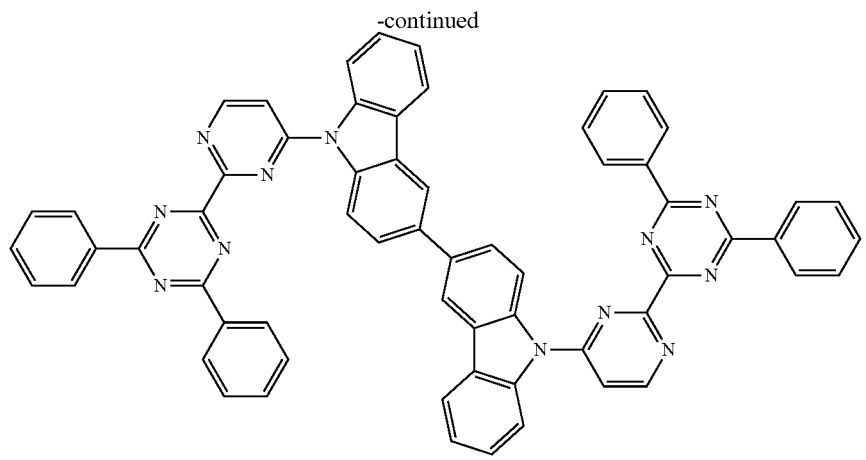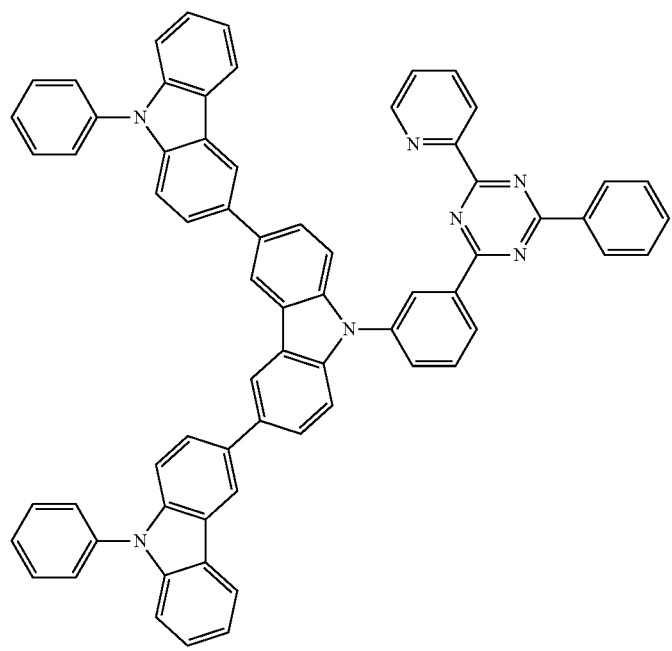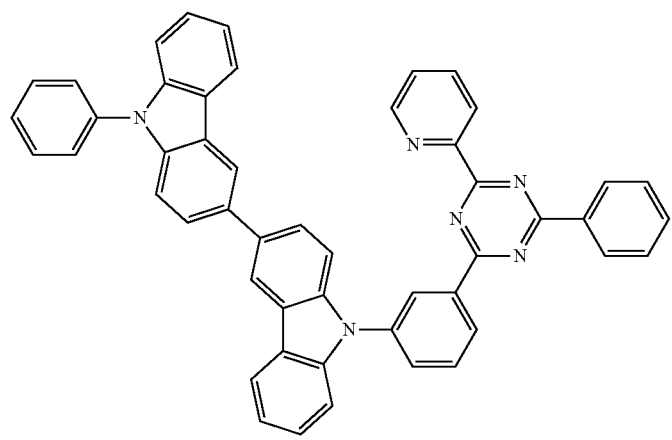

-continued
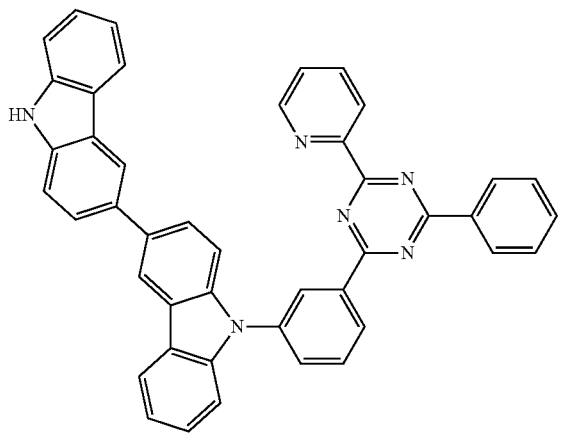
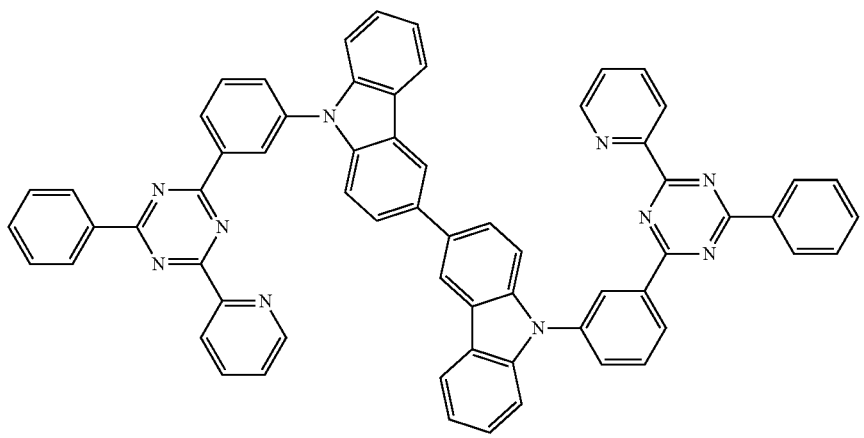
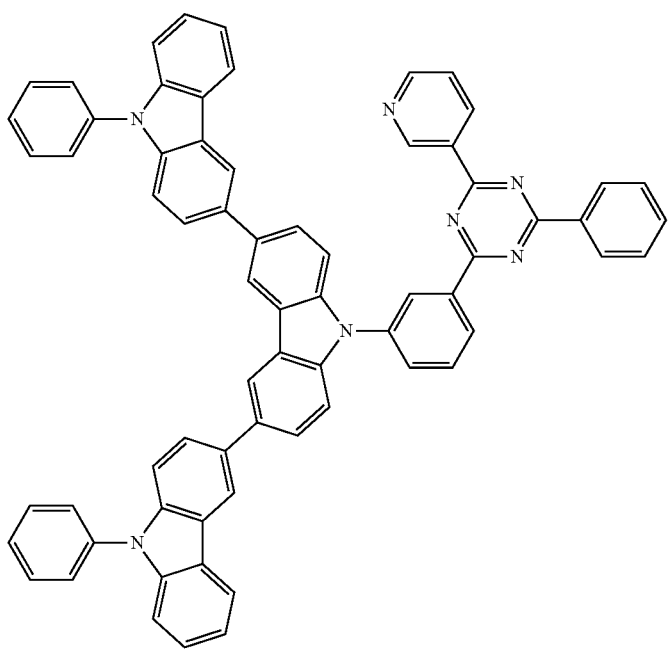

-continued
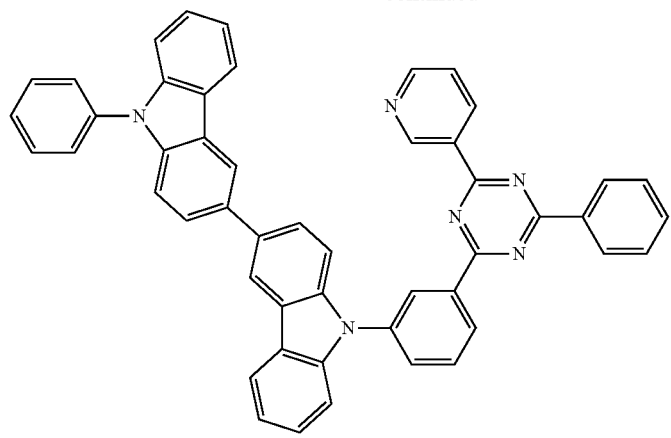
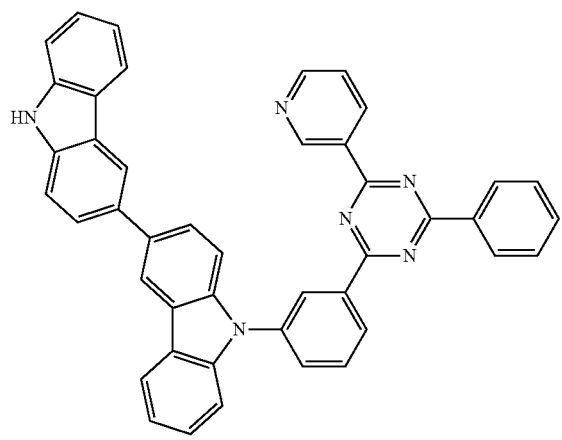
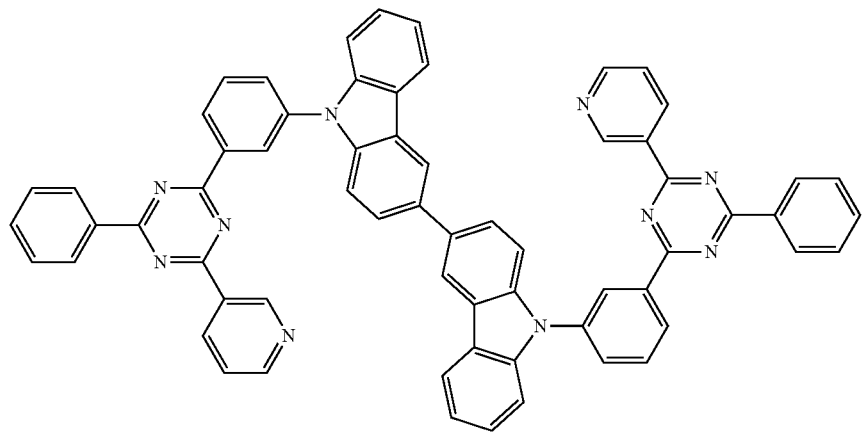

-continued
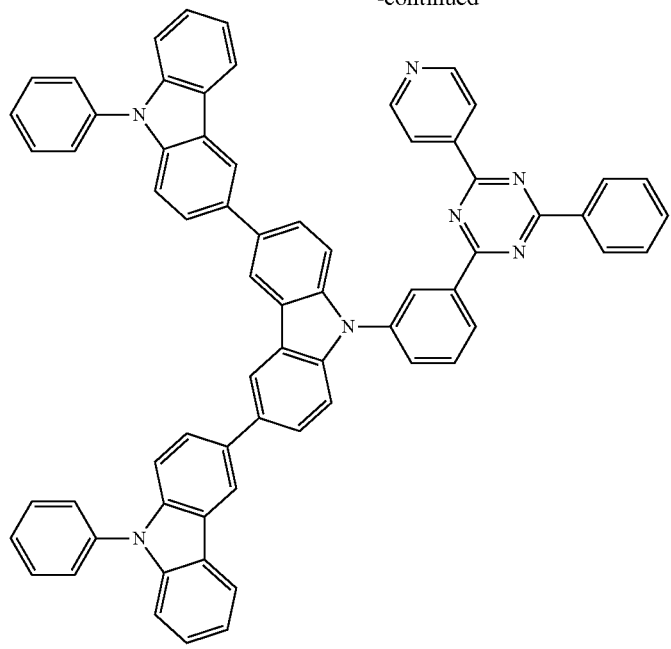
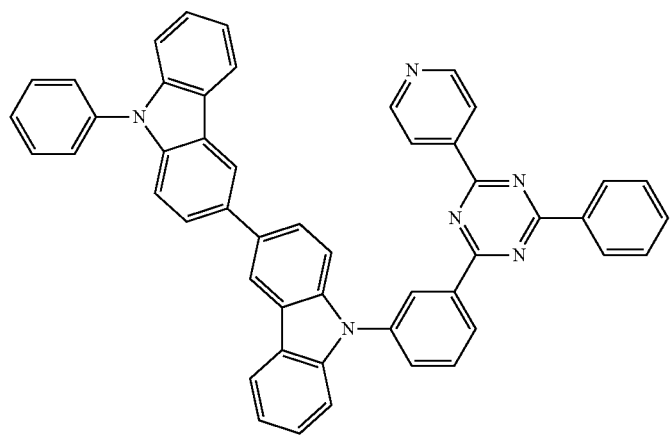
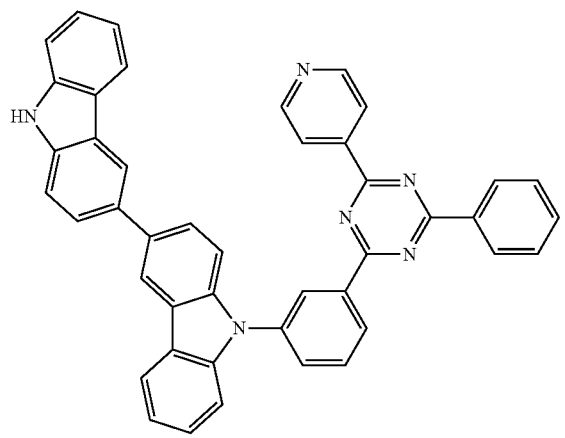

-continued
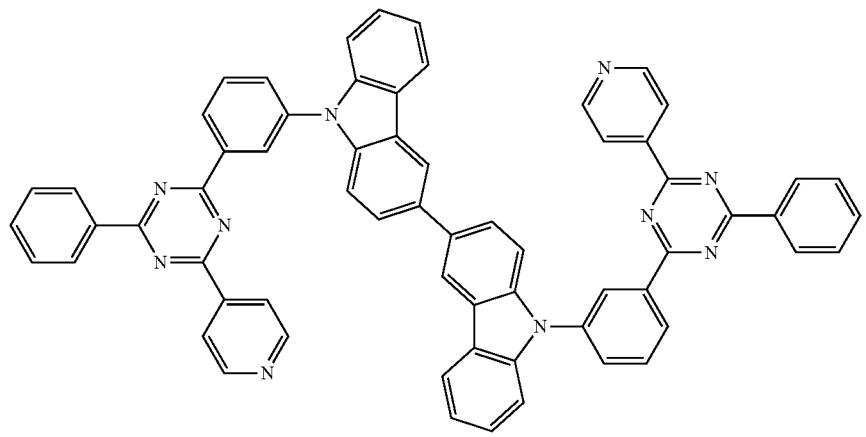
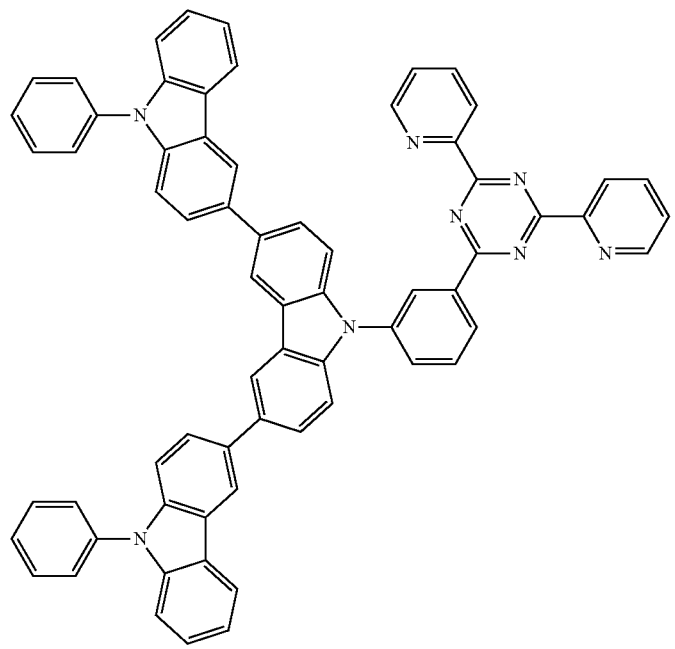
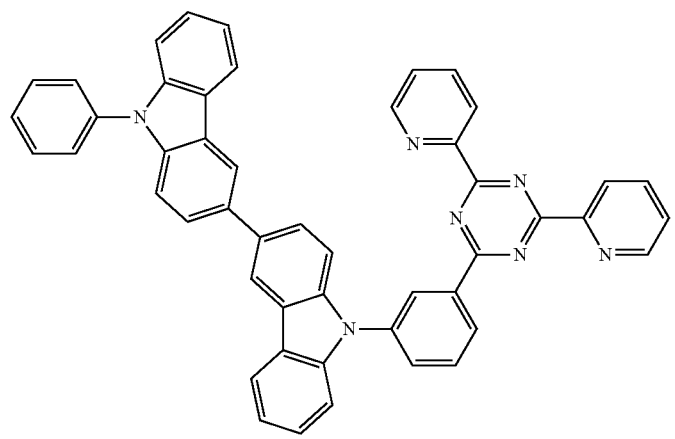

-continued
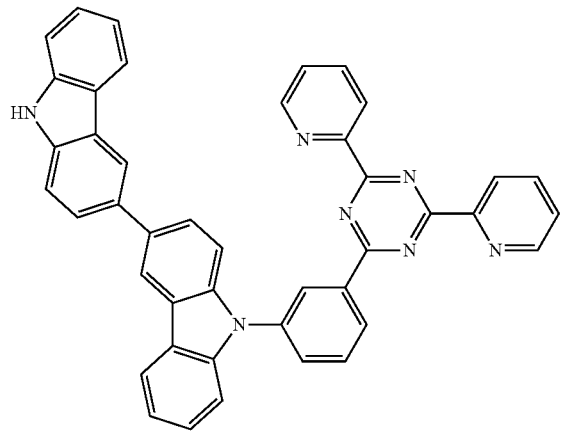
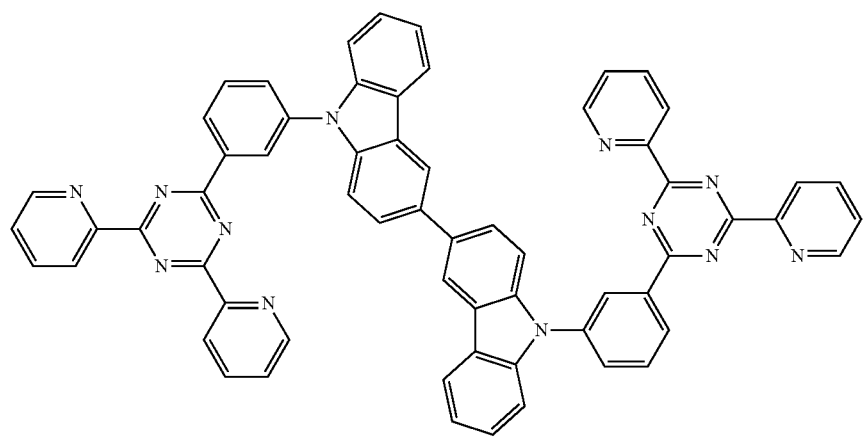
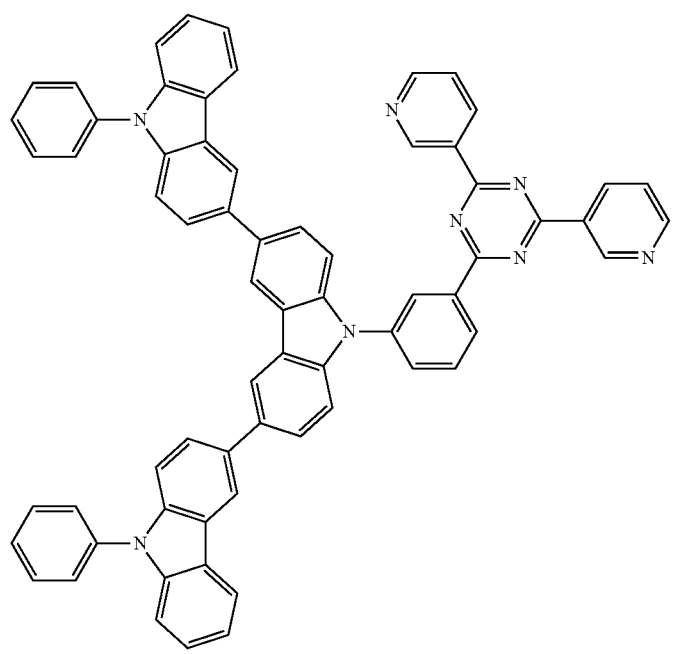

-continued
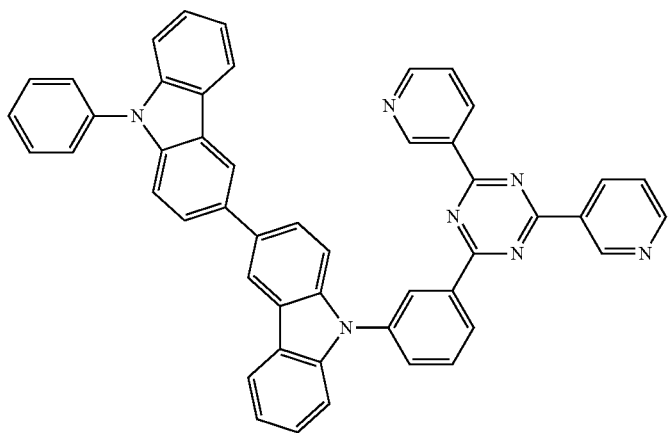
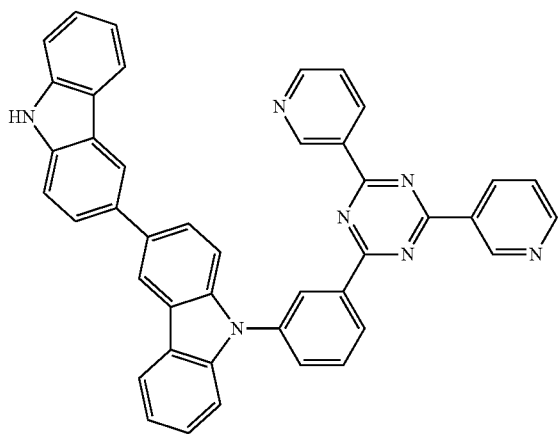
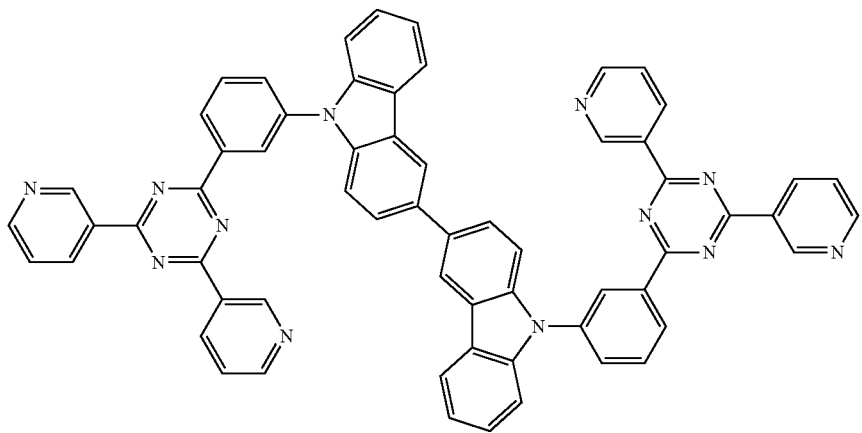

-continued
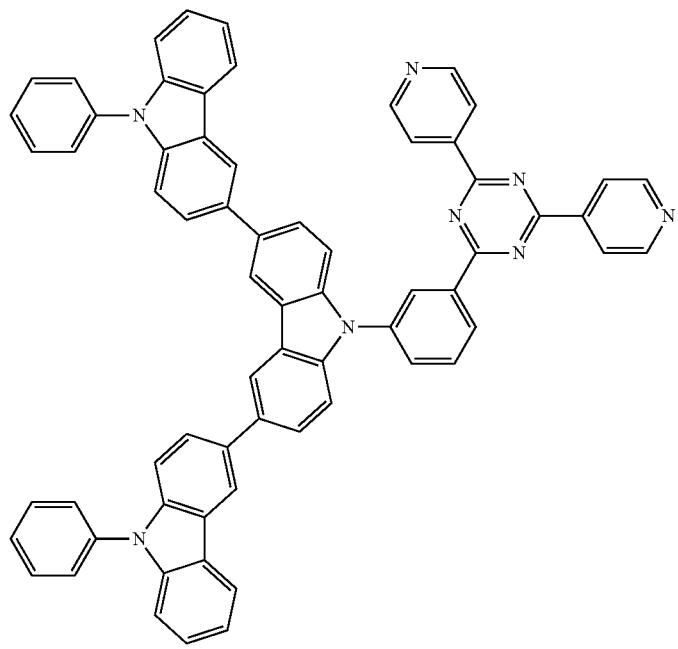
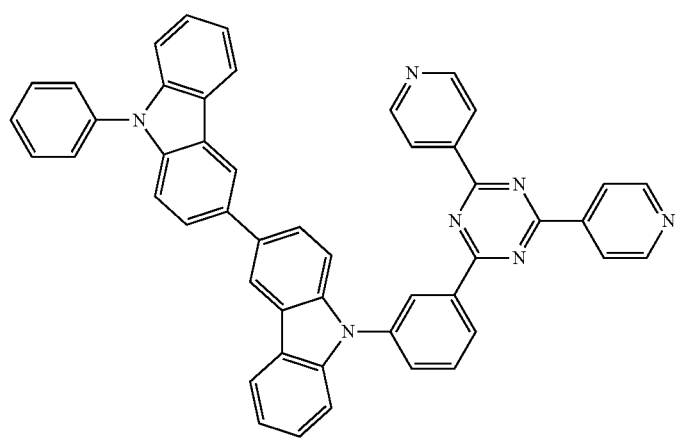
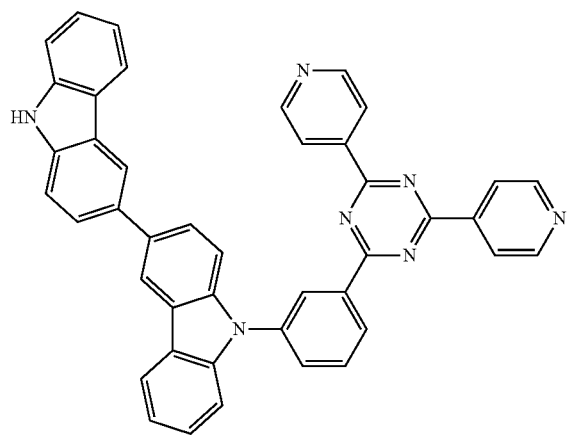

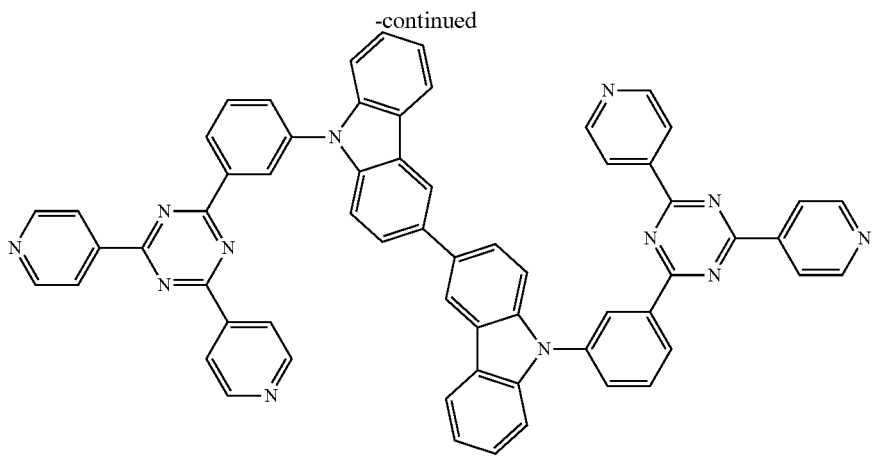

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light-emitting material.

For example, it may be considered that a polymerizable group is introduced in advance to the structure represented by the general formula (1), and a polymer obtained by polymerizing the polymerizable group is used as a light-emitting material. Specifically, it may be considered that a monomer that has a polymerizable functional group at any of $Ar^1$, $Ar^2$, $Ar^3$, and $R^1$ to $R^8$ in the general formula (1) is prepared, and is homopolymerized or copolymerized with another monomer to prepare a polymer containing repeating units, and the polymer is used as a light-emitting material. In alternative, it may be considered that the compounds containing a structure represented by the general formula (1) are reacted to form a dimer or a trimer, and the dimer or the trimer is used as a light-emitting material.

Examples of the polymer having the repeating unit containing the structure represented by the general formula (1) include a polymer containing a structure represented by the following general formula (2) or (3).

General Formula (2)

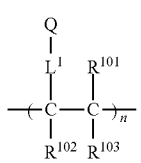

General Formula (3)

$$-\!\!\left(\!\!\begin{array}{c}Q\\|\\L^2\\|\\C=C\\|\\R^{104}\end{array}\!\!\right)_{\!\!n}\!\!-$$

In the general formulae (2) and (3), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}$-$L^{11}$-, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (2) and (3), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $Ar^1$, $Ar^2$, $Ar^3$, and $R^1$ to $R^8$ of the structure of the general formula (1) constituting Q. Two or more of the linking groups may be boded to one group represented by Q to form a crosslinked structure or a network structure.

Specific examples of the structure of the repeating unit include structures represented by the following formulae (4) to (7).

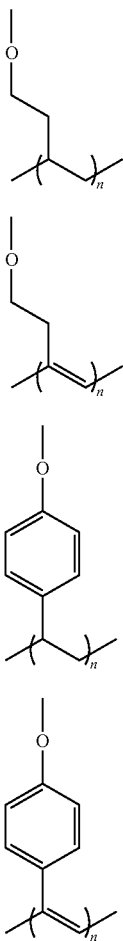

Formula (4)

Formula (5)

Formula (6)

Formula (7)

The polymer having the repeating unit containing the structure represented by any of the formulae (4) to (7) may be synthesized in such a manner that a hydroxyl group is introduced to any of $Ar^1$, $Ar^2$, $Ar^3$, and $R^1$ to $R^8$ of the general formula (1), and the hydroxyl group as a linker is reacted with the following compound to introduce a polymerizable group thereto, followed by polymerizing the polymerizable group.

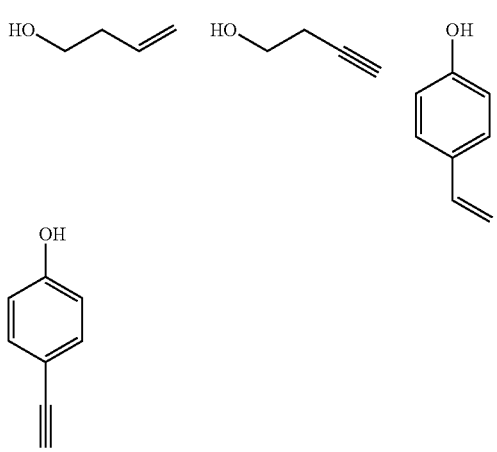

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound represented by General Formula (1')

In the compound represented by the general formula (1), a compound represented by the following general formula (1') is a novel compound.

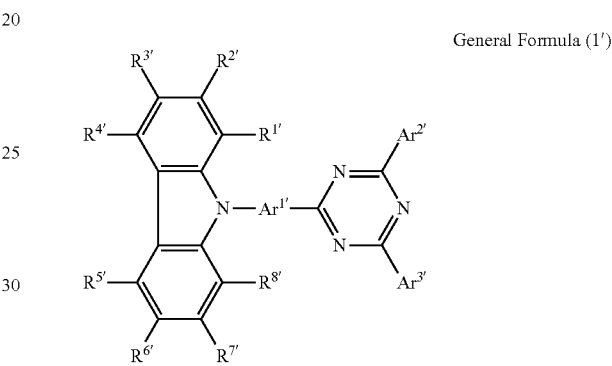

General Formula (1')

In the general formula (1'), $R^{1'}$ to $R^{8'}$ each independently represent a hydrogen atom or a substituent, provided that at least one of $R^{1'}$ to $R^{8'}$ represents a substituted or unsubstituted 1-carbazolyl group, a substituted or unsubstituted 2-carbazolyl group, a substituted or unsubstituted 3-carbazolyl group, or a substituted or unsubstituted 4-carbazolyl group, provided that the 9-position of the carbazolyl groups is unsubstituted; and $Ar^{1'}$ to $Ar^{3'}$ each independently represent a substituted or unsubstituted aromatic ring or heteroaromatic ring.

For the substituent that may be represented by $R^{1'}$ to $R^{8'}$ and the substituent that the carbazolyl group has in the general formula (1'), reference may be made to the descriptions and the preferred ranges of the substituent that may be represented by $R^1$ to $R^8$ and the substituent that the carbazolyl group has in the general formula (1).

For the descriptions and the preferred ranges of $Ar^{1'}$ to $Ar^{3'}$ in the general formula (1'), reference may be made to the descriptions and the preferred ranges of $Ar^1$ to $Ar^3$ in the general formula (1).

In the general formula (1'), at least one of $R^{1'}$ to $R^{8'}$ preferably represents a substituted or unsubstituted 3-carbazolyl group.

The compound represented by the general formula (1') may be synthesized by combining the known synthesis reactions. For example, the compound represented by the general formula (1') may be synthesized according to the following reaction. In the reaction, X represents a halogen atom, and preferably a fluorine atom, a chlorine atom, a bromine atom, or an iodine atom, and for example, a bromine atom may be used. For the detailed reaction conditions, reference may be made to the synthesis examples described later.

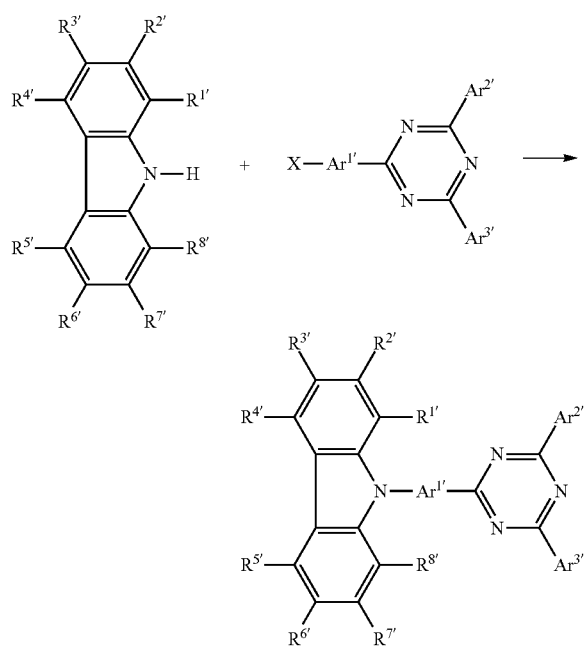

The compound represented by the general formula (1), which encompasses the compound represented by the general formula (1'), may also be synthesized by combining the known methods, and may also be synthesized by appropriately applying the methods described in the aforementioned known literatures (WO 2011/132683 and WO 2012/077902), and the like.

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) includes a delayed fluorescent material emitting delayed fluorescent light. Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent emitter emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent emitter is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). At this time, the compound represented by the general formula (1) of the invention may have a function of assisting light emission of another light-emitting material contained in the light-emitting layer, i.e., as a so-called assist dopant. Specifically, the compound represented by the general formula (1) of the invention contained in the light-emitting layer may have a lowest excited singlet energy level that is between the lowest excited singlet energy level of the host material contained in the light-emitting layer and the lowest excited singlet energy level of the another light-emitting material contained in the light-emitting layer.

The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layers in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof which may be used include those formed of glass, transparent plastics, quartz and silicon.

Anode

The anode of the organic electroluminescent device used is preferably formed of, as an electrode material, a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of, as an electrode material, a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers is not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R, R', and $R_1$ to $R_{10}$ each independently represent a hydrogen atom or a substituent, and n represents an integer of from 3 to 5.

Preferred examples of a compound that may also be used as the host material of the light-emitting layer are shown below.

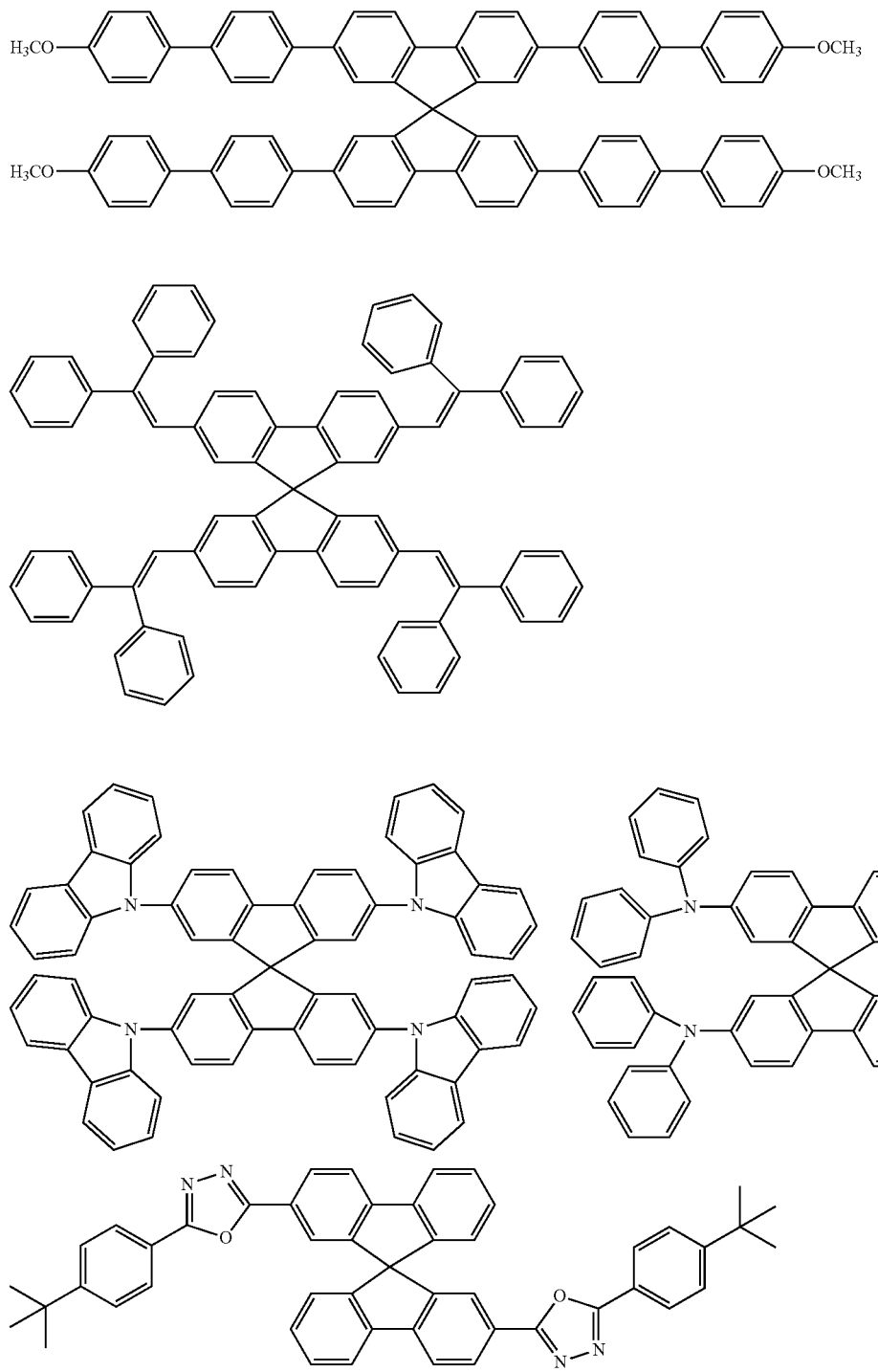

-continued
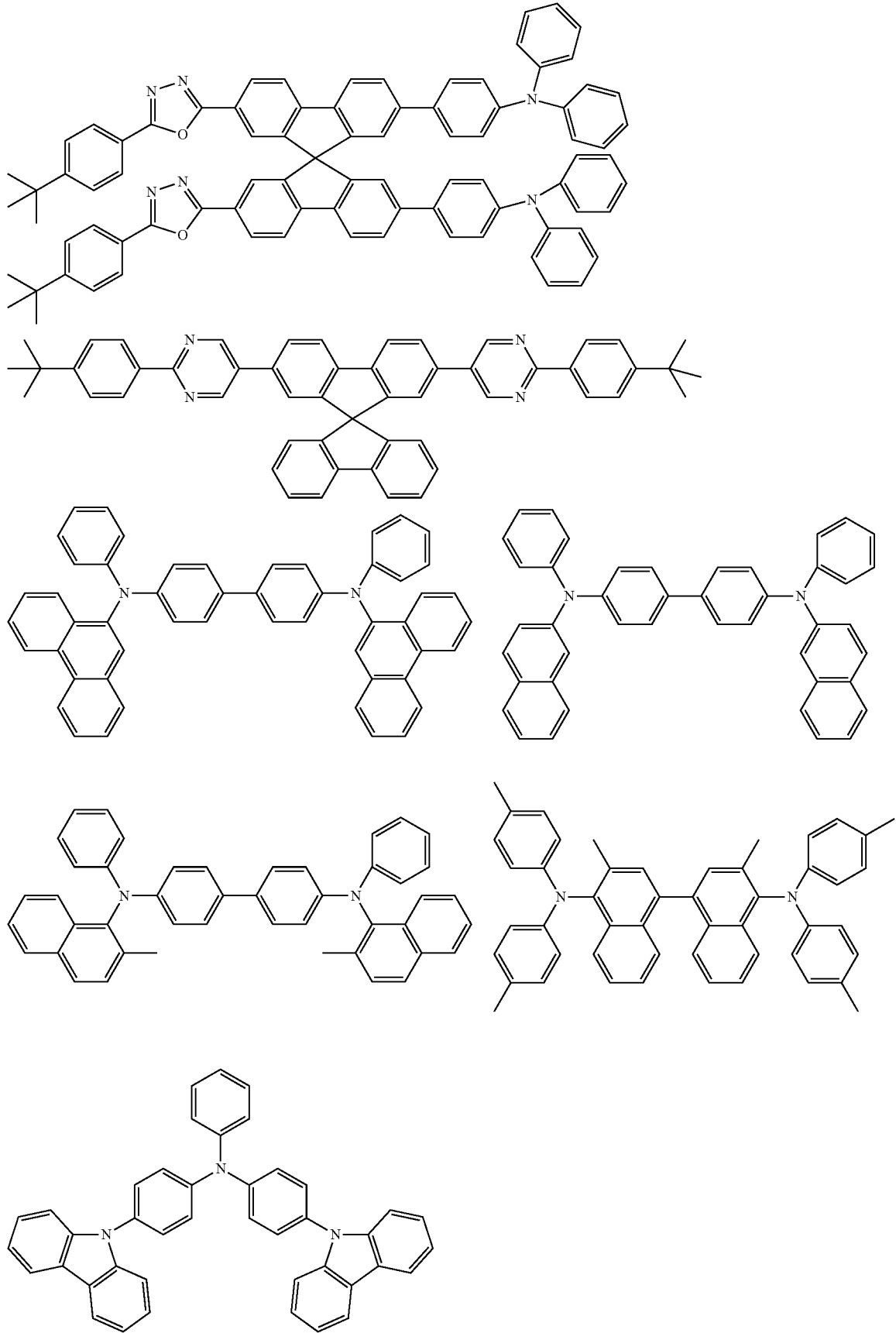

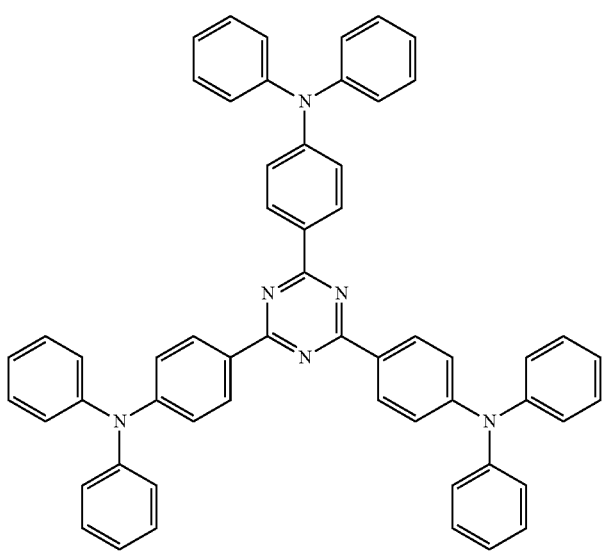
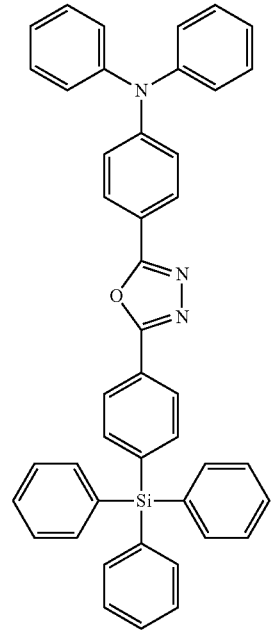
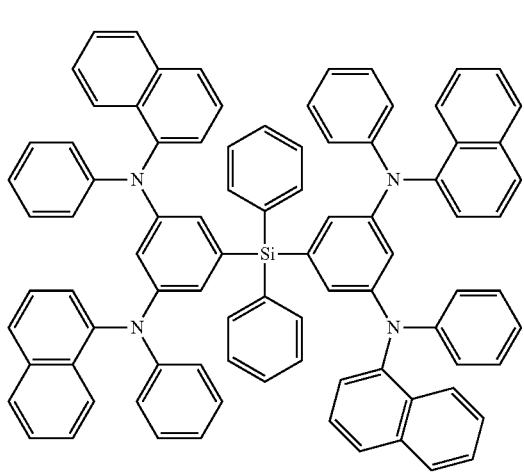
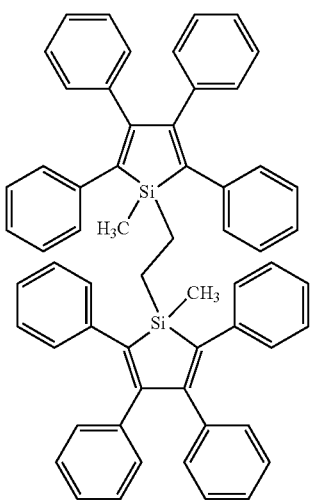
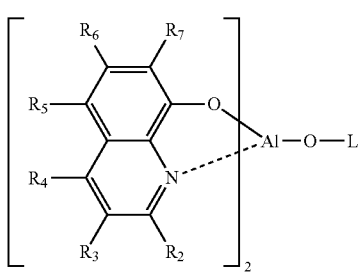
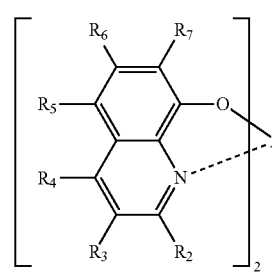
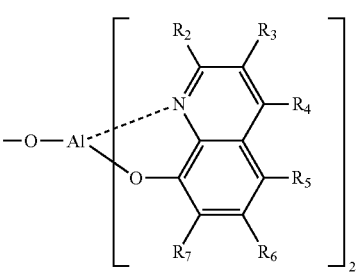
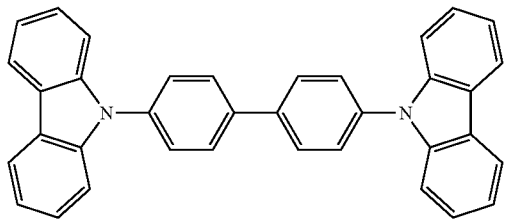
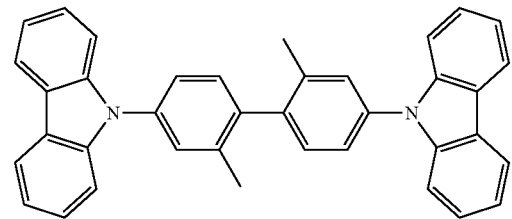

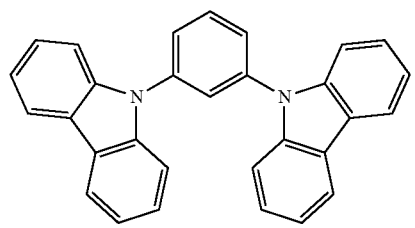
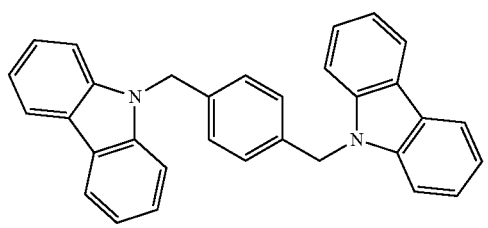
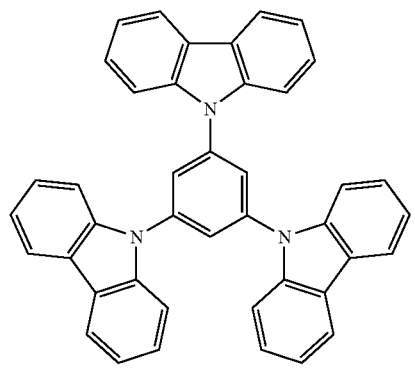
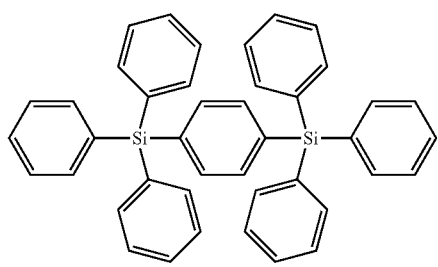
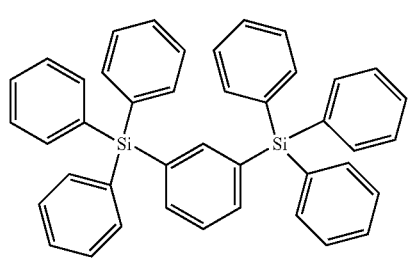
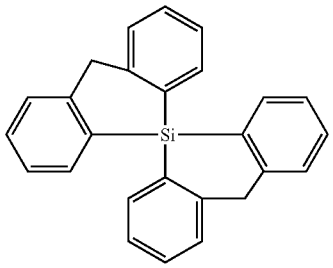
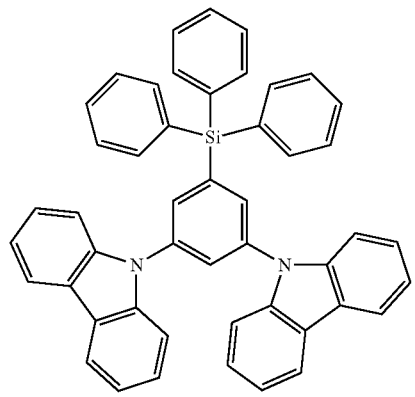
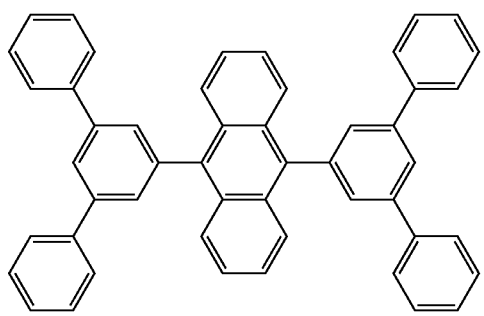
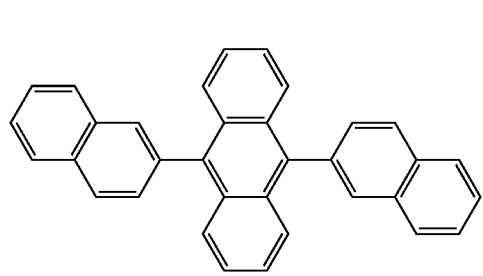
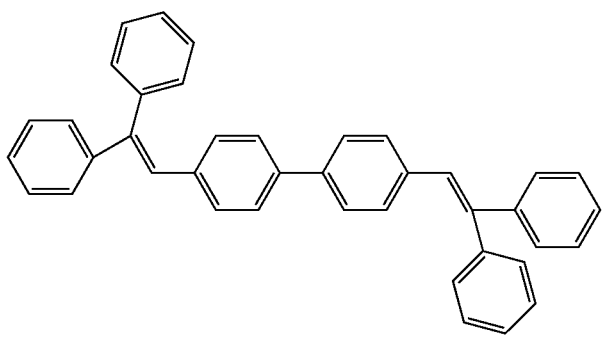

-continued
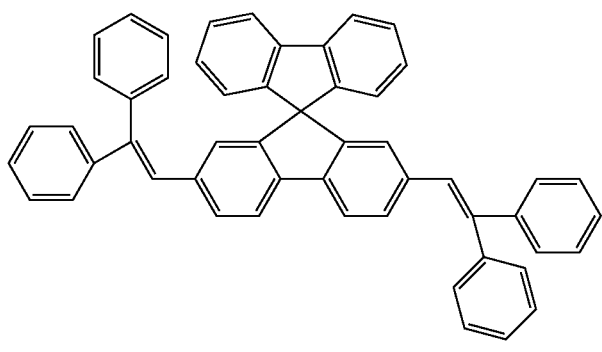
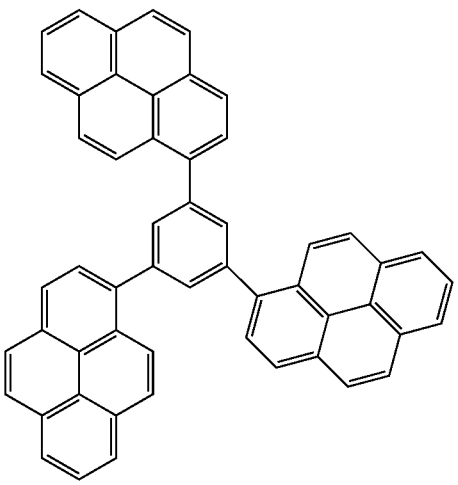
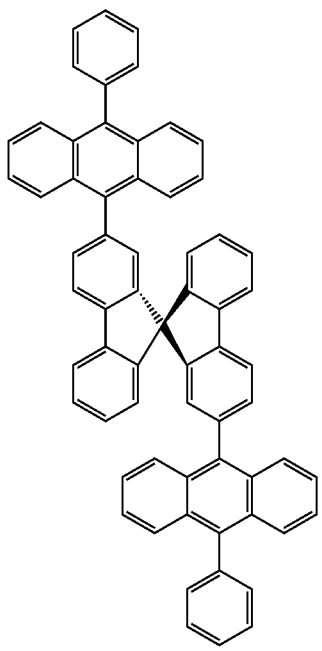
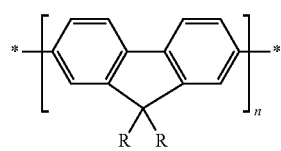
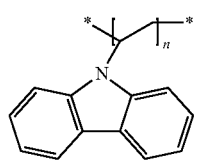
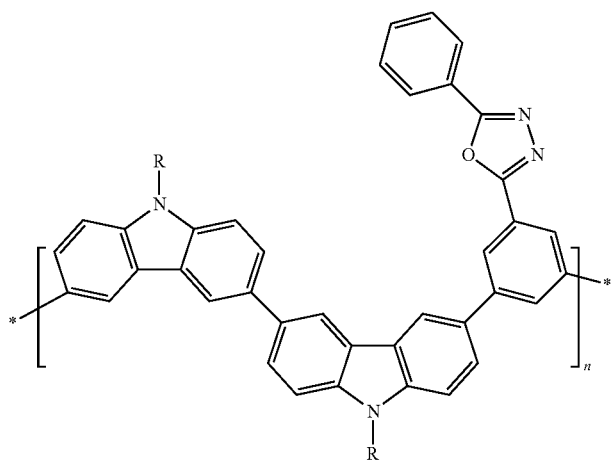
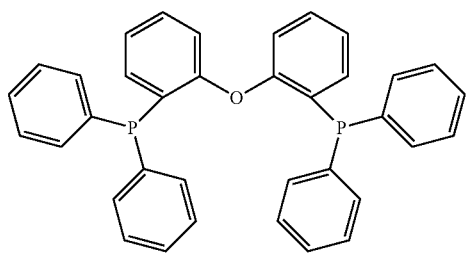

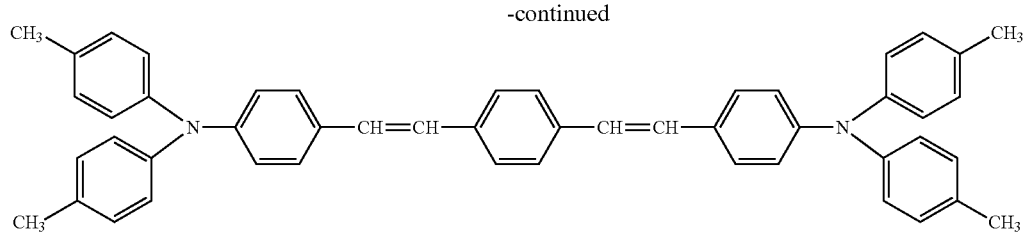
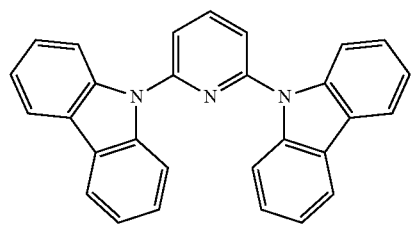
Preferred examples of a compound that may be used as the hole injection material are shown below.
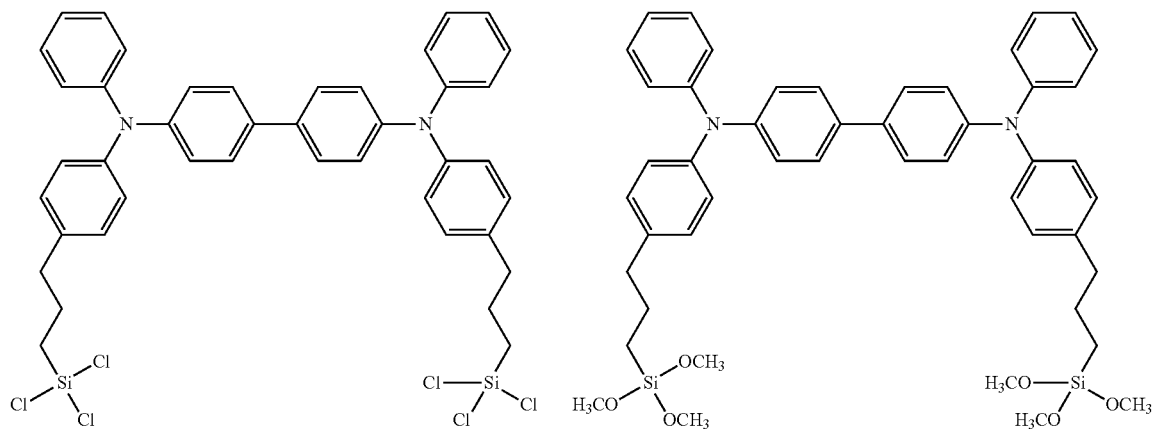
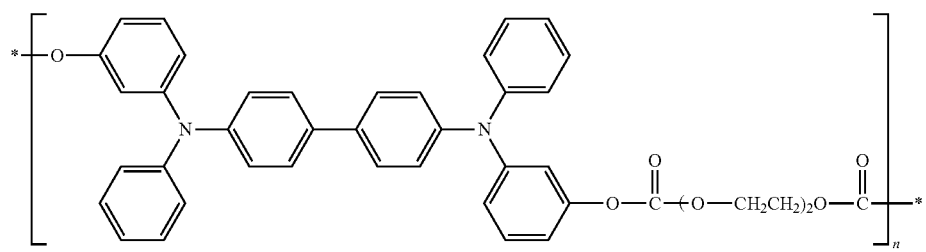

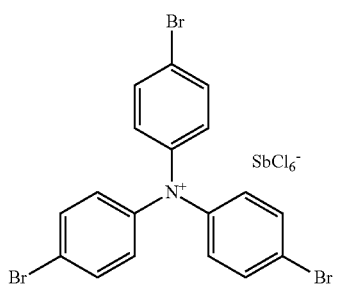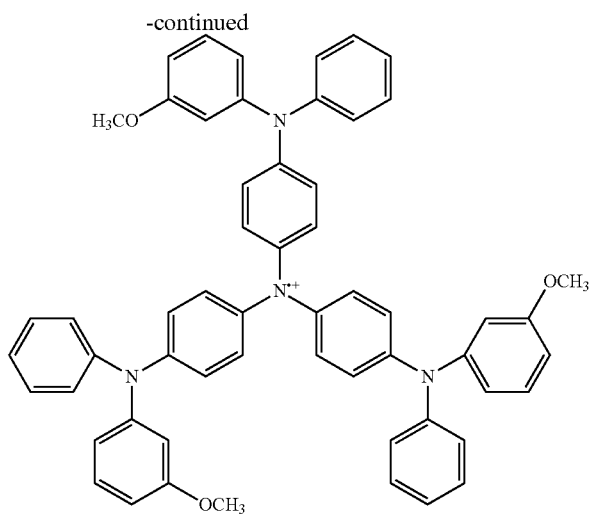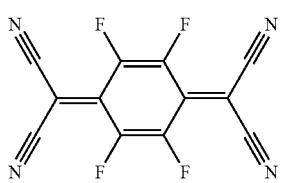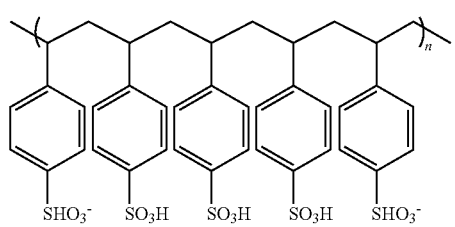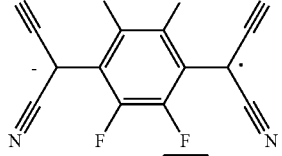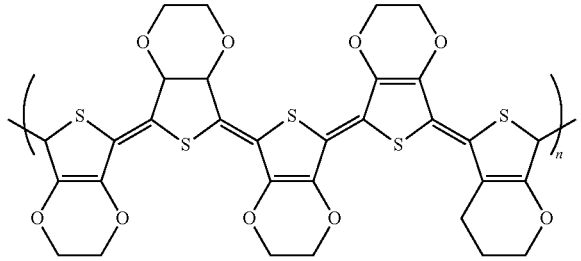
Preferred examples of a compound that may be used as the hole transporting material are shown below.
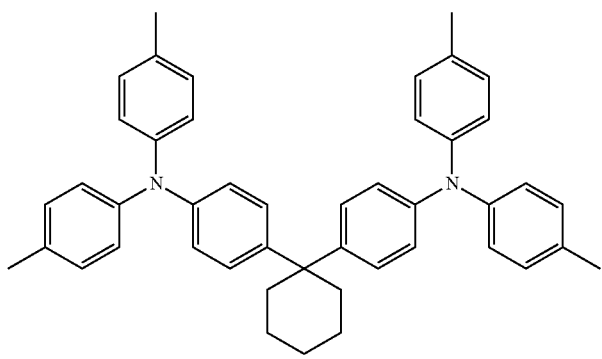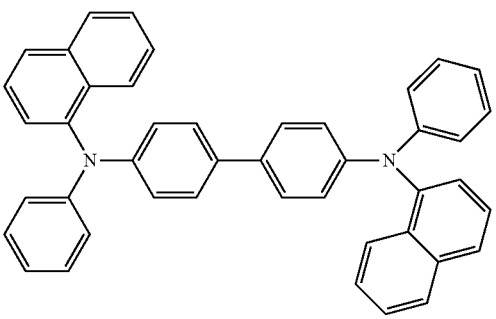

-continued
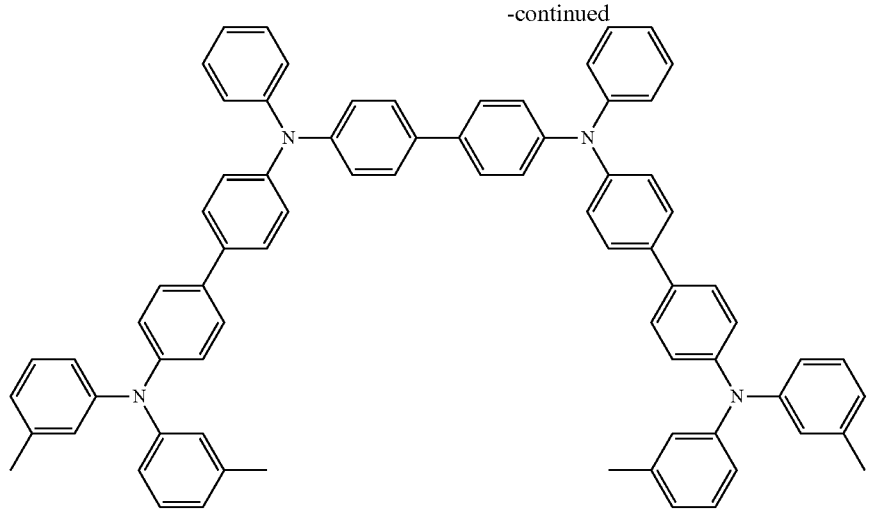
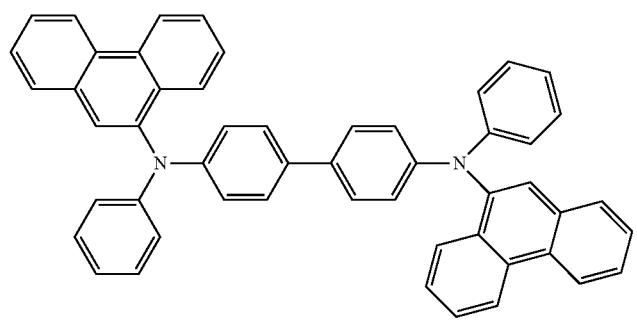
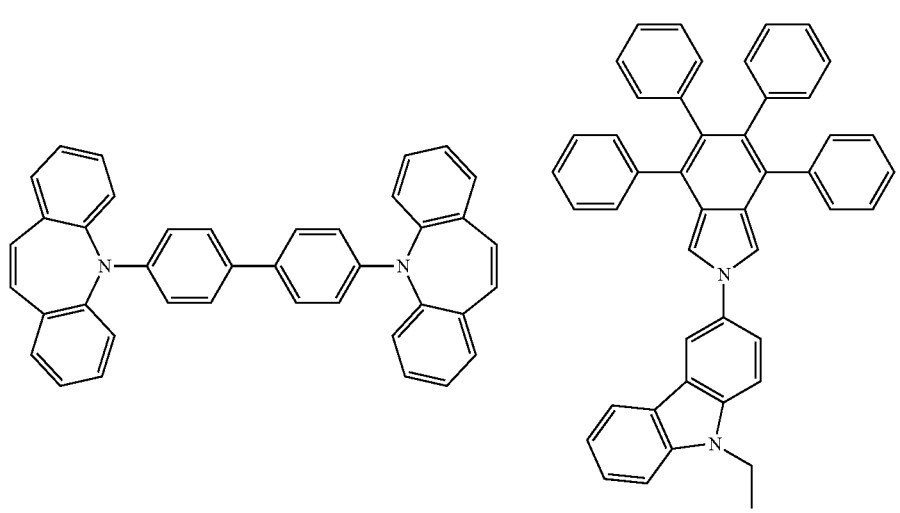

-continued
99
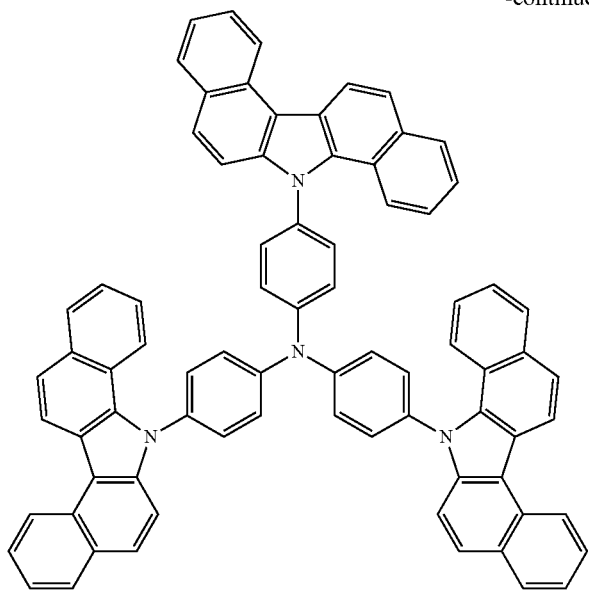
100
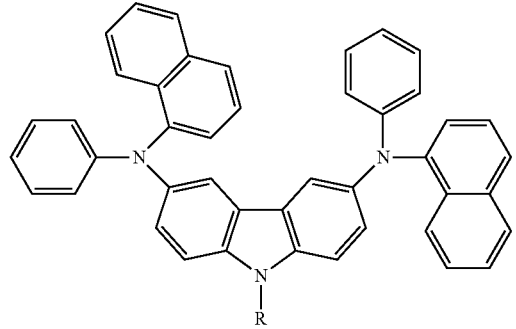
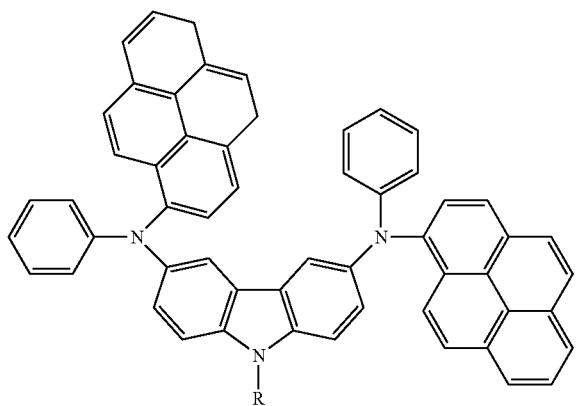
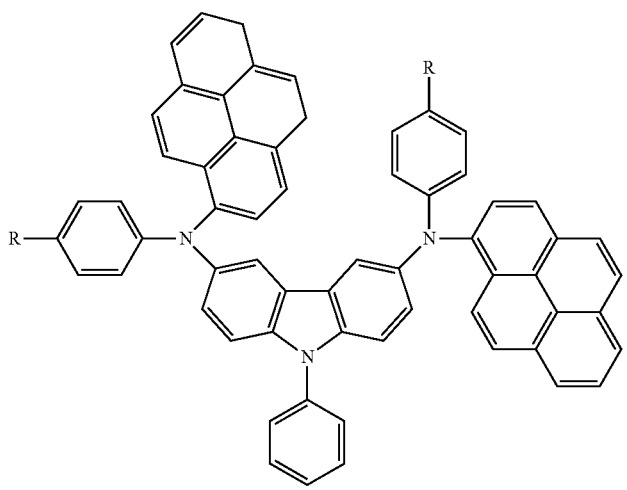

101
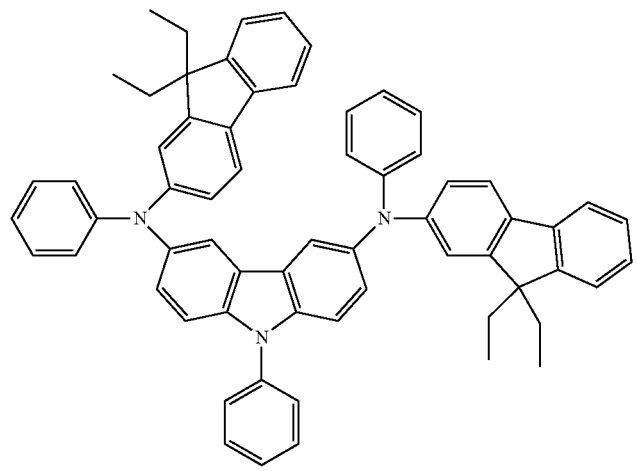
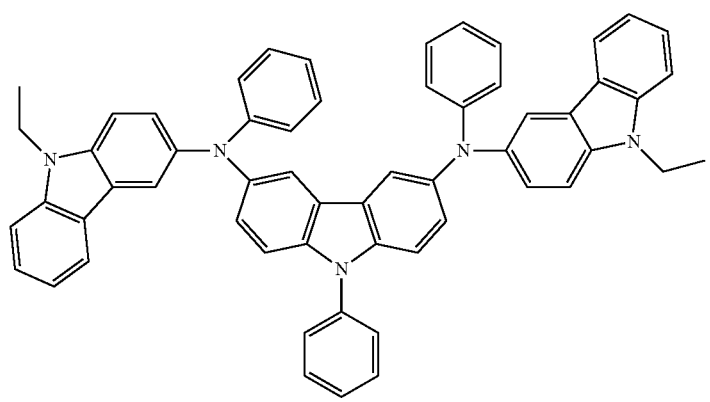
102
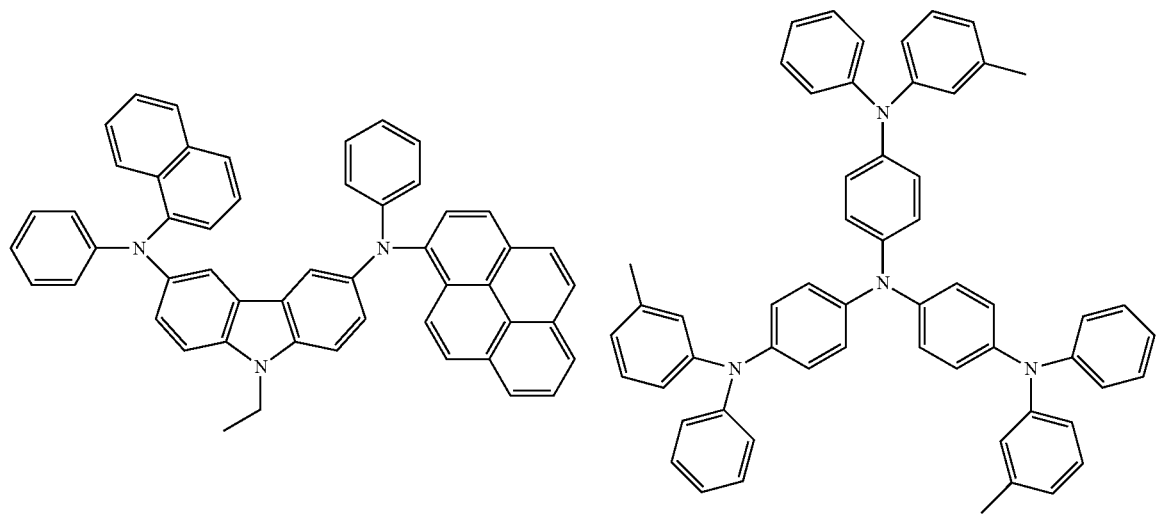

103 104
-continued
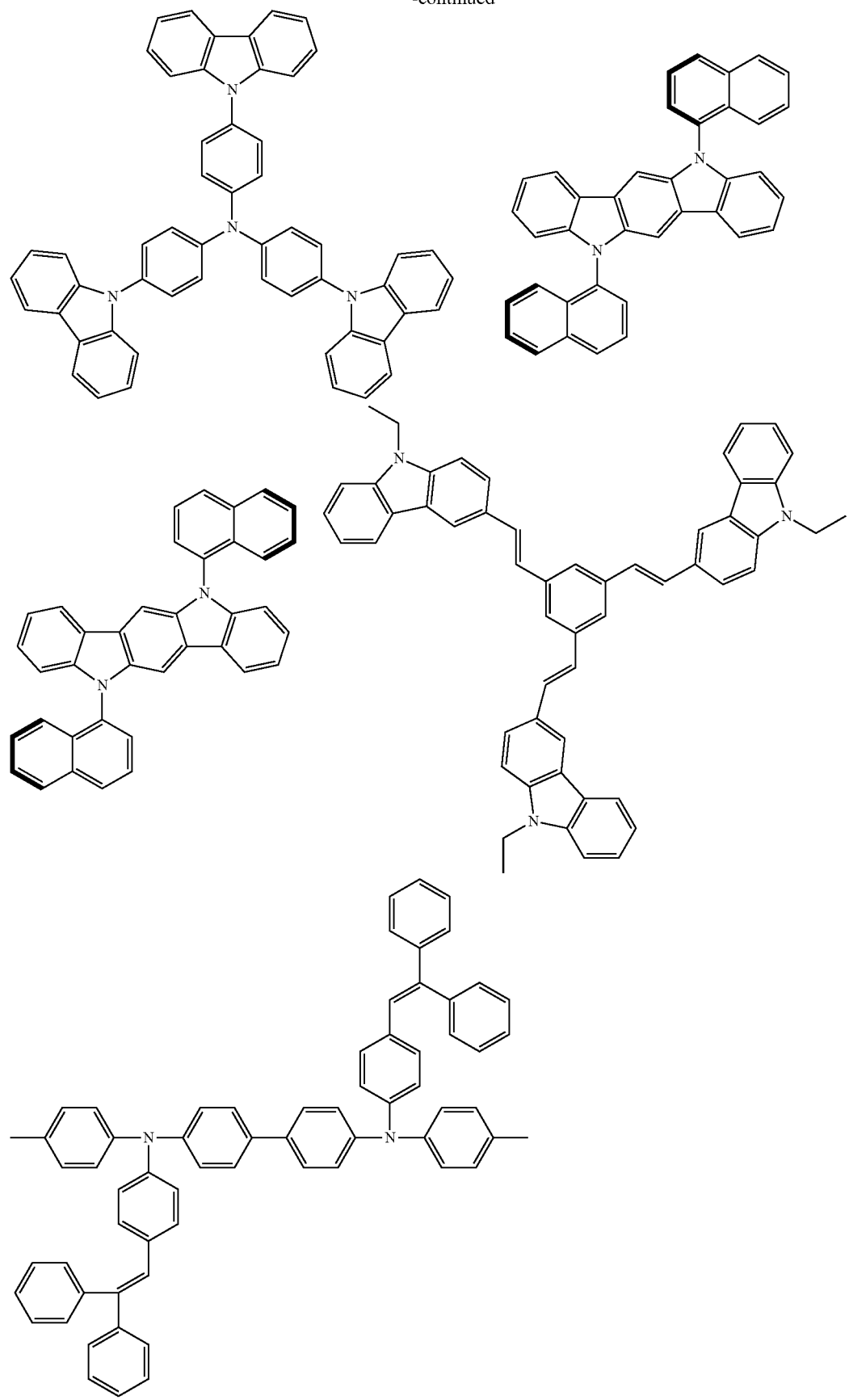

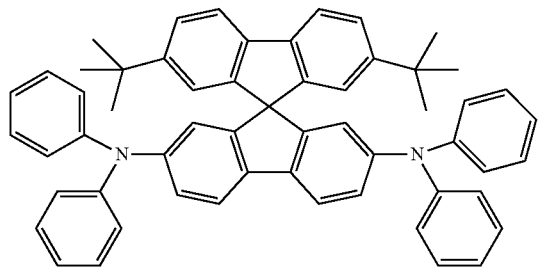
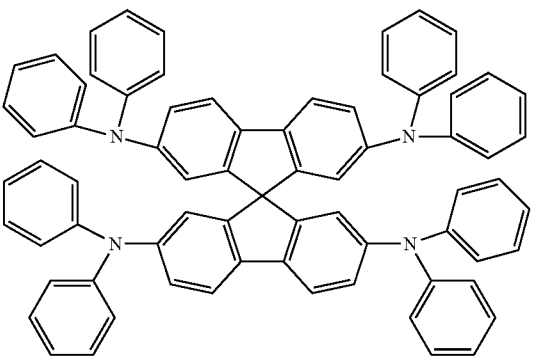
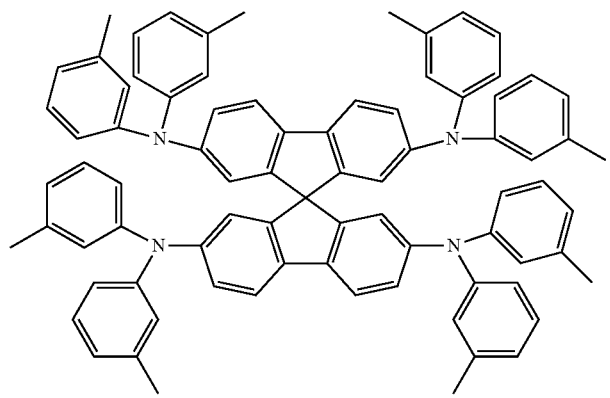
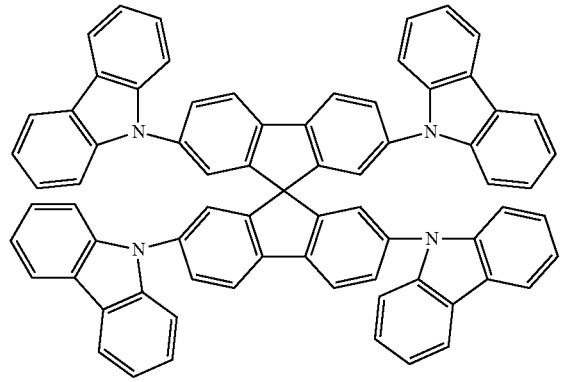
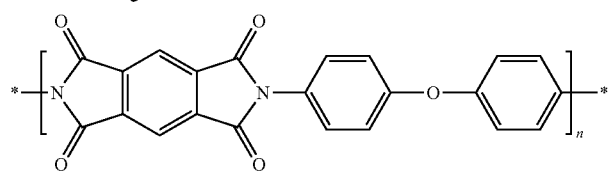
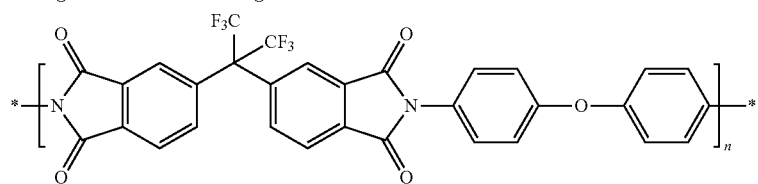
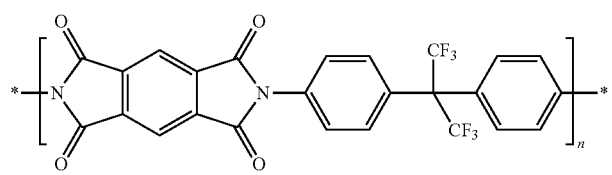

107 108
-continued
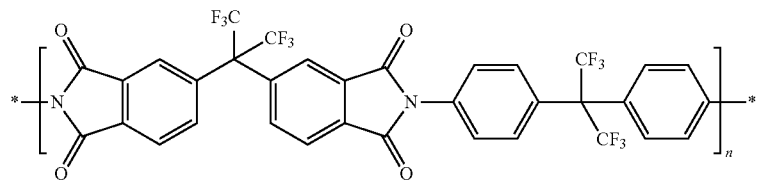
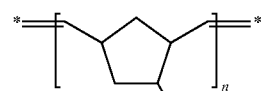
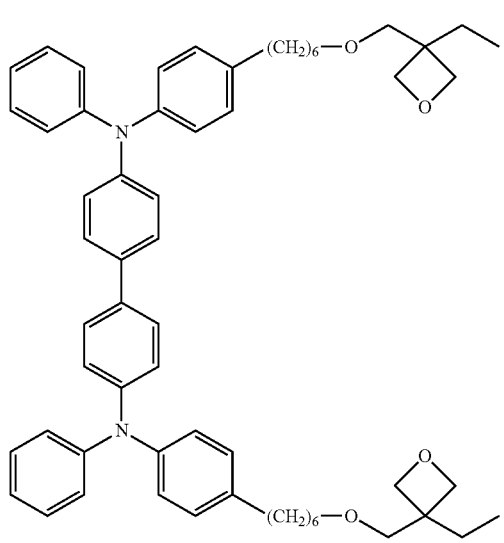
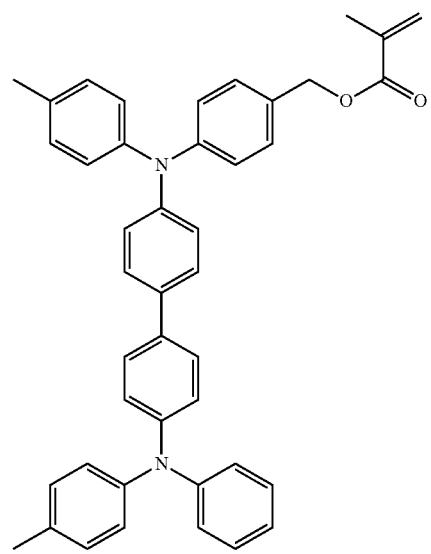
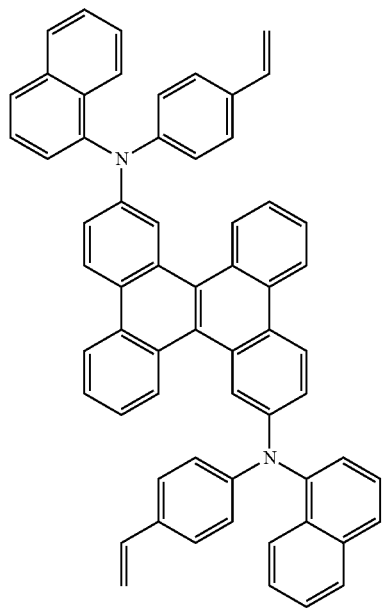

-continued
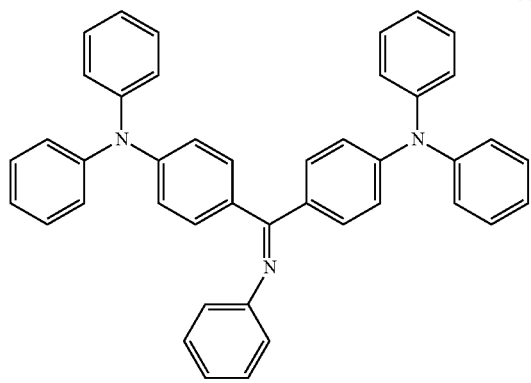
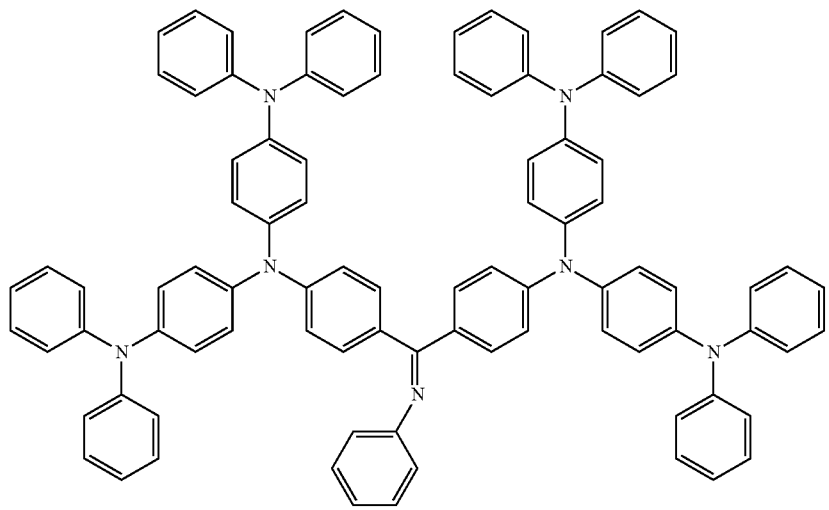
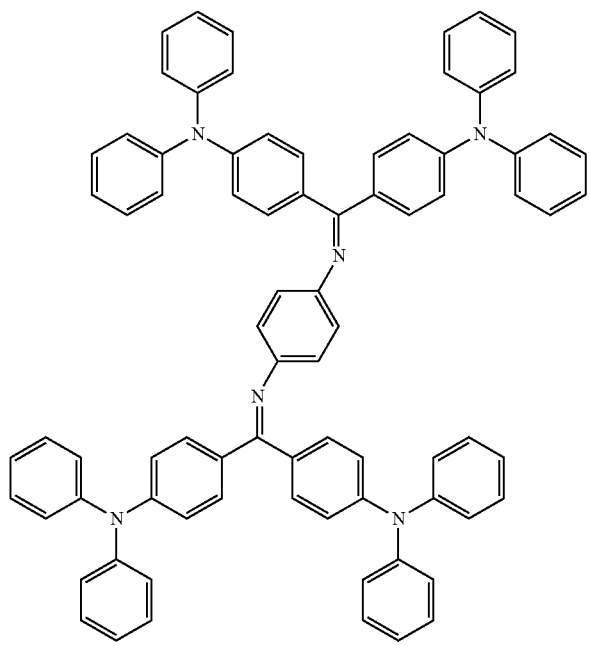

-continued
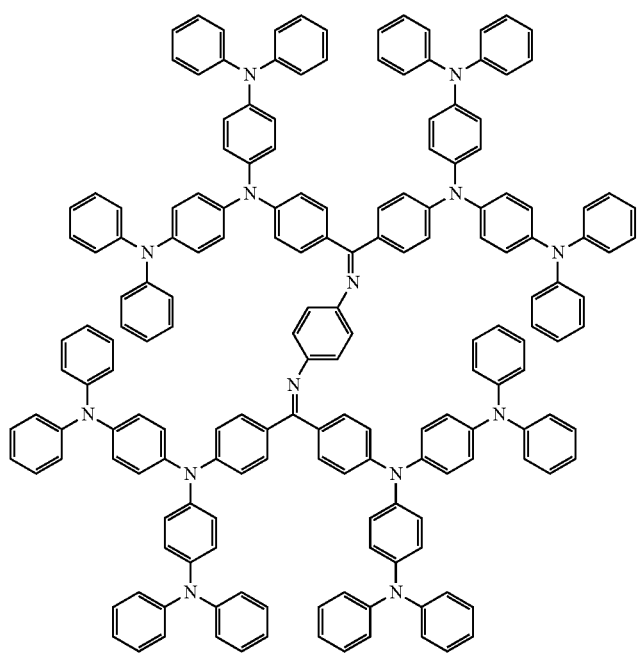
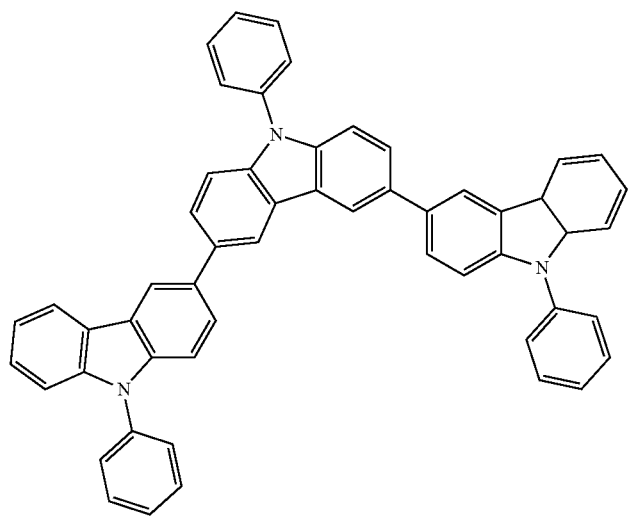
R =
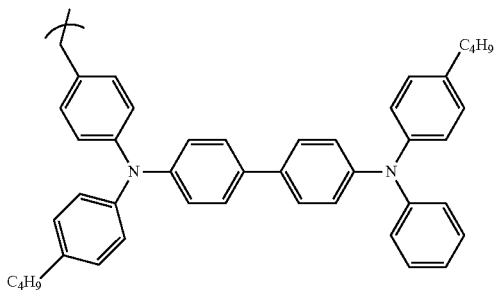

Preferred examples of a compound that may be used as the electron barrier material are shown below.
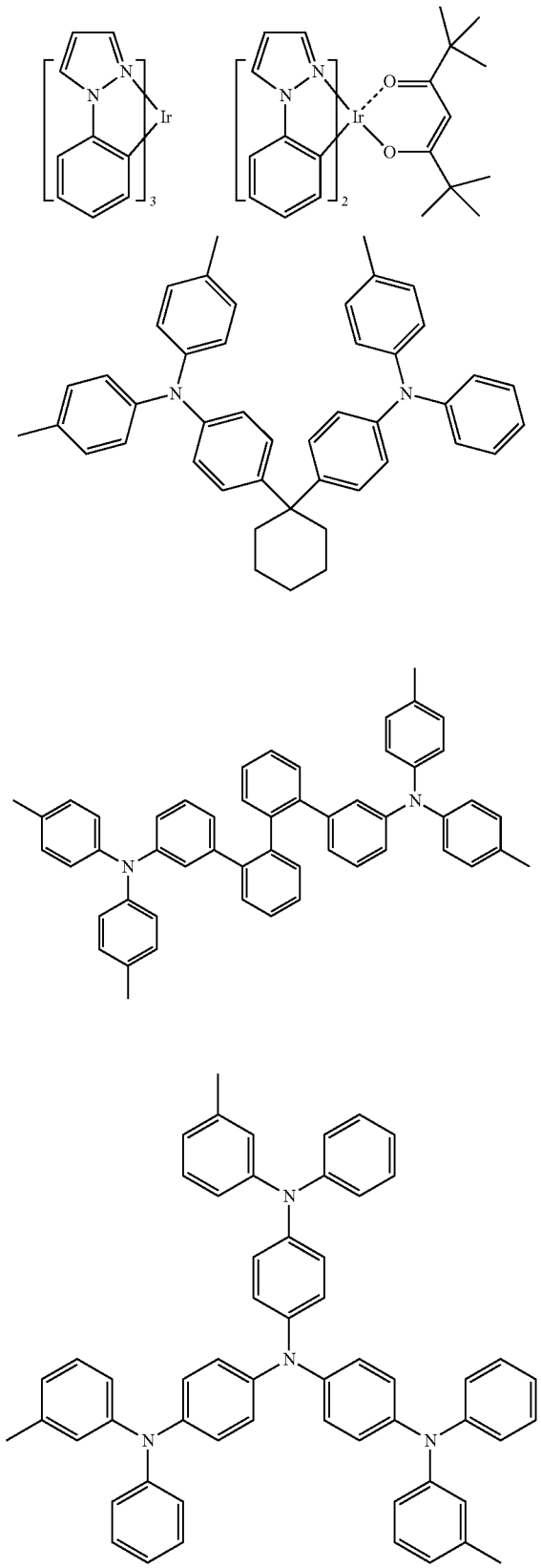
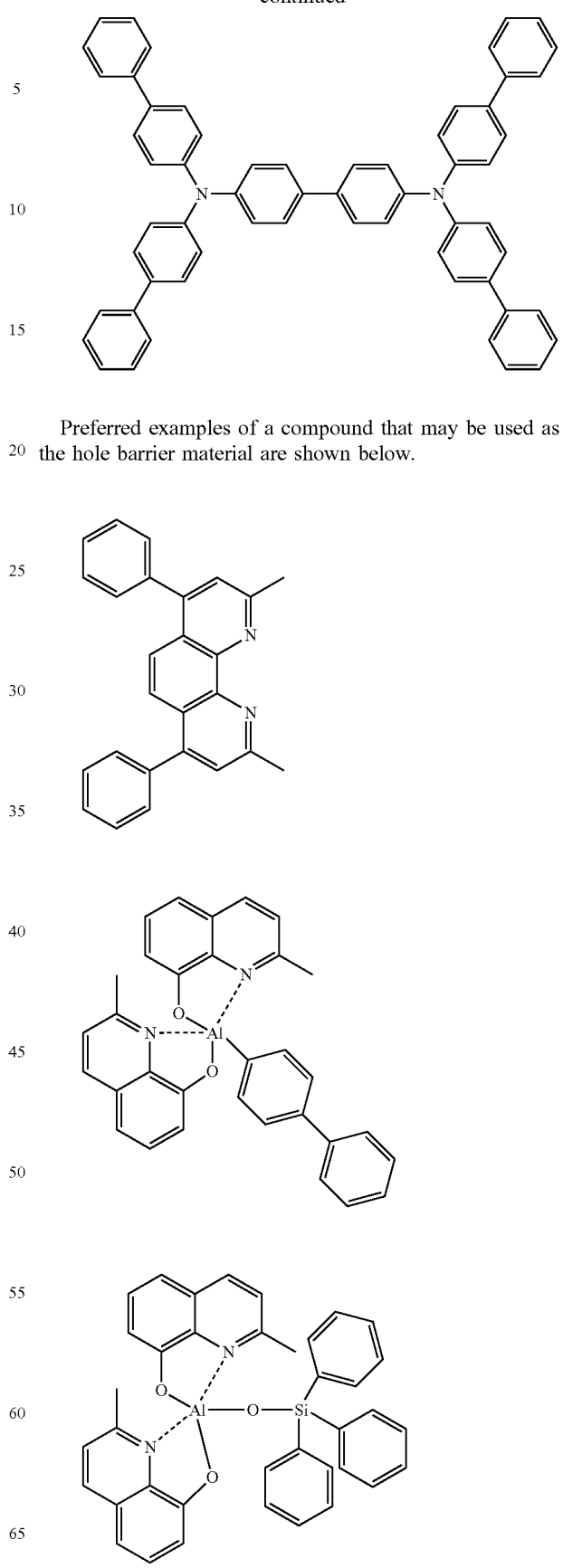
Preferred examples of a compound that may be used as the hole barrier material are shown below.

115
-continued
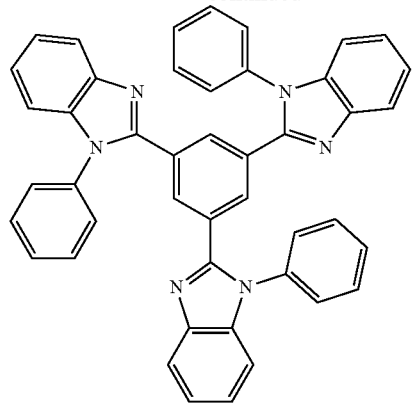
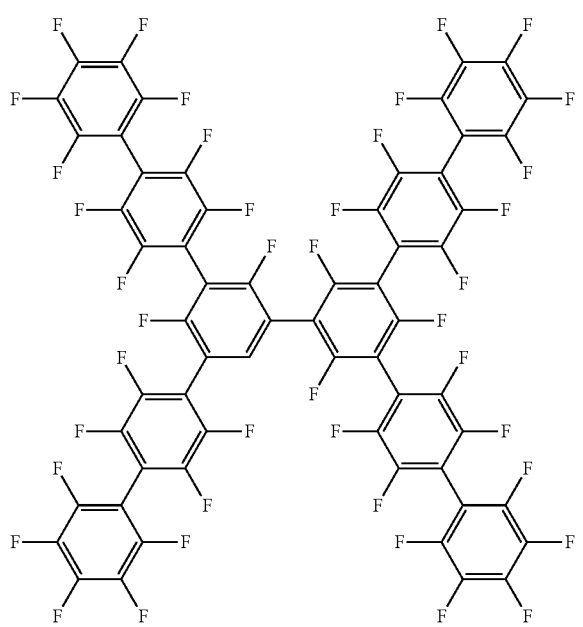
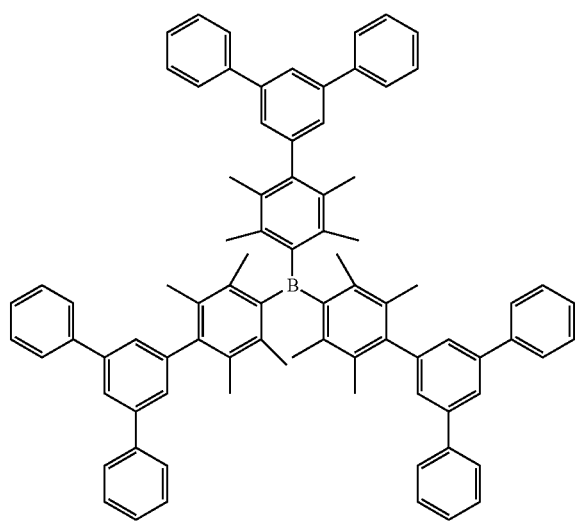
116
-continued
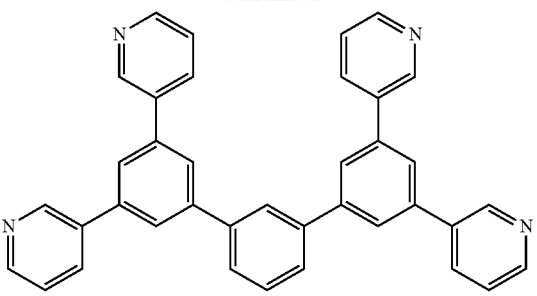
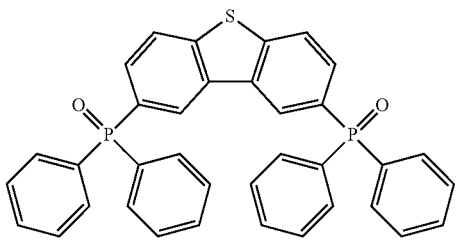
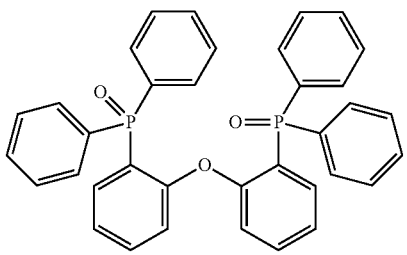
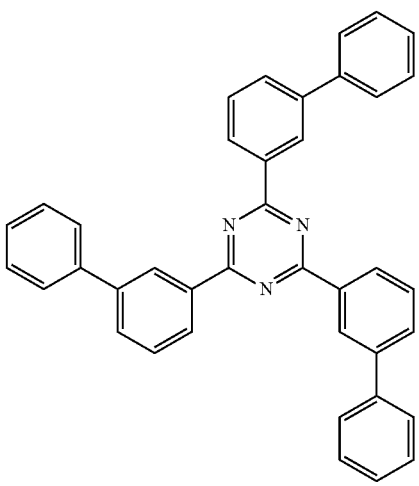
Preferred examples of a compound that may be used as the electron transporting material are shown below.

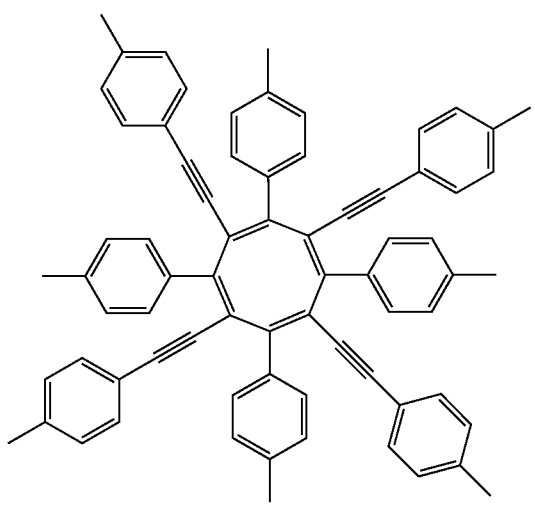
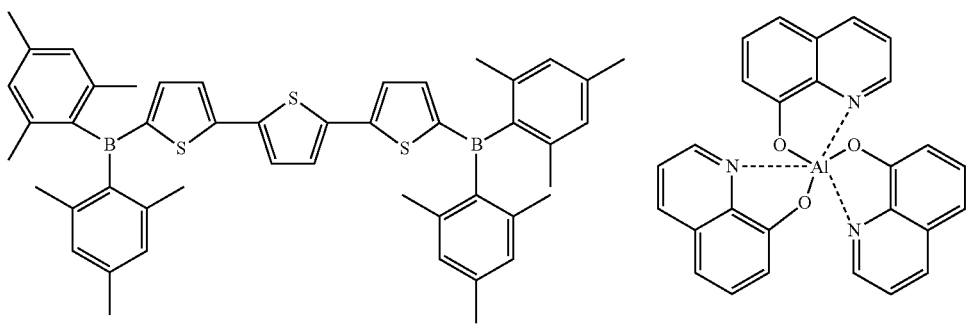
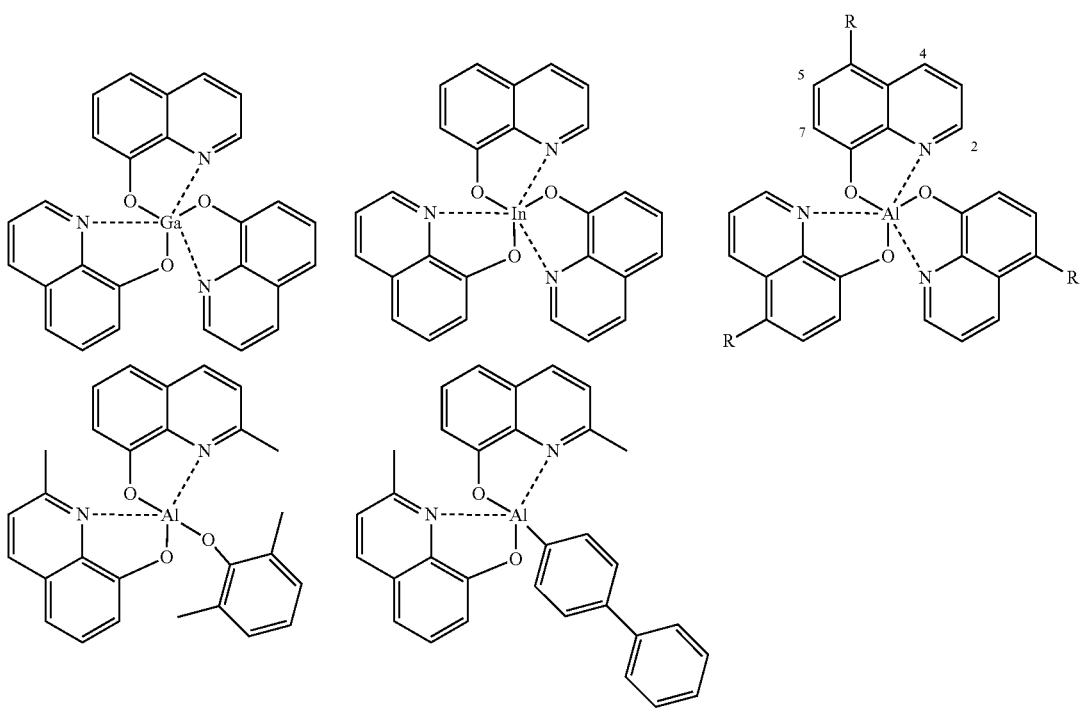

119
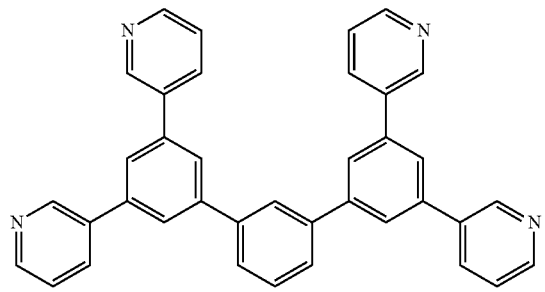
120
-continued
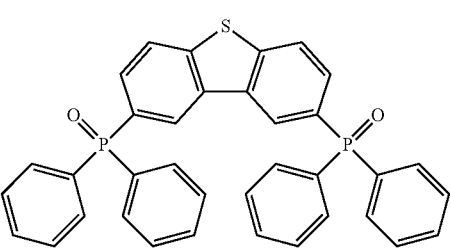
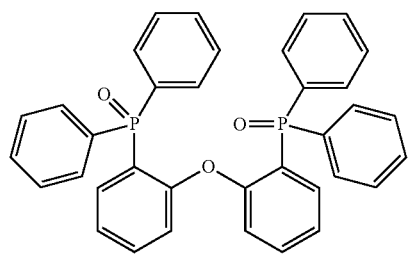
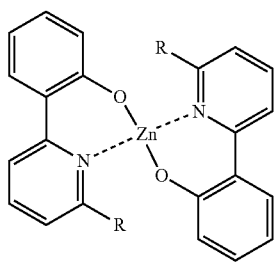
R = H
R = :
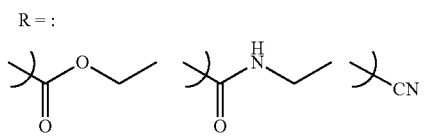
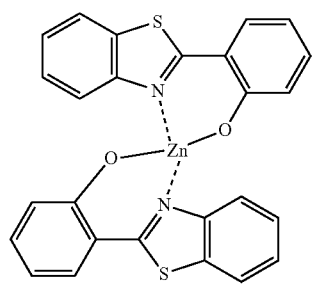
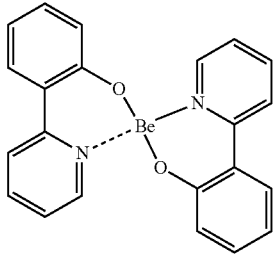
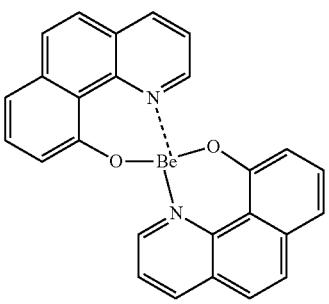
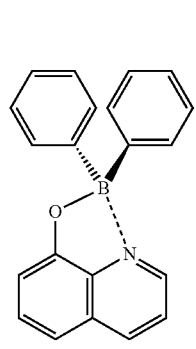
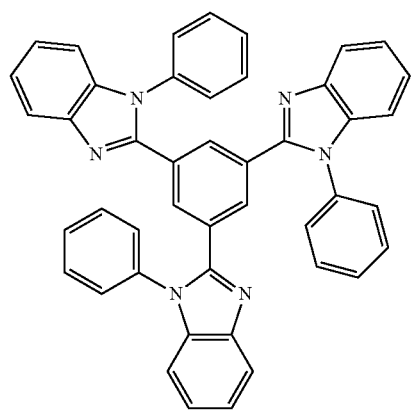

121 122
-continued
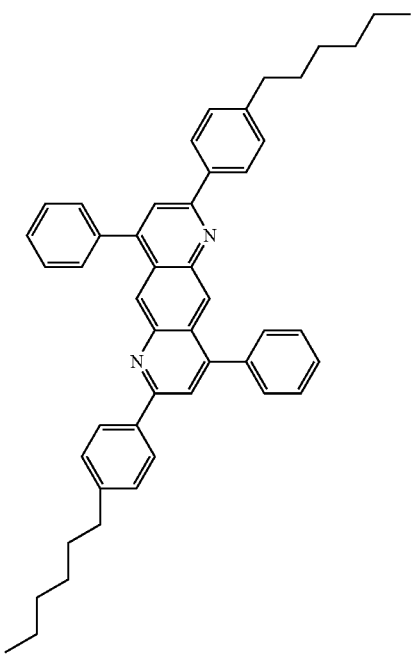
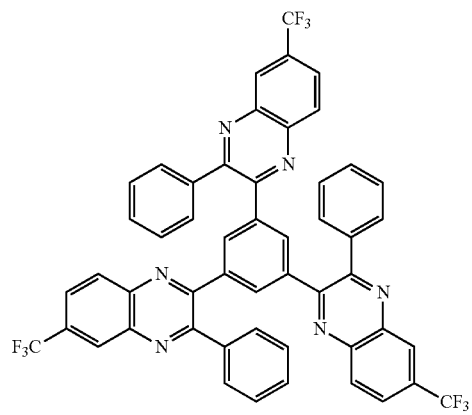
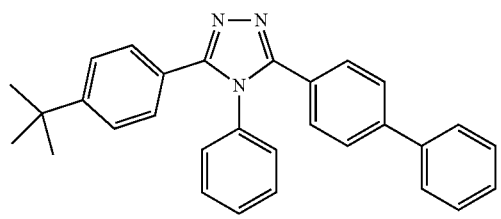
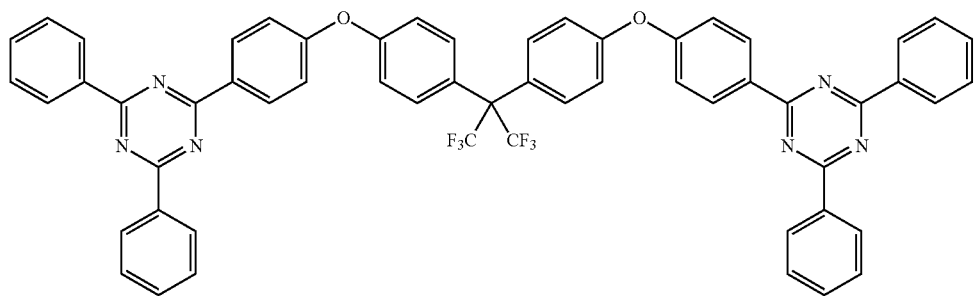
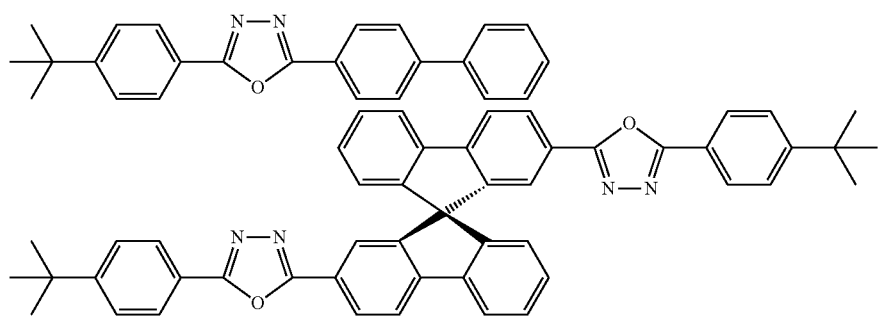

-continued
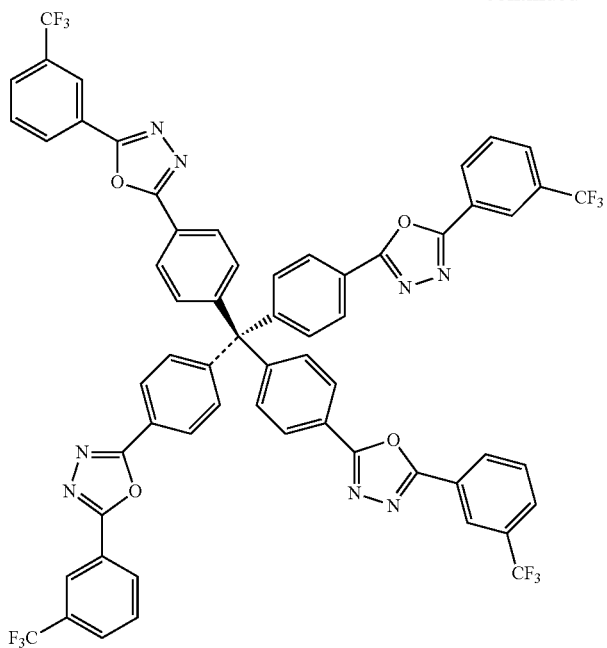
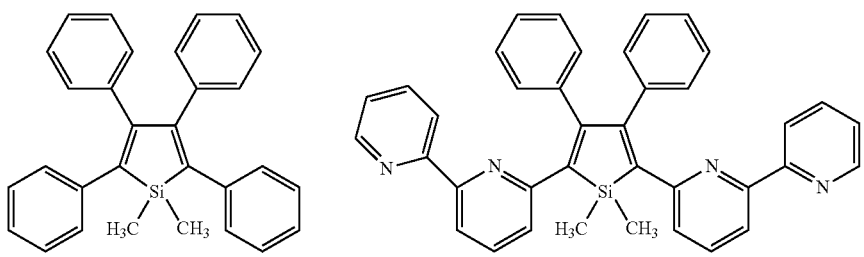
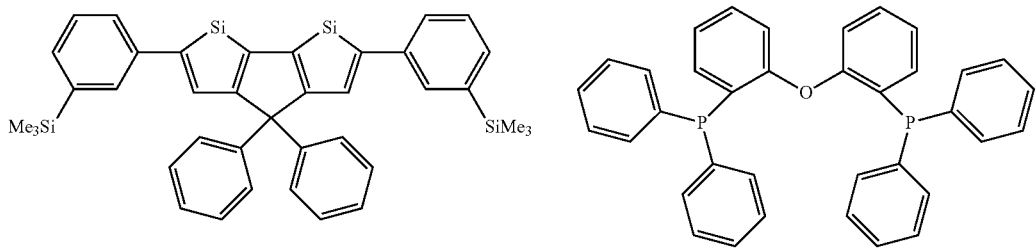
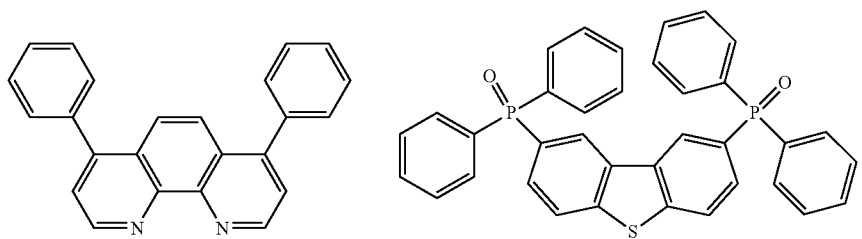

Preferred examples of a compound that may be used as the electron injection material are shown below.

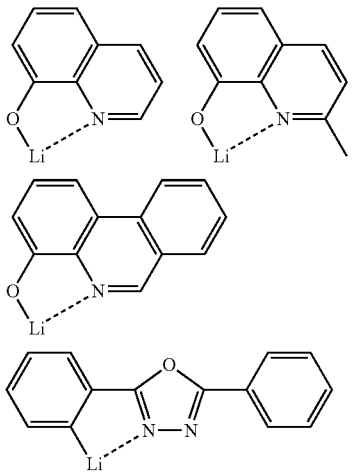

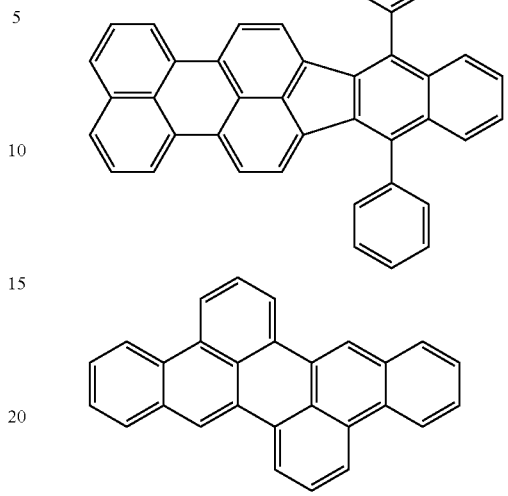

Preferred examples of a compound as a material that may be added are shown below. For example, the compound may be added as a stabilizing material.

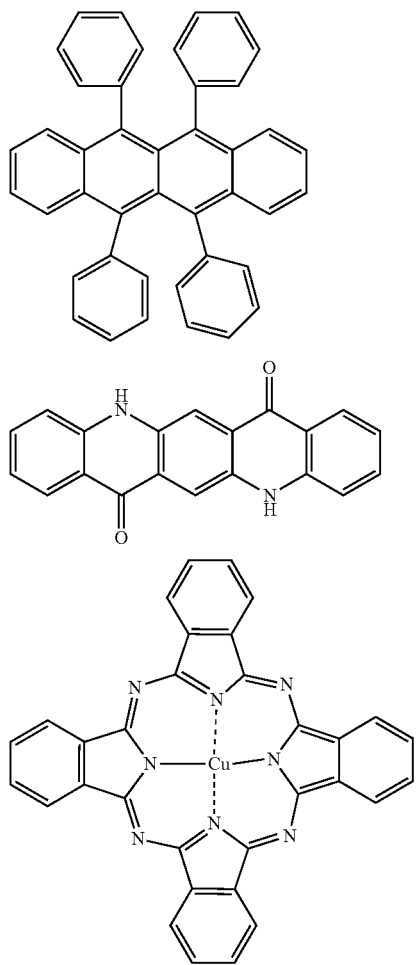

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter fluorescent light lifetime than the delayed fluorescent light, and thus the light emission lifetime may be distinguished between the fluorescent light and the delayed fluorescent light.

The phosphorescent light may substantially not observed with a normal organic compound, such as the compound in the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLES

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis Example 1

Synthesis of Compound 3

In a two-necked recovery flask having been substituted with nitrogen, 2-(4-iodophenyl)-4,6-diphenyl-1,3,5-triazine (1.74 g, 4.0 mmol), 9H, 9H'-[3,3']bicarbazoyl (665 g, 2.0 mmol), potassium carbonate (1.11 g, 8.0 mmol), copper powder (25 mg, 0.4 mmol), and 15 mL of nitrobenzene were added, and heated under refluxing at 170° C. for 24 hours. The reaction mixture was allowed to cool to room temperature, to which 50 mL of chloroform and 50 mL of water were added, and the organic layer thus separated was extracted. The extraction with chloroform was repeated three times. Chloroform was distilled off under reduced pressure by heating, and isolation and purification with silica gel chromatography using a mixed solvent of chloroform and hexane (1/1) were performed. The compound 3 was obtained as a whitish yellow solid matter (703 mg, yield: 55%).

Compound 3

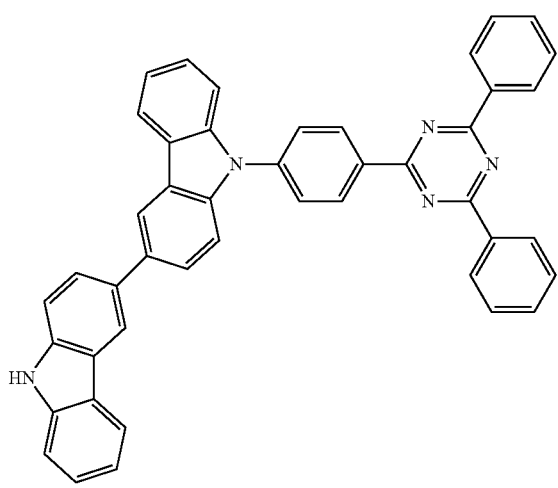

Production and Evaluation of Device

An organic photoluminescent device and an organic electroluminescent device were produced and evaluated as follows.

The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

The difference ($\Delta E_{ST}$) between the singlet energy ($E_{S1}$) and the triplet energy ($E_{T1}$) of the materials was obtained in such a manner that the singlet energy ($E_{S1}$) and the triplet energy ($E_{T1}$) were measured in the following manners, and the difference was obtained by the expression, $\Delta E_{ST} = E_{S1} - E_{T1}$.

(1) Singlet Energy $E_{S1}$

The compound to be measured and mCP were vapor-co-deposited to a thickness of 100 nm on a Si substrate such that a concentration of the compound to be measured was adjusted to 6% by weight, which was designated as a specimen. The specimen was measured for a fluorescence spectrum at ordinary temperature (300 K). The light emission was accumulated from immediately after the incidence of excitation light to after 100 nsec from the incidence, thereby providing a fluorescence spectrum with the light emission intensity as the ordinate and the wavelength as the abscissa. In the fluorescence spectrum, the ordinate was the light emission, and the abscissa was the wavelength. A tangent line was drawn for the upstanding part of the light emission spectrum on the short wavelength side, and the wavelength kedge (nm) of the intersection point of the tangent line and the abscissa was obtained. The wavelength value was converted to an energy value according to the following conversion expression to provide the singlet energy $E_{S1}$.

$$E_{S1}(\text{eV}) = 1{,}239.85/\lambda\text{edge} \quad \text{Conversion Expression}$$

The light emission spectrum was measured with a nitrogen laser (MNL200, produced by Lasertechnik Berlin GmbH) as an excitation light source and a streak camera (C4334, produced by Hamamatsu Photonics K.K.) as a detector.

(2) Triplet Energy $E_{T1}$

The same specimen as used for the singlet energy $E_{S1}$ was cooled to 5 K, the specimen for measuring phosphorescent light was irradiated with excitation light (337 nm), and the phosphorescence intensity was measured with a streak camera. The light emission was accumulated from after 1 msec from the incidence of excitation light to after 10 msec from the incidence, thereby providing a phosphorescence spectrum with the light emission intensity as the ordinate and the wavelength as the abscissa. A tangent line was drawn for the upstanding part of the phosphorescence spectrum on the short wavelength side, and the wavelength λedge (nm) of the intersection point of the tangent line and the abscissa was obtained. The wavelength value was converted to an energy value according to the following conversion expression to provide the triplet energy $E_{T1}$.

$$E_{T1}(\text{eV}) = 1{,}239.85/\lambda\text{edge} \quad \text{Conversion Expression}$$

The tangent line for the upstanding part of the phosphorescence spectrum on the short wavelength side was drawn in the following manner. Over the range in the phosphorescence spectrum curve of from the short wavelength end to the maximum peak value closest to the short wavelength end among the maximum peak values of the spectrum, a tangent line was assumed at each point on the curve while moving within the range toward the long wavelength side. The gradient of the tangent line was increased as the curve was standing up (i.e., the value of the ordinate was increased). The tangent line that was drawn at the point where the gradient thereof became maximum was designated as the tangent line for the upstanding part of the phosphorescence spectrum on the short wavelength side.

A maximum peak having a peak intensity that was 10% or less of the maximum peak intensity of the spectrum was not designated as the maximum peak value closest to the short wavelength end, and the tangent line that was drawn at the point where the gradient became maximum that was closest to the maximum peak value closest to the short wavelength end was designated as the tangent line for the upstanding part of the phosphorescence spectrum on the short wavelength side.

Example 1

Production and Evaluation of Organic Photoluminescent Device (Solution)

Figure 2:
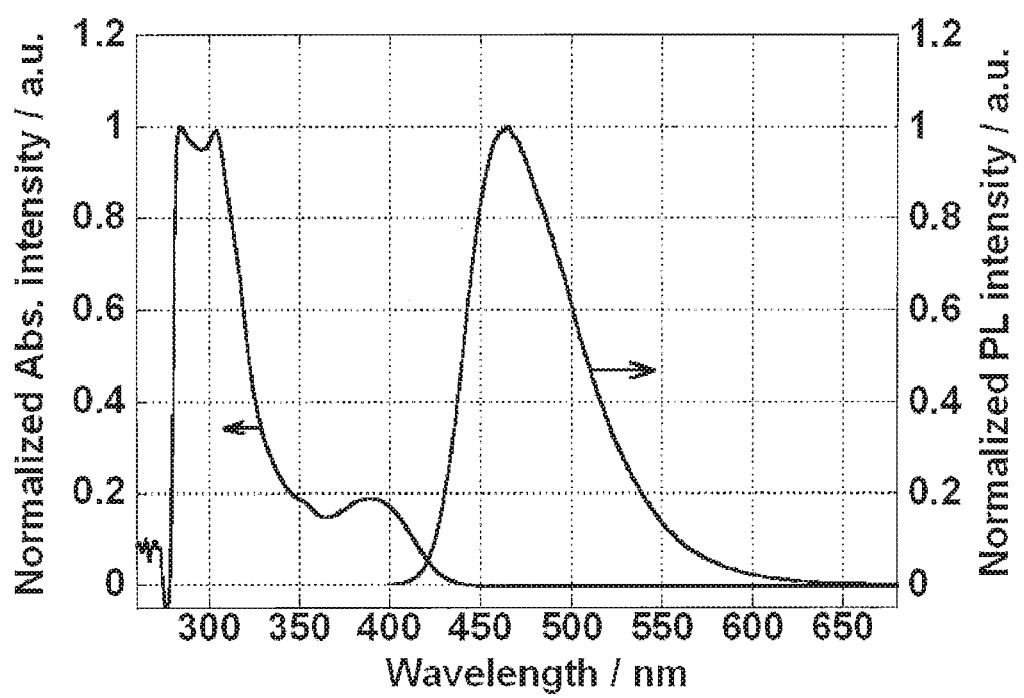
FIG. 2 is the light emission spectrum of the toluene solution in Example 1.
Figure 3:
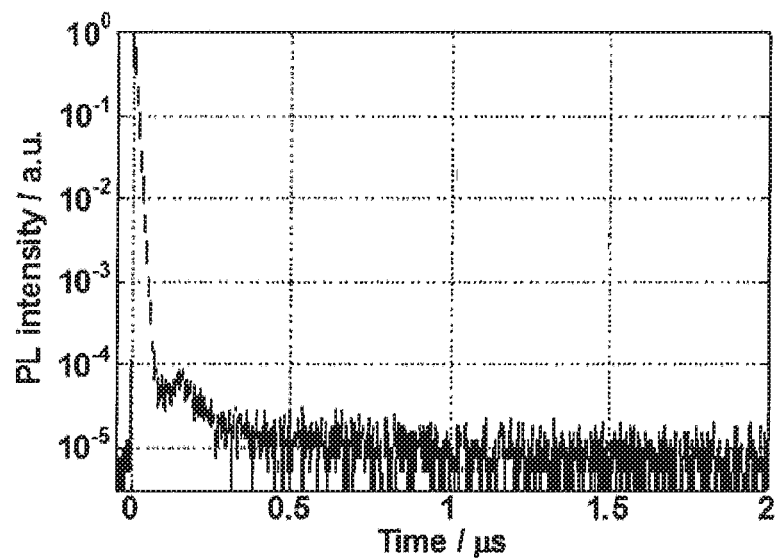
FIG. 3 is the transient decay curve of the toluene solution in Example 1.

A toluene solution (concentration: $10^{-5}$ mol/L) of the compound 1 shown below was prepared and irradiated with ultraviolet light at 300 K under bubbling with nitrogen, and thus fluorescent light having a peak wavelength of 465 nm was observed as shown in FIG. 2. The photoluminescence quantum efficiency of the compound 1 in the toluene solution was measured at 300 K with an absolute PL quantum yields measurement system (Quantaurus-QY, produced by Hamamatsu Photonics K.K.), and was 58.6% before bubbling with nitrogen and 71.2% after bubbling with nitrogen, which resulted in an increase of approximately 13%. FIG. 3 shows the transient decay curve after bubbling with nitrogen. The transient decay curves each show the measurement result of the light emission lifetime in the process of deactivating the light emission intensity starting from the irradiation of the compound with excitation light. In the ordinary one-component light emission (fluorescent light or phosphorescent light), the light emission intensity decays monoexponentially. This means the linear decay in the case where the ordinate of the graph is in a semilogarithmic scale. In the transient decay curve of the compound 1 shown in FIG. 3, the linear component (fluorescent light) is observed in the initial stage of observation, but a component that deviates from the linearity appears after several microseconds. This is the light emission of the delayed component, and the signal obtained by adding the initial component forms a gentle curve having a long tail on the long time side. Thus, the measurement of the light emission lifetime confirmed that the compound 1 was a light-emitting material that includes a delayed component in addition to a fluorescent component.

Compound 1

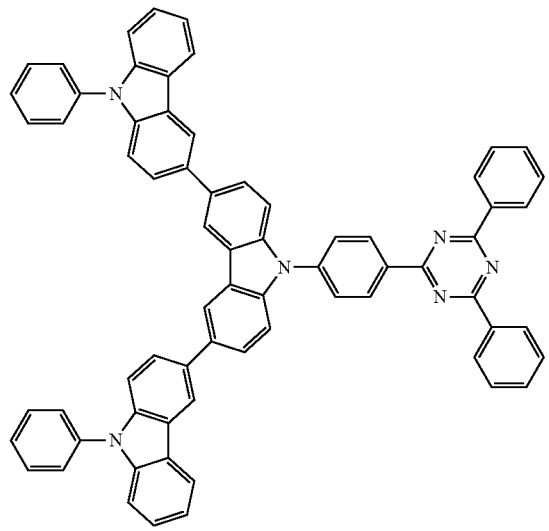

Example 2

Production and Evaluation of Organic Photoluminescent Device (Solution)

Figure 4:
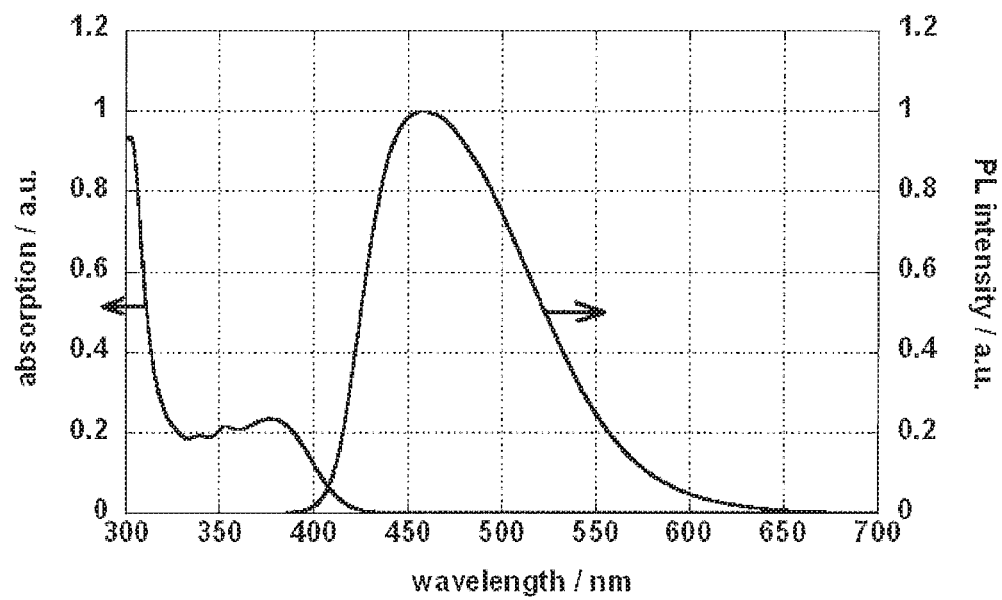
FIG. 4 is the light emission spectrum of the toluene solution in Example 2.

A toluene solution (concentration: $10^{-5}$ mol/L) of the compound 2 shown below was prepared and irradiated with ultraviolet light at 300 K under bubbling with nitrogen, and thus fluorescent light having a peak wavelength of 459 nm was observed as shown in FIG. 4. The photoluminescence quantum efficiency of the compound 2 in the toluene solution was measured at 300 K with an absolute PL quantum yields measurement system (Quantaurus-QY, produced by Hamamatsu Photonics K.K.), and was 59.6% before bubbling with nitrogen and 79.7% after bubbling with nitrogen, which resulted in an increase of approximately 20%. Delayed fluorescent light was observed in the measurement method in Example 1 ($\tau_1$=0.007 s, $\tau_2$=0.170 μs). $\Delta E_{ST}$ was 0.16 eV.

Compound 2

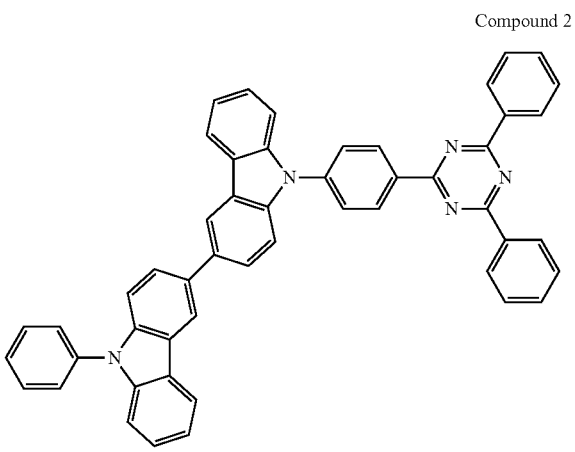 [SMILES: c1ccc(-c2nc(-c3ccccc3)nc(-c3ccc(-n4c5ccccc5c5cc(-c6ccc7c(c6)c6ccccc6n7-c6ccccc6)ccc54)cc3)n2)cc1]

Comparative Example 1

Production and Evaluation of Organic Photoluminescent Device (Solution)

Figure 5:
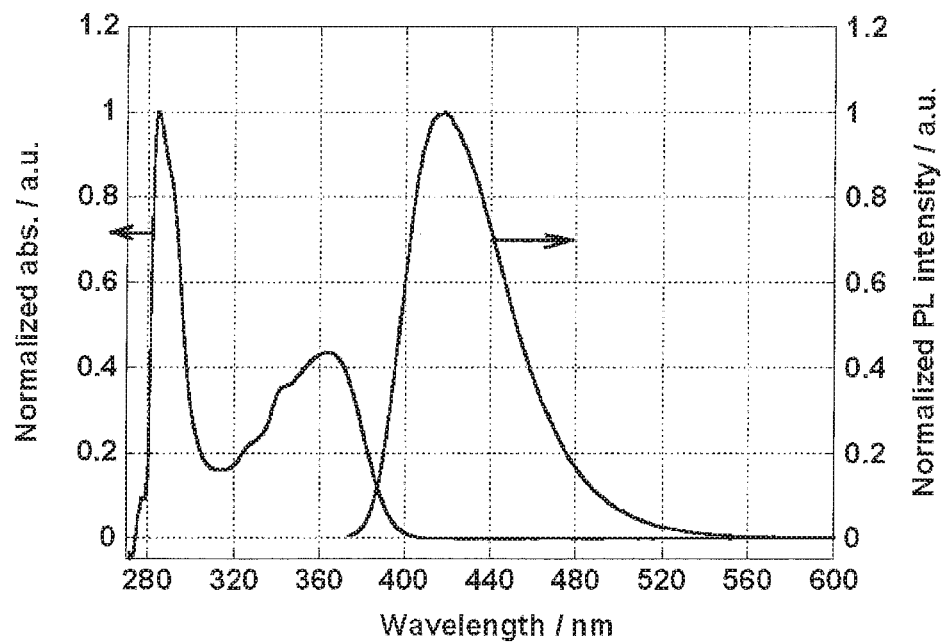
FIG. 5 is the light emission spectrum of the toluene solution in Comparative Example 1.
Figure 6:
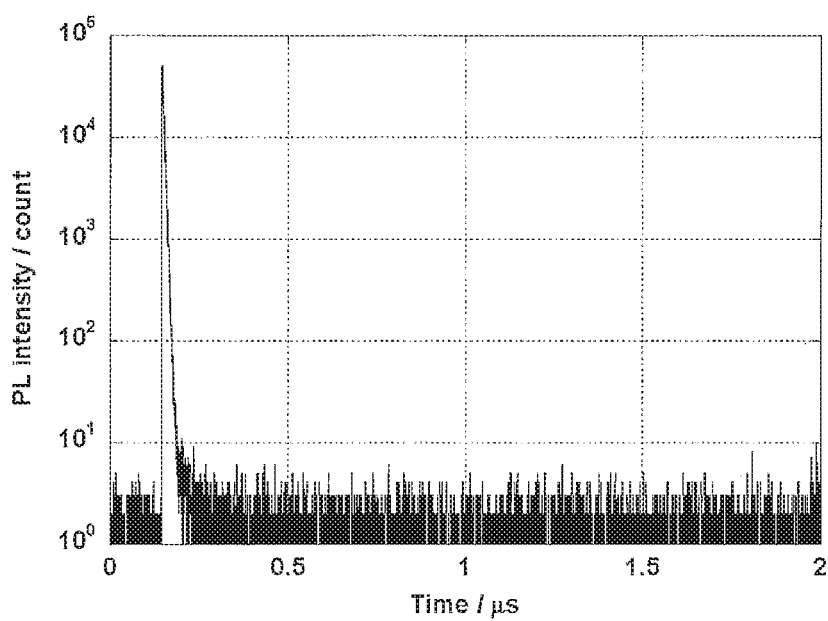
FIG. 6 is the transient decay curve of the toluene solution in Comparative Example 1.

A toluene solution (concentration: $2.0 \times 10^{-5}$ mol/L) of the comparative compound 1 shown below was prepared and irradiated with ultraviolet light at 300 K under bubbling with nitrogen, and thus fluorescent light having a peak wavelength of 459 nm was observed as shown in FIG. 5. FIG. 6 shows the transient decay curve measured while bubbling with nitrogen. Delayed fluorescent light was not observed.

Comparative Compound 1

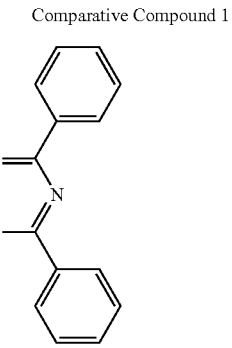

Example 3

Production and Evaluation of Thin Film Organic Photoluminescent Device (Thin Film)

Figure 7:
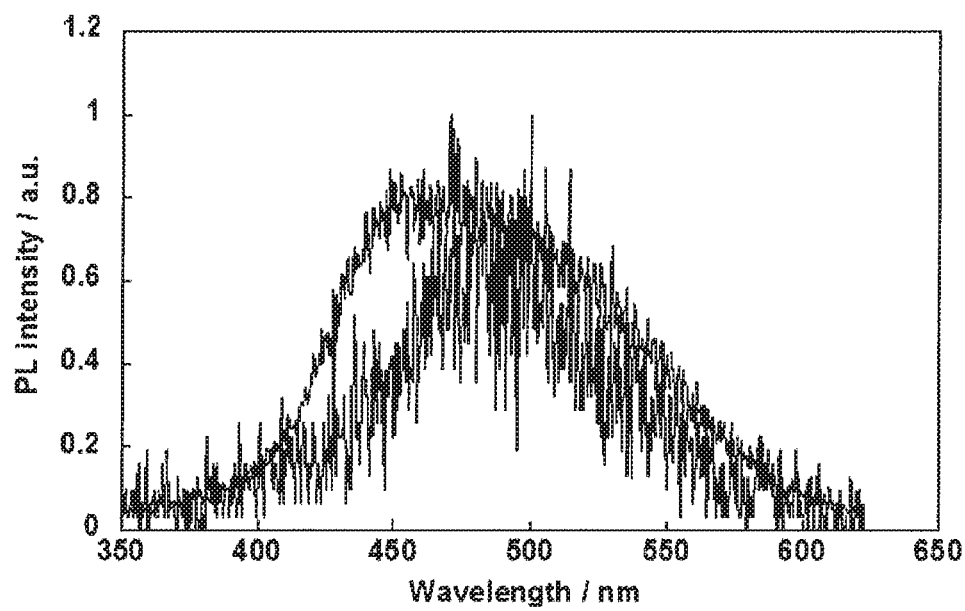
FIG. 7 is the light emission spectrum of the thin film organic photoluminescent device in Example 3.
Figure 8:
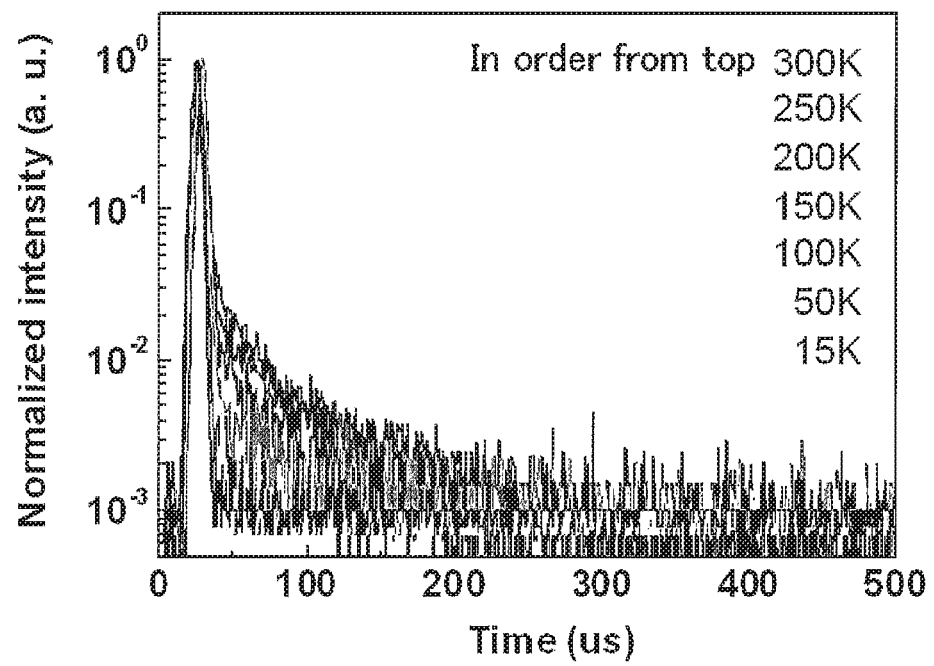
FIG. 8 is the transient decay curves of the thin film organic photoluminescent device in Example 3.

The compound 2 and DPEPO were vapor-deposited on a silicon substrate from separate vapor deposition sources under a vacuum degree of $5.0 \times 10^{-4}$ Pa, so as to form a thin film having a thickness of 100 nm and a concentration of the compound 2 of 6.0% by weight at a rate of 0.3 nm/sec, thereby providing a thin film organic photoluminescent device. FIG. 7 shows the light emission spectrum of the device measured with the same measuring apparatus as in Example 1. The device was measured with a compact fluorescence lifetime spectrometer (Quantaurus-tau, produced by Hamamatsu Photonics K.K.) at 300 K, 250 K, 200 K, 150 K, 100 K, 50 K, and 15 K, thereby providing the transient decay curves shown in FIG. 8. It was confirmed from FIG. 8 that thermal activation type delayed fluorescent light, in which the delayed fluorescent component was decreased with the decrease of the temperature, was obtained. The photoluminescence quantum efficiency was 95.6% at 300 K under a nitrogen stream.

Example 4

Production and Evaluation of Organic Electroluminescent Device

In this example, an organic electroluminescent device having a light-emitting layer formed of the compound 2 and DPEPO was produced and evaluated for the characteristics.

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 30 nm on ITO, and then mCP was formed to a thickness of 10 nm on the α-NPD film. Subsequently, the compound 2 and DPEPO were co-deposited thereon from separate vapor deposition sources to form a layer having a thickness of 15 nm, which was designated as a light-emitting layer. At this time, the concentration of the compound 2 was 6.0% by weight. DPEPO was then formed to a thickness of 10 nm, and TPBi was formed to a thickness of 40 nm. Lithium fluoride (LiF) was then vacuum vapor-deposited to a thickness of 0.8 nm, and then aluminum (Al) was vapor-deposited to a thickness of 100 nm to form a cathode, thereby completing an organic electroluminescent device.

Figure 9:
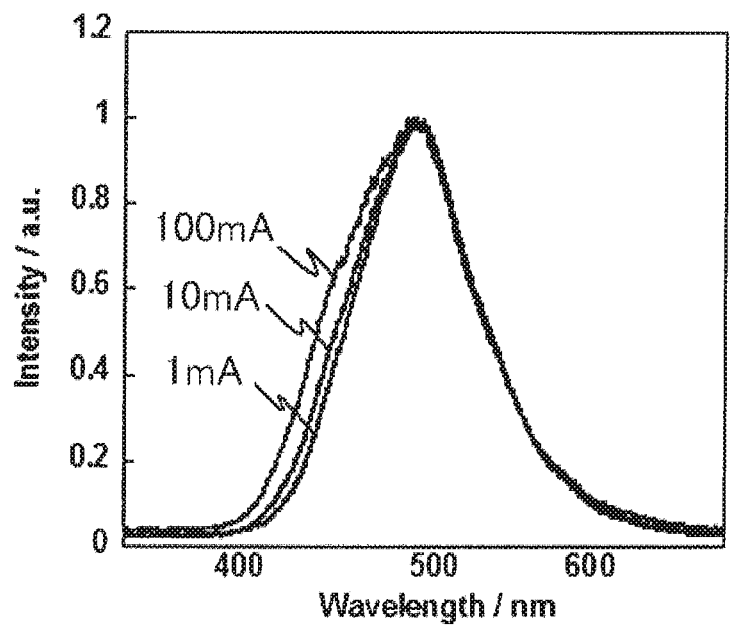
FIG. 9 is the light emission spectra of the organic electroluminescent device of Example 4.
Figure 10:
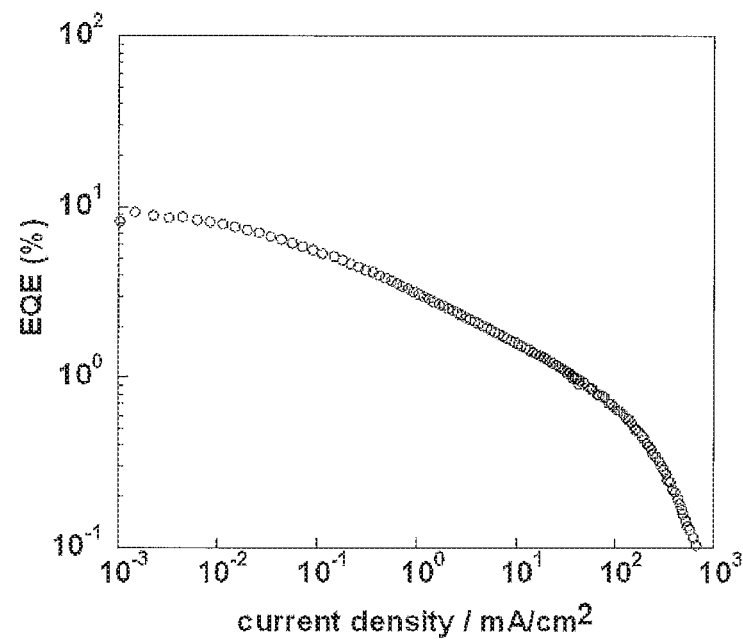
FIG. 10 is a graph showing the electric current density-external quantum efficiency characteristics of the organic electroluminescent device of Example 4.

The organic electroluminescent device thus produced was measured with a semiconductor parameter analyzer (E5273A, produced by Agilent Technologies, Inc.), an optical power meter (1930C, produced by Newport Corporation), and an optical spectrometer (USB2000, produced by Ocean Optics, Inc.). FIG. 9 shows the electroluminescence (EL) spectra (peak wavelength: 489 nm). FIG. 10 shows the electric current density-external quantum efficiency characteristics. The organic electroluminescent device using the compound 2 as a light-emitting material achieved a high external quantum efficiency of 9.3%. If an ideally balanced organic electroluminescent device is produced by using a fluorescent material having a light emission quantum efficiency of 100%, the external quantum efficiency of the fluorescent light emission may be from 5 to 7.5% assuming that the light extraction efficiency is from 20 to 30%. It has been ordinarily considered that this value is the theoretical limit value of an external quantum efficiency of an organic electroluminescent device using a fluorescent material. The organic electroluminescent device of the invention using the compound 2 is significantly excellent since a high external quantum efficiency that exceeds the theoretical limit value is achieved thereby.

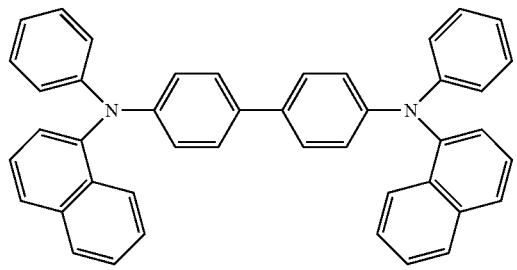

α-NPD

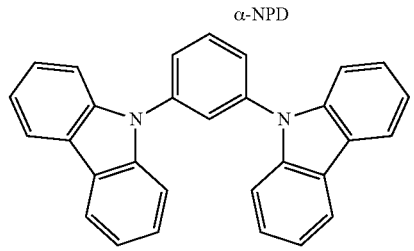

mCP

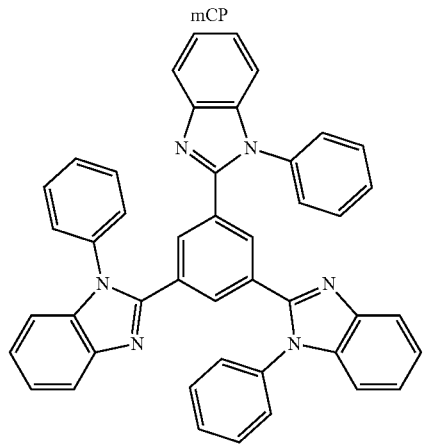

TPBi

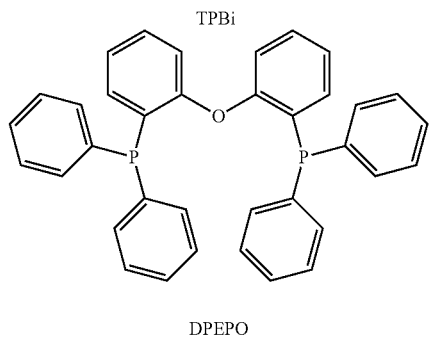

DPEPO

INDUSTRIAL APPLICABILITY

The compound of the invention is useful as a light-emitting material. Accordingly, the compound of the invention may be effectively used as a light-emitting material of an organic light-emitting device, such as an organic elec-

The invention claimed is:

1. A method for emitting delayed fluorescent light comprising irradiating or exciting a composition or device comprising a compound represented by the following general formula (1):

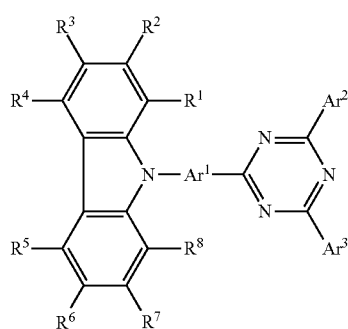

General Formula (1)

wherein in general formula (1), $R^1$ to $R^8$ each independently represent a hydrogen atom or a substituent, provided that only one of $R^1$, $R^2$, $R^3$, or $R^4$, and only one of $R^5$, $R^6$, $R^7$, or $R^8$ represent a substituted or unsubstituted carbazolyl group; and $Ar^1$ to $Ar^3$ each independently represent a substituted or unsubstituted aromatic ring or heteroaromatic ring, provided that when $Ar^1$ is a 1,4-phenylene group, $Ar^2$ and $Ar^3$ are independently a phenyl group, a naphthyl group, a phenylphenyl group, or a carbazolyl group, and $R^3$ and $R^6$ are a carbazolyl group, then $R^3$ and $R^6$ are a substituted or unsubstituted 1-carbazolyl group, a substituted or unsubstituted 2-carbazolyl group or a substituted or unsubstituted 4-carbazolyl group, provided that when $R^3$ is a 9-carbazolyl group, then $R^1$ is not a 9-carbazolyl group, and provided that when $R^2$ is a 1-carbazolyl group, a 2-carbazolyl group, a 3-carbazolyl group or a 4-carbazolyl group, then $R^7$ is not a 1-carbazolyl group, a 2-carbazolyl group, a 3-carbazolyl group or a 4-carbazolyl group, and allowing light comprising a delayed fluorescent component to be emitted from the compound.

2. The method according to claim 1, wherein in the general formula (1), at least one of $R^3$ or $R^6$ represents a substituted or unsubstituted carbazolyl group.

3. The method according to claim 1, wherein the carbazolyl group is a 1-carbazolyl group, a 2-carbazolyl group, a 3-carbazolyl group, or a 4-carbazolyl group.

4. The method according to claim 1, wherein the carbazolyl group has a substituent on the nitrogen atom in the carbazole ring structure.

5. The method according to claim 1, wherein in the general formula (1), at least one of $Ar^1$, $Ar^2$, or $Ar^3$ represents a benzene ring or a naphthalene ring.

6. The method according to claim 1, wherein in general formula (1), at least two of $Ar^1$, $Ar^2$, or $Ar^3$ represent the same aromatic rings or heteroaromatic rings.

7. The method according to claim 1, wherein in general formula (1), $Ar^1$, $Ar^2$, and $Ar^3$ represent benzene rings.

8. The method according to claim 1, wherein the emitted light is visible light.

9. The method for emitting delayed fluorescent light according to claim 1, wherein in general formula (1), at least one of $Ar^2$ and $Ar^3$ is a substituted or unsubstituted monocyclic heteroaromatic ring.

10. The method for emitting delayed fluorescent light according to claim 1, wherein in general formula (1), $Ar^2$ and $Ar^3$ are independently a substituted or unsubstituted monocyclic heteroaromatic ring.

11. The method for emitting delayed fluorescent light according to claim 1, wherein in general formula (1), at least one of $Ar^2$ and $Ar^3$ is selected from the group consisting of:

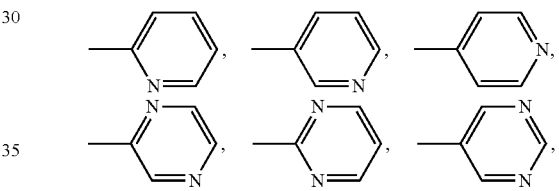

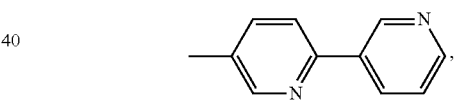

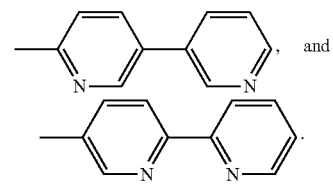

and

12. The method for emitting delayed fluorescent light according to claim 1, wherein in general formula (1), $R^3$ and $R^6$ are a substituted or unsubstituted 1-carbazolyl group.

13. The method for emitting delayed fluorescent light according to claim 1, wherein in general formula (1), $R^3$ and $R^6$ are a substituted or unsubstituted 2-carbazolyl group.

14. The method for emitting delayed fluorescent light according to claim 1, wherein in general formula (1), $R^3$ and $R^6$ are a substituted or unsubstituted 4-carbazolyl group.

15. An organic light-emitting delayed fluorescent device containing a substrate having thereon a light-emitting layer containing a compound represented by the following general formula (1):

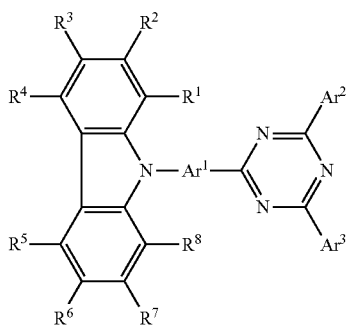

General Formula (1)

wherein in general formula (1), $R^1$ to $R^8$ each independently represent a hydrogen atom or a substituent, provided that only one of $R^1$, $R^2$, $R^3$, or $R^4$, and only one of $R^5$, $R^6$, $R^7$, or $R^8$ represent a substituted or unsubstituted carbazolyl group; and $Ar^1$ to $Ar^3$ each independently represent a substituted or unsubstituted aromatic ring or heteroaromatic ring, provided that when $R^3$ is a 9-carbazolyl group, then $R^1$ is not a 9-carbazolyl group, provided that when $R^2$ is a 1-carbazolyl group, a 2-carbazolyl group, a 3-carbazolyl group or a 4-carbazolyl group, then $R^7$ is not a 1-carbazolyl group, a 2-carbazolyl group, a 3-carbazolyl group or a 4-carbazolyl group, and wherein the compound represented by the general formula (1) emits light comprising a delayed fluorescent component.

16. The organic light-emitting device according to claim 15, wherein the organic light-emitting device is an organic electroluminescent device.

17. An organic light-emitting delayed fluorescent device containing a substrate having thereon a light-emitting layer containing a compound represented by the following general formula (1):

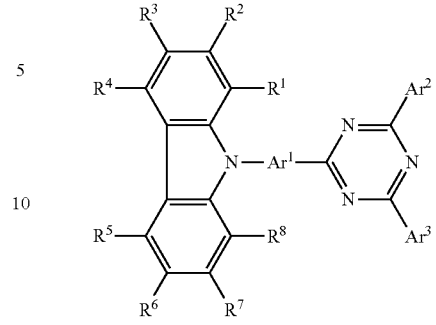

General Formula (1)

wherein in general formula (1), $R^1$ to $R^8$ each independently represent a hydrogen atom or a substituent, provided that only one of $R^1$, $R^2$, $R^3$, or $R^4$, and only one of $R^5$, $R^6$, $R^7$, or $R^8$ represent a substituted or unsubstituted carbazolyl group; and $Ar^1$ to $Ar^3$ each independently represent a substituted or unsubstituted aromatic ring or heteroaromatic ring, wherein the organic light-emitting device emits delayed fluorescent light, provided that when $Ar^1$ is a 1,4-phenylene group, $Ar^2$ and $Ar^3$ are independently a phenyl group, a naphthyl group, a phenylphenyl group, or a carbazolyl group, and $R^3$ and $R^6$ are a carbazolyl group, then $R^3$ and $R^6$ are a substituted or unsubstituted 1-carbazolyl group, a substituted or unsubstituted 2-carbazolyl group or a substituted or unsubstituted 4-carbazolyl group, provided that when $R^3$ is a 9-carbazolyl group, then $R^1$ is not a 9-carbazolyl group, provided that when $R^2$ is a 1-carbazolyl group, a 2-carbazolyl group, a 3-carbazolyl group or a 4-carbazolyl group, then $R^7$ is not a 1-carbazolyl group, a 2-carbazolyl group, a 3-carbazolyl group or a 4-carbazolyl group, and wherein the compound represented by the general formula (1) emits light comprising a delayed fluorescent component.

18. The organic light-emitting device according to claim 15 or claim 17, wherein the emitted light is visible light.

* * * * *